(12) United States Patent
Antonov et al.

(10) Patent No.: US 8,383,584 B2
(45) Date of Patent: Feb. 26, 2013

(54) HCV INHIBITING MACROCYCLIC PHENYLCARBAMATES

(75) Inventors: Dmitry Antonov, Huddinge (SE); Susana Ayesa Alvarez, Huddinge (SE); Anna Karin Gertrud Linnea Belfrage, Huddinge (SE); Carl Erik Daniel Jönsson, Huddinge (SE); David Craig McGowan, Brussels (BE); Karl Magnus Nilsson, Huddinge (SE); Pierre Jean-Marie Bernard Raboisson, Rosieres (BE); Åsa Annica Kristina Rosenquist, Huddinge (SE); Bengt Bertil Samuelsson, Huddinge (SE)

(73) Assignees: Medivir AB (SE); Janssen R&D Ireland (IE)

( * ) Notice: Subject to any disclaimer, the term of this patent is extended or adjusted under 35 U.S.C. 154(b) by 636 days.

(21) Appl. No.: 12/526,085

(22) PCT Filed: Feb. 8, 2008

(86) PCT No.: PCT/EP2008/051556
§ 371 (c)(1),
(2), (4) Date: Aug. 6, 2009

(87) PCT Pub. No.: WO2008/096001
PCT Pub. Date: Aug. 14, 2008

(65) Prior Publication Data
US 2010/0041728 A1 Feb. 18, 2010

(30) Foreign Application Priority Data

Feb. 8, 2007 (EP) .................................. 07102006
Feb. 8, 2007 (EP) .................................. 07102007
Feb. 8, 2007 (EP) .................................. 07102008

(51) Int. Cl.
*A61K 38/00* (2006.01)
*A01N 37/18* (2006.01)

(52) U.S. Cl. ........................................ 514/4.3

(58) Field of Classification Search .................. None
See application file for complete search history.

(56) References Cited

U.S. PATENT DOCUMENTS 7,666,834 B2 * 2/2010 Simmen et al. ............... 514/1.1

FOREIGN PATENT DOCUMENTS

| WO | WO 00/59929 | 10/2000 |
|----|----|----|
| WO | WO 2006/020276 | 2/2006 |
| WO | WO 2007/014922 | 2/2007 |
| WO | WO 2007/014923 | 2/2007 |
| WO | WO 2007/044933 | 4/2007 |

* cited by examiner

Primary Examiner — Thomas Heard
(74) Attorney, Agent, or Firm — Andrea Jo Kamage

(57) ABSTRACT

Compounds of the formula I:

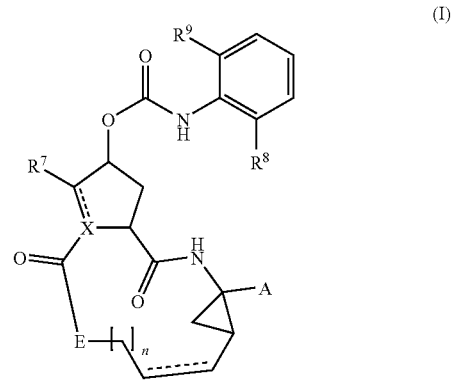

including a stereoisomer thereof, or an N-oxide, a pharmaceutically acceptable addition salt, or a pharmaceutically acceptable addition solvate thereof; useful as HCV inhibitors; processes for preparing these compounds as well as pharmaceutical compositions comprising these compounds as active ingredient.

19 Claims, No Drawings

HCV INHIBITING MACROCYCLIC PHENYLCARBAMATES

CROSS REFERENCE TO RELATED APPLICATIONS

This application is the national stage of PCT Application No. PCT/EP2008/051556 filed Feb. 8, 2008, which claims priority from European Patent Application No. 07102006.9, filed Feb. 8, 2007; European Patent Application No. 07102007.7 filed Feb. 8, 2007; and, European Patent Application No. 07102008, filed Feb. 8, 2007, the entire disclosures of which are hereby incorporated in their entirety.

TECHNICAL FIELD

This invention relates to macrocyclic compounds having inhibitory activity on the NS3 serine protease of HCV. It further concerns compositions comprising these compounds as active ingredients as well as processes for preparing these compounds and compositions.

BACKGROUND OF THE INVENTION

Hepatitis C virus (HCV) is the leading cause of chronic liver disease worldwide and has become a focus of considerable medical research. HCV is a member of the Flaviviridae family of viruses in the *hepacivirus* genus, and is closely related to the *flavivirus* genus, which includes a number of viruses implicated in human disease, such as dengue virus and yellow fever virus, and to the animal pestivirus family, which includes bovine viral diarrhea virus (BVDV). The genome of HCV comprises both 5' and 3' untranslated regions that adopt RNA secondary structures, and a central open reading frame that encodes a single polyprotein. The polyprotein encodes ten gene products, which are generated from the precursor polyprotein by an orchestrated series of co- and posttranslational endoproteolytic cleavages mediated by both host and viral proteases. The viral structural proteins include the core nucleocapsid protein, and two envelope glycoproteins E1 and E2. The non-structural (NS) proteins encode some essential viral enzymatic functions (helicase, polymerase, protease), as well as proteins of unknown function. Replication of the viral genome is mediated by an RNA-dependent RNA polymerase, encoded by non-structural protein 5b (NS5B). In addition to the polymerase, the viral helicase and protease functions, both encoded in the bifunctional NS3 protein, have been shown to be essential for replication of HCV RNA. In addition to the NS3 serine protease, HCV also encodes a metalloproteinase in the NS2 region.

Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis leading to cirrhosis, end-stage liver disease, and HCC (hepatocellular carcinoma), making it the leading cause of liver transplantations.

There are 6 major HCV genotypes and more than 50 subtypes, which are differently distributed geographically. HCV type 1 is the predominant genotype in Europe and the US. The extensive genetic heterogeneity of HCV has important diagnostic and clinical implications, perhaps explaining difficulties in vaccine development and the lack of response to current therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

Current HCV therapies are based on (pegylated) interferon-alpha (IFN-$\alpha$) in combination with ribavirin. This combination therapy yields a sustained virologic response in more than 40% of patients infected by genotype 1 viruses and about 80% of those infected by genotypes 2 and 3. Beside the limited efficacy on HCV type 1, this combination therapy has significant side effects and is poorly tolerated in many patients. Major side effects include influenza-like symptoms, hematologic abnormalities, and neuropsychiatric symptoms. Hence there is a need for more effective, convenient and better-tolerated treatments.

A number of similar HCV protease inhibitors have been disclosed in the academic and patent literature. The sustained administration of HCV protease inhibitors usually leads to the selection of resistant HCV mutants, so called drug escape mutants. These have characteristic mutations in the HCV protease genome, notably D168V, D168Y and/or A165S. Accordingly, there is a need for additional drugs with different resistance patterns to provide failing patients with treatment options. Such drugs may find use in combination therapy, which is expected to become the norm in the future, even for first line treatment.

Experience with HIV drugs, in particular with HIV protease inhibitors, has taught that sub-optimal pharmacokinetics and complex dosing regimes quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$, is essential to slow down the development of drug escape mutants.

Achieving the necessary pharmacokinetics and drug metabolism to allow such trough levels provides a stringent challenge to drug design. Known HCV protease inhibitors, with multiple peptide bonds, pose additional pharmacokinetic hurdles to effective dosage regimes.

There is a need for HCV inhibitors that may overcome the disadvantages of current HCV therapy such as side effects, limited efficacy, the emerging of resistance, and compliance failures.

The present invention concerns inhibitors of HCV replication that exhibit at least one improved property in view of the compounds of the prior art compounds. In particular, the inhibitors of the present invention are superior in one or more of the following pharmacological related properties, i.e. potency, decreased cytotoxicity, improved pharmacokinetics, improved resistance profile, acceptable dosage and pill burden.

BRIEF DESCRIPTION OF THE INVENTION

The present invention concerns inhibitors of HCV replication, which can be represented by formula (I):

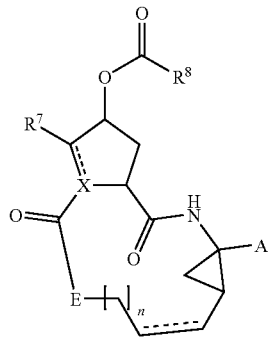

(I)

including the stereoisomers thereof, wherein

A is —C(=O)OR$^1$, —C(=O)—NH—SO$_2$—R$^2$, —C(=O)C(=O)NR$^{3a}$R$^{3b}$, —C(=O)—NH—SO$_2$—NR$^{3a}$R$^{3b}$, —C(=O)NH—P(=O)(OR$^{4a}$)(R$^{4b}$), or —P(=O)(OR$^{4a}$)(R$^{4b}$) wherein;

R$^1$ is hydrogen; aryl; Het; C$_{3-7}$cycloalkyl optionally substituted with C$_{1-6}$alkyl; or C$_{1-6}$alkyl optionally substituted with C$_{3-7}$cycloalkyl, aryl or with Het;

R$^2$ is aryl; Het; C$_{3-7}$cycloalkyl optionally substituted with C$_{1-6}$alkyl; or C$_{1-6}$alkyl optionally substituted with C$_{3-7}$cycloalkyl, aryl, or with Het;

R$^{3a}$ and R$^{3b}$ each independently are hydrogen; C$_{1-6}$alkyl optionally substituted with C$_{1-6}$alkoxy, hydroxy, halo, C$_{3-7}$cycloalkyl, aryl, or with Het; aryl; C$_{2-6}$alkenyl; Het; C$_{3-7}$cycloalkyl optionally substituted with C$_{1-6}$alkyl; or R$^{3a}$ and R$^{3b}$ together with the nitrogen atom to which they are attached form a group Het$^1$; and R$^{3a}$ may also be C$_{1-6}$alkoxy;

R$^{4a}$ is hydrogen, C$_{1-6}$alkyl, C$_{2-6}$alkenyl, C$_{3-7}$cycloalkyl, aryl, or C$_{1-6}$alkyl optionally substituted with C$_{3-7}$cycloalkyl or aryl;

R$^{4b}$ is R$^{4b'}$, OR$^{4b'}$ or NHR$^{4b'}$;

R$^{4b'}$ is C$_{1-6}$alkyl, C$_{2-6}$alkenyl, C$_{3-7}$cycloalkyl, aryl, or C$_{1-6}$alkyl optionally substituted with C$_{3-7}$cycloalkyl or with aryl;

X is N, CH and when X bears a double bond it is C;

E is NR$^5$, or when X is N then E is NR$^5$ or CR$^{6a}$R$^{6b}$;

R$^5$ is hydrogen, C$_{1-6}$alkyl, C$_{1-6}$alkoxyC$_{1-6}$alkyl, or C$_{3-7}$cycloalkyl;

R$^{6a}$ and R$^{6b}$ are independently hydrogen or C$_{1-6}$alkyl, or R$^{6a}$ and R$^{6b}$ together with the carbon atom to which they are attached form C$_{3-7}$cycloalkyl;

n is 3, 4, 5 or 6;

each dotted line - - - independently represents an optional double bond;

R$^7$ is hydrogen, or where X is C or CH, R$^7$ may also be C$_{1-6}$alkyl;

R$^8$ is a radical of formula

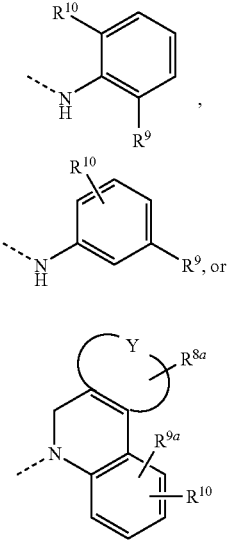

R$^{8a}$ and R$^{9a}$ each independently are hydrogen, C$_{1-6}$alkyl, C$_{2-6}$alkenyl, C$_{1-6}$alkoxy, hydroxy, halo, polyhaloC$_{1-6}$alkyl, cyano, amino, mono- or C$_{1-6}$dialkylamino;

each R$^9$ independently is C$_{1-6}$alkyl optionally substituted with C$_{1-6}$alkoxy, hydroxy, or halo; C$_{3-7}$cycloalkyl; C$_{2-6}$alkenyl; C$_{1-6}$alkoxy; C$_{3-7}$cycloalkyloxy; aryloxy; Het-O—; hydroxy; cyano; polyhaloC$_{1-6}$alkyl; mono- or C$_{1-6}$dialkylamino;

each R$^{10}$ independently is hydrogen, C$_{1-6}$alkyl, C$_{2-6}$alkenyl, C$_{1-6}$alkoxy, hydroxy, halo, polyhaloC$_{1-6}$alkyl, cyano, amino, mono- or C$_{1-6}$dialkylamino;

each aryl independently is phenyl optionally substituted with one, two or three substituents selected from halo, hydroxy, nitro, cyano, carboxyl, C$_{1-6}$alkyl, C$_{1-6}$alkoxy, C$_{1-6}$alkoxyC$_{1-6}$alkyl, C$_{1-6}$alkylcarbonyl, amino, mono- or diC$_{1-6}$alkylamino, azido, mercapto, C$_{1-6}$alkylthio, polyhaloC$_{1-6}$alkyl, polyhaloC$_{1-6}$alkoxy, C$_{3-7}$cycloalkyl, and Het$^1$;

each Het independently is a 5 or 6 membered saturated, partially unsaturated or completely unsaturated heterocyclic ring containing 1, 2, 3 or 4 heteroatoms each independently selected from nitrogen, oxygen and sulfur, said heterocyclic ring being optionally substituted with one, two or three substituents each independently selected from halo, hydroxy, nitro, cyano, carboxyl, C$_{1-6}$alkyl, C$_{1-6}$alkoxy, C$_{1-6}$alkoxyC$_{1-6}$alkyl, C$_{1-6}$alkylcarbonyl, amino, mono- or diC$_{1-6}$alkylamino, azido, mercapto, polyhaloC$_{1-6}$alkyl, polyhaloC$_{1-6}$alkoxy, C$_{3-7}$cycloalkyl, Het$^1$;

each Het$^1$ independently is pyrrolidinyl, piperidinyl, piperazinyl, 4-C$_{1-6}$alkyl-piperazinyl, 4-C$_{1-6}$alkylcarbonyl-piperazinyl, and morpholinyl and wherein the morpholinyl and piperidinyl groups may optionally substituted with one or two C$_{1-6}$alkyl radicals;

or the N-oxides, pharmaceutically acceptable addition salts, or pharmaceutically acceptable solvates thereof.

The invention relates to the compounds of formula (I) per se, and the N-oxides, pharmaceutically acceptable addition salts, and stereochemically isomeric forms thereof, for use as a medicament. The invention further relates to pharmaceutical compositions comprising the aforementioned compounds for administration to a subject suffering from HCV infection. The pharmaceutical compositions may comprise combinations of the aforementioned compounds with other anti-HCV agents.

The invention also relates to the use of a compound of formula (I), an N-oxide, a pharmaceutically acceptable addition salt, or stereochemically isomeric form thereof, for the manufacture of a medicament for inhibiting HCV replication. Or the invention relates to a method of inhibiting HCV replication in a warm-blooded animal, said method comprising the administration of an effective amount of a compound of formula (I), an N-oxide, a pharmaceutically acceptable addition salt, or stereochemically isomeric form thereof.

DETAILED DESCRIPTION OF THE INVENTION

As used in the foregoing and hereinafter, the following definitions apply unless otherwise noted.

As used herein "$C_{1-4}$alkyl" as a group or part of a group defines straight or branched chain saturated hydrocarbon radicals having from 1 to 4 carbon atoms such as for example methyl, ethyl, 1-propyl, 2-propyl, 1-butyl, 2-butyl, 2-methyl-1-propyl; "$C_{1-6}$alkyl" encompasses $C_{1-4}$alkyl radicals and the higher homologues thereof having 5 or 6 carbon atoms such as, for example, 1-pentyl, 2-pentyl, 3-pentyl, 1-hexyl, 2-hexyl, 2-methyl-1-butyl, 2-methyl-1-pentyl, 2-ethyl-1-butyl, 3-methyl-2-pentyl, and the like. Of interest amongst $C_{1-6}$alkyl is $C_{1-4}$alkyl.

The term "$C_{2-6}$alkenyl" as a group or part of a group defines straight and branched chained hydrocarbon radicals having saturated carbon-carbon bonds and at least one double bond, and having from 2 to 6 carbon atoms, such as, for example, ethenyl (or vinyl), 1-propenyl, 2-propenyl (or allyl), 1-butenyl, 2-butenyl, 3-butenyl, 2-methyl-2-propenyl, 2-pentenyl, 3-pentenyl, 2-hexenyl, 3-hexenyl, 4-hexenyl, 2-methyl-2-butenyl, 2-methyl-2-pentenyl and the like. Of interest amongst $C_{2-6}$alkenyl is $C_{2-4}$alkenyl.

$C_{3-7}$cycloalkyl is generic to cyclopropyl, cyclobutyl, cyclopentyl, cyclohexyl and cycloheptyl.

$C_{1-6}$alkoxy means $C_{1-6}$alkyloxy wherein $C_{1-6}$alkyl is as defined above and is bonded to an oxygen atom, i.e. —O—$C_{1-6}$alkyl. Of interest amongst $C_{1-6}$alkoxy are methoxy, ethoxy and propoxy.

The term halo is generic to fluoro, chloro, bromo and iodo, in particular fluoro or chloro.

The term "polyhalo$C_{1-6}$alkyl" as a group or part of a group, e.g. in polyhalo$C_{1-6}$alkoxy, is defined as mono- or polyhalo substituted $C_{1-6}$alkyl, in particular $C_{1-6}$alkyl substituted with up to one, two, three, four, five, six, or more halo atoms, such as methyl or ethyl with one or more fluoro atoms, for example, difluoromethyl, trifluoromethyl, trifluoroethyl. Preferred is trifluoromethyl. Also included are perfluoro$C_{1-6}$alkyl groups, which are $C_{1-6}$alkyl groups wherein all hydrogen atoms are replaced by fluoro atoms, e.g. pentafluoroethyl. In case more than one halogen atom is attached to an alkyl group within the definition of polyhalo$C_{1-6}$alkyl, the halogen atoms may be the same or different.

As used herein before, the term (=O) or oxo forms a carbonyl moiety when attached to a carbon atom, a sulfoxide moiety when attached to a sulfur atom and a sulfonyl moiety when two of said terms are attached to a sulfur atom. Whenever a ring or ring system is substituted with an oxo group, the carbon atom to which the oxo is linked is a saturated carbon.

The radical Het is a heterocycle as specified in this specification and claims. Examples of Het comprise, for example, pyrrolidinyl, piperidinyl, morpholinyl, thiomorpholinyl, piperazinyl, pyrrolyl, pyrazolyl, imidazolyl, oxazolyl, isoxazolyl, thiazinolyl, isothiazinolyl, thiazolyl, isothiazolyl, oxadiazolyl, thiadiazolyl, triazolyl (including 1,2,3-triazolyl, 1,2,4-triazolyl), tetrazolyl, furanyl, thienyl, pyridyl, pyrimidyl, pyridazinyl, triazinyl, and the like. Of interest amongst the Het radicals are those which are non-saturated, in particular those having an aromatic character. Of further interest are those Het radicals having one or two nitrogens.

Each of the Het radicals mentioned in this and the following paragraph may be optionally substituted with the number and kind of substituents mentioned in the definitions of the compounds of formula (I) or any of the subgroups of compounds of formula (I). Some of the Het radicals mentioned in this and the following paragraph may be substituted with one, two or three hydroxy substituents. Such hydroxy substituted rings may occur as their tautomeric forms bearing keto groups. For example a 3-hydroxypyridazine moiety can occur in its tautomeric form 2H-pyridazin-3-one. Where Het is piperazinyl, it preferably is substituted in its 4-position by a substituent linked to the 4-nitrogen with a carbon atom, e.g. 4-$C_{1-6}$alkyl, 4-polyhalo$C_{1-6}$alkyl, $C_{1-6}$alkoxy$C_{1-6}$alkyl, $C_{1-6}$alkylcarbonyl, $C_{3-7}$cycloalkyl.

Interesting Het radicals comprise, for example pyrrolidinyl, piperidinyl, morpholinyl, thiomorpholinyl, piperazinyl, pyrrolyl, pyrazolyl, imidazolyl, oxazolyl, isoxazolyl, thiazolyl, isothiazolyl, oxadiazolyl, thiadiazolyl, triazolyl (including 1,2,3-triazolyl, 1,2,4-triazolyl), tetrazolyl, furanyl, thienyl, pyridyl, pyrimidyl, pyridazinyl, pyrazolyl, triazinyl, or any of such heterocycles condensed with a benzene ring, such as indolyl, indazolyl (in particular 1H-indazolyl), indolinyl, quinolinyl, tetrahydroquinolinyl (in particular 1,2,3,4-tetrahydroquinolinyl), isoquinolinyl, tetrahydroisoquinolinyl (in particular 1,2,3,4-tetrahydroisoquinolinyl), quinazolinyl, phthalazinyl, benzimidazolyl, benzoxazolyl, benzisoxazolyl, benzothiazolyl, benzoxadiazolyl, benzothiadiazolyl, benzofuranyl, benzothienyl.

The Het radicals pyrrolidinyl, piperidinyl, morpholinyl, thiomorpholinyl, piperazinyl, 4-substituted piperazinyl preferably are linked via their nitrogen atom (i.e. 1-pyrrolidinyl, 1-piperidinyl, 4-thiomorpholinyl, 4-morpholinyl, 1-piperazinyl, 4-substituted 1-piperazinyl).

It should be noted that the radical positions on any molecular moiety used in the definitions may be anywhere on such moiety as long as it is chemically stable.

Radicals used in the definitions of the variables include all possible isomers unless otherwise indicated. For instance pyridyl includes 2-pyridyl, 3-pyridyl and 4-pyridyl; pentyl includes 1-pentyl, 2-pentyl and 3-pentyl.

When any variable occurs more than one time in any moiety, each definition is independent.

Whenever used hereinafter, the term "compounds of formula (I)", or "the present compounds" or similar terms, it is meant to include the compounds of formula (I), their N-oxides, pharmaceutically acceptable addition salts, and stereochemically isomeric forms. One embodiment comprises the compounds of formula (I) or any subgroup of compounds of formula (I) specified herein, and the pharmaceutically acceptable addition salts and the possible stereoisomeric forms thereof.

The compounds of formula (I) have several centers of chirality and exist as stereochemically isomeric forms. The term "stereochemically isomeric forms" as used herein defines all the possible compounds made up of the same atoms bonded by the same sequence of bonds but having different three-dimensional structures which are not interchangeable, which the compounds of formula (I) may possess.

With reference to the instances where (R) or (S) is used to designate the absolute configuration of a chiral atom within a substituent, the designation is done taking into consideration the whole compound and not the substituent in isolation.

Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyl-tartaric acid, ditoluoyltartaric acid and camphorsulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereo specifically. Preferably, if a specific stereoisomer is desired, said compound are synthesized by stereospecific methods of preparation. These methods will advantageously employ enantiomerically pure starting materials.

The diastereomeric racemates of the compounds of formula (I) can be obtained separately by conventional methods. Appropriate physical separation methods that may advantageously be employed are, for example, selective crystallization and chromatography, e.g. column chromatography.

For some of the compounds of formula (I), the N-oxides, the pharmaceutically acceptable addition salts, and solvates thereof, and the intermediates used in the preparation thereof, the absolute stereochemical configuration was not experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

The pharmaceutically acceptable addition salts comprise the therapeutically active non-toxic acid and base addition salt forms of the compounds of formula (I). The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxylbutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salts also is meant to comprise the solvates, which the compounds of formula (I) as well as the salts thereof, are able to form. Such solvates are for example hydrates, alcoholates, e.g. ethanolates, propanolates, and the like.

The N-oxide forms of the present compounds are meant to comprise the compounds of formula (I) wherein one or several nitrogen atoms are oxidized to a so-called N-oxide.

Some of the compounds of formula (I) may also exist in their tautomeric form. Such forms although not explicitly indicated in the above formula are intended to be included within the scope of the present invention.

As mentioned above, the compounds of formula (I) have several asymmetric centers. In order to more efficiently refer to each of these asymmetric centers, the numbering system as indicated in the following structural formula will be used.

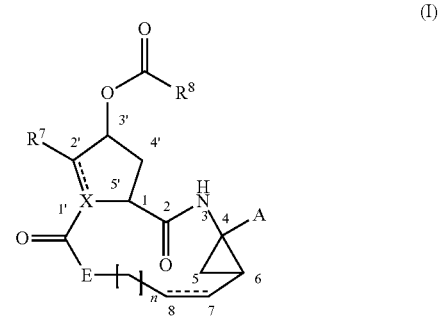

(I)

Asymmetric centers are present at positions 1, 4 and 6 of the macrocycle as well as at the carbon atom 3' in the 5-membered ring, at carbon atom 2' when the $R^7$ substituent is $C_{1-6}$alkyl, and at carbon atom 1' when X is CH. Each of these asymmetric centers can occur in their R or S configuration.

When X is N, the stereochemistry at position 1 preferably corresponds to that of an L-amino acid configuration, i.e. that of L-proline as shown below.

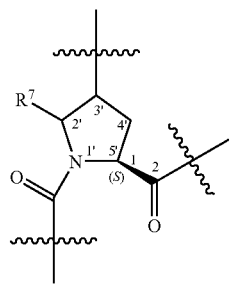

When X is CH, the 2 carbonyl groups substituted at positions 1' and 5' of the cyclopentane ring preferably are in a trans configuration. The carbonyl substituent at position 5' preferably is in that configuration that corresponds to an L-proline configuration. The carbonyl groups substituted at positions 1' and 5' preferably are as depicted below in the structure of the following formula:

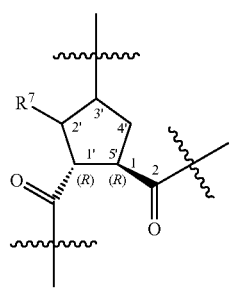

The compounds of formula (I) include a cyclopropyl group as represented in the structural fragment below:

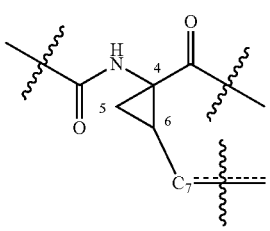

wherein $C_7$ represents the carbon at position 7 and carbons at position 4 and 6 are asymmetric carbon atoms of the cyclopropane ring. The presence of these two asymmetric centers means that the compounds can exist as mixtures of diastereomers, such as the diastereomers of compounds of formula (I) wherein the carbon at position 7 is configured either cis to the carbonyl or cis to the amide as shown below.

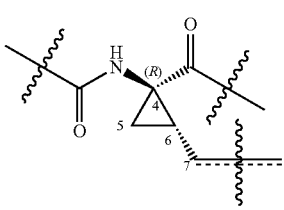

C7 cis to carbonyl

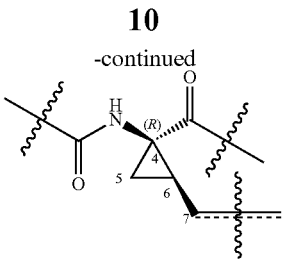

C7 cis to amide

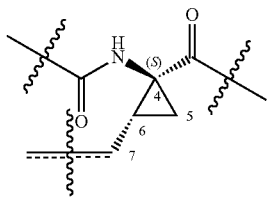

C7 cis to carbonyl

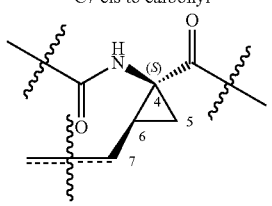

C7 cis to amide

One embodiment concerns compounds of formula I wherein the carbon at position 7 is configured cis to the carbonyl. Another embodiment concerns compounds of formula (I) wherein the configuration at the carbon at position 4 is R. A specific subgroup of compounds of formula (I) is that wherein the carbon at position 7 is configured cis to the carbonyl and wherein the configuration at the carbon at position 4 is R.

According one embodiment the cyclopropyl group ($C_4$—$C_5$—$C_6$) is linked to a group A that is a phosphonate group —P(=O)(OR$^{4a}$)(R$^{4b}$). According to this embodiment, the carbon at position 7 is configured in a cis relationship either to the phosphonate or to the amide as presented in the structural fragment below:

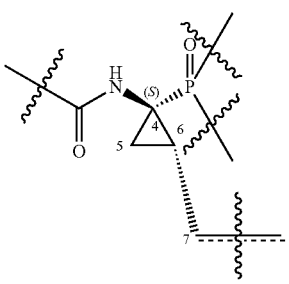

C7 cis to phosphonate

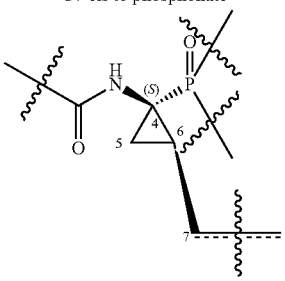

C7 cis to amide

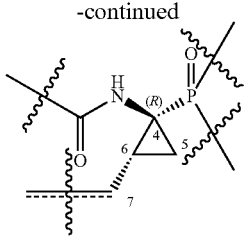

C7 cis to phosphonate

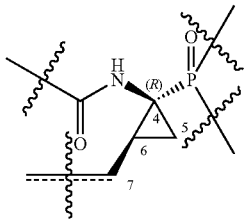

C7 cis to amide

One embodiment concerns compounds of formula (I) wherein the carbon at position 7 is configured cis to the phosphonate. Another embodiment concerns compounds of formula (I) wherein the configuration at the carbon at position 4 is S. A specific subgroup of compounds of formula (I) are those wherein the carbon at position 7 is configures cis to the phosphonate and wherein the configuration at the carbon at position 4 is S.

The compounds of formula (I) may include a proline residue i.e. X is N, or a cyclopentyl or cyclopentenyl residue, i.e. X is CH or C respectively. According to one embodiment of this invention the compounds comprise the partial structures:

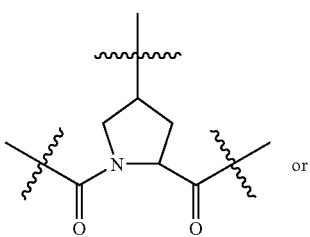

or

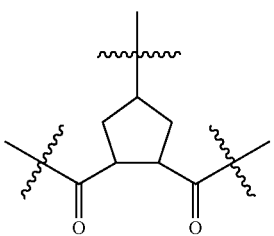

Further embodiments of the invention are compounds of formula (I) or any of the subgroups of compounds of formula (I), wherein $R^7$ is methyl, E is $NR^5$, X is C linked with a double bond to the carbon bearing $R^7$.

Preferred are the compounds of formula (I) wherein the substituent at the 1 (or 5') position and the ether-linked pyrimidine substituent at position 3' are in a trans configuration.

Of particular interest are the compounds of formula (I) wherein position 1 has the configuration corresponding to L-proline and the ether linked pyrimidine substituent at position 3' is in a trans configuration in respect of position 1.

Preferably the compounds of formula (I) have the stereochemistry as indicated in the structures of formulae (I-a) and (I-b) below:

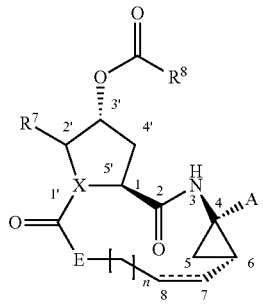

(I-a)

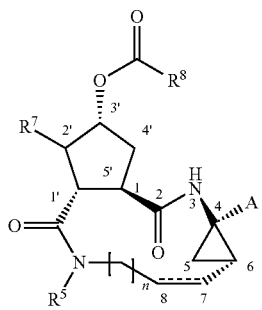

(I-b)

One embodiment of the present invention concerns compounds of formula (I) or of formula (I-a), (I-b) or of any subgroup of compounds of formula (I), wherein one or more of the following conditions apply:

(a) $R^7$ is hydrogen;
(b) X is nitrogen;
(c) E is $NR^5$;
(d) a double bond is present between carbon atoms 7 and 8.

A further embodiment of the present invention concerns compounds of formula (I) or of formulae (I-a), (I-b), or of any subgroup of compounds of formula (I), wherein one or more of the following conditions apply:

(a) $R^7$ is hydrogen;
(b) X is nitrogen;
(c) E is $CR^{6a}R^{6b}$;
(d) a double bond is present between carbon atoms 7 and 8.

A further embodiment of the present invention concerns compounds of formula (I) or of formulae (I-a), (I-b), or of any subgroup of compounds of formula (I), wherein one or more of the following conditions apply:

(a) $R^7$ is hydrogen;
(b) X is CH;
(c) E is $NR^5$, wherein $R^5$ is as defined above, particularly $R^5$ is hydrogen or $C_{1-6}$alkyl;
(d) a double bond is present between carbon atoms 7 and 8.

Particular subgroups of compounds of formula (I) are those represented by the structural formulae (I-c), (I-d) and (I-e) below:

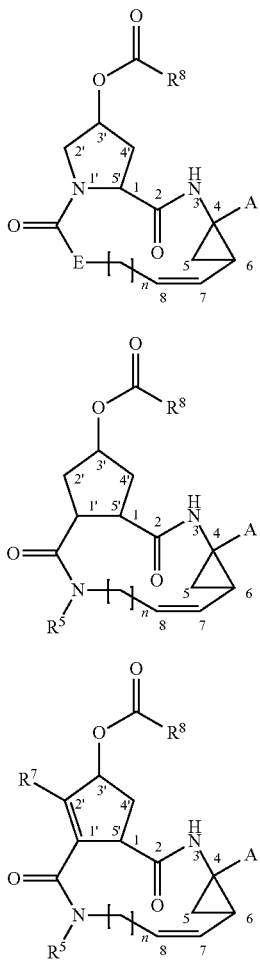

(I-c)

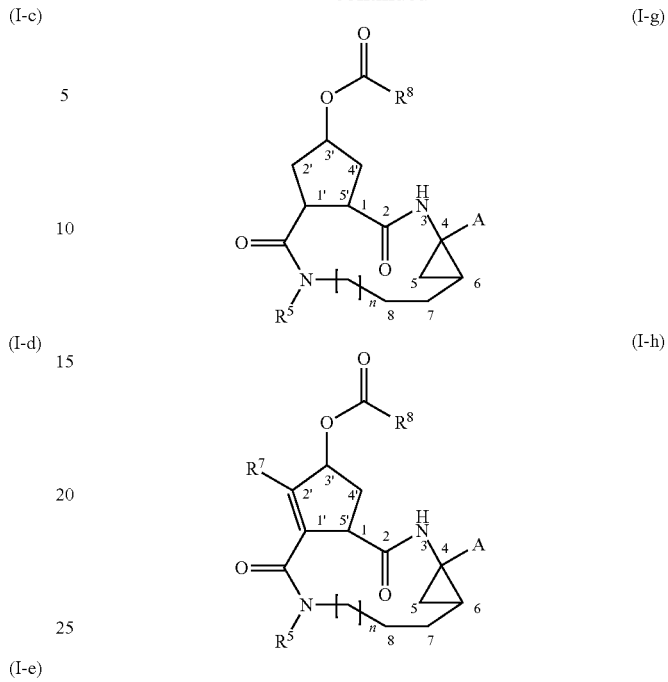

(I-d)

(I-g)

(I-h)

Amongst the compounds of formula (I-c), (I-d) and (I-e), those having the stereochemical configuration shown in formulae (I-a), and (I-b), respectively, are of particular interest.

The double bond between carbon atoms 7 and 8 in the compounds of formula (I), or in any subgroup of compounds of formula (I), may be in a cis or in a trans configuration. Preferably the double bond between carbon atoms 7 and 8 is in a cis configuration, as depicted in formulae (I-c), (I-d) and (I-e).

Other particular subgroups of compounds of formula (I) are those represented by the following structural formulae:

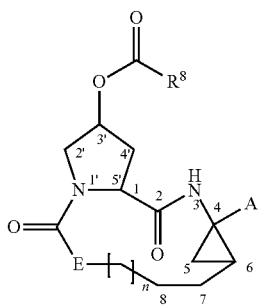

(I-f)

Of particular interest amongst the compounds of formulae (I-f), (I-g) or (I-h) are those having the stereochemical configuration of the compounds of formulae (I-a) and (I-b).

In (I-a), (I-b), (I-c), (I-d), (I-e), (I-f), (I-g) or (I-h), where applicable, A, E, X, n, $R^5$, $R^7$, $R^8$ and $R^9$ are as specified in the definitions of the compounds of formula (I) or of any of the subgroups of compounds of formula (I) specified herein.

It is to be understood that the above defined subgroups of compounds of formulae (I-a), (I-b), (I-c), (I-d) or (I-e), as well as any other subgroup defined herein, are meant to also comprise any N-oxides, addition salts, and stereochemically isomeric forms of such compounds.

When n is 2, the moiety —$CH_2$— bracketed by "n" corresponds to ethanediyl in the compounds of formula (I) or in any subgroup of compounds of formula (I). When n is 3, the moiety —$CH_2$— bracketed by "n" corresponds to propanediyl in the compounds of formula (I) or in any subgroup of compounds of formula (I). When n is 4, the moiety —$CH_2$— bracketed by "n" corresponds to butanediyl in the compounds of formula (I) or in any subgroup of compounds of formula (I). When n is 5, the moiety —$CH_2$— bracketed by "n" corresponds to pentanediyl in the compounds of formula (I) or in any subgroup of compounds of formula (I). When n is 6, the moiety —$CH_2$— bracketed by "n" corresponds to hexanediyl in the compounds of formula (I) or in any subgroup of compounds of formula (I). Particular subgroups of the compounds of formula (I) are those compounds wherein n is 4 or 5.

Embodiments of the invention are compounds of formula (I) or any of the subgroups of compounds of formula (I) wherein A is —C(=O)$OR^1$ in particular wherein $R^1$ is $C_{1-6}$alkyl, such as methyl, ethyl, or tert-butyl, and most preferably where $R^1$ is hydrogen.

A further embodiment of the invention are compounds of formula (I) or any of the subgroups of compounds of formula (I) wherein A is —C(=O)—NH—$SO_2$—$R^2$, in particular wherein $R^2$ is $C_{3-7}$cycloalkyl, phenyl or a group Het, e.g. thiazolyl or pyridyl, either of which is optionally substituted with one or more, such as one or two substituents selected from $C_{1-6}$alkyl, $C_{1-6}$alkoxy, trifluoromethyl, and halo, or in particular with one or two substituents selected from methyl, fluoro and chloro. For example $R^2$ can be 1-methylcyclopropyl.

A further embodiment of the invention are compounds of formula (I) or any of the subgroups of compounds of formula (I) wherein A is —C(=O)C(=O)$NR^{3a}R^{3b}$, in particular wherein $R^{3a}$ and $R^{3b}$ are independently selected from hydrogen, $C_{1-6}$alkyl, optionally substituted with aryl, and $C_{2-6}$alkenyl. In one embodiment, one of $R^{3a}$ and $R^{3b}$ is hydrogen and the other is 3-propenyl, cyclopropylmethyl or cyclopropyl. In a further embodiment, $R^{3a}$ and $R^{3b}$ are both hydrogen.

A further embodiment of the invention are compounds of formula (I), or any of the subgroups of compounds of formula (I), wherein A is —C(=O)—NH—P(=O)(O$R^{4a}$)($R^{4b}$), in particular wherein $R^{4a}$ is $C_{1-6}$alkyl, especially ethyl or isopropyl and $R^{4b}$ is O$R^{4b'}$ and $R^{4b'}$ is $C_{1-6}$alkyl, such as ethyl or isopropyl.

A further embodiment of the invention are compounds of formula (I), or any of the subgroups of compounds of formula (I), wherein A is —P(=O)(O$R^{4a}$)($R^{4b}$), in particular wherein $R^{4a}$ is $C_{1-6}$alkyl, especially ethyl or isopropyl and $R^{4b}$ is O$R^{4b'}$ and $R^{4b'}$ is $C_{1-6}$alkyl, especially ethyl or isopropyl.

Further embodiments of the invention are compounds of formula (I) or any of the subgroups of compounds of formula (I) wherein (a) $R^5$ is hydrogen; $C_{1-6}$alkyl; $C_{1-6}$alkoxy$C_{1-6}$alkyl; or $C_{3-7}$cycloalkyl (b) $R^5$ is hydrogen or $C_{1-6}$alkyl;

(c) $R^5$ is hydrogen.

Preferred embodiments of the invention are compounds of formula (I) or any of the subgroups of compounds of formula (I) wherein $R^5$ is hydrogen, or $C_{1-6}$alkyl, more preferably hydrogen or methyl.

Still a further embodiment concerns compounds of formula (I), (I-e) or any subgroup of compounds of formula (I) wherein $R^{6a}$ and $R^{6b}$ independently are hydrogen or $C_{1-6}$alkyl, e.g. methyl. Preferably $R^{6a}$ is hydrogen and $R^{6b}$ is methyl, or more preferably $R^{6a}$ and $R^{6b}$ are both hydrogen.

Embodiments of the invention are compounds of formula (I) or any of the subgroups of compounds of formula (I) wherein (a) $R^8$ is a radical of formula:

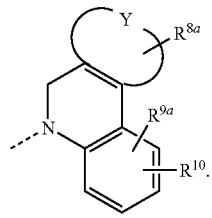

; or (b) $R^8$ is a radical of formula:

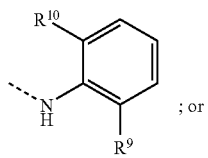

; or (c) $R^8$ is a radical of formula:

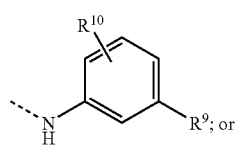

Embodiments of the invention are compounds of formula (I) or any of the subgroups of compounds of formula (I) wherein:

(d) $R^8$ is a radical of formula:

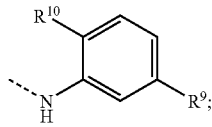

(e) $R^8$ is a radical of formula:

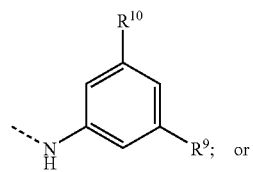

; or (f) $R^8$ is a radical of formula:

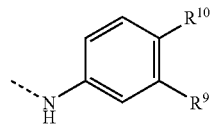

Embodiments of the invention are compounds of formula (I) or any of the subgroups of compounds of formula (I) wherein $R^9$ and $R^{10}$, or one of $R^9$ and $R^{10}$ are:

$R^9$ is $C_{1-6}$alkyl (e.g. methyl, ethyl or isopropyl); $C_{1-6}$alkoxy (e.g. methoxy, ethoxy or isopropoxy); aryloxy; Het-O—; cyano; or $R^9$ is $C_{1-6}$alkoxy (e.g. methoxy, ethoxy or isopropoxy) or aryloxy (e.g. phenoxy or 4-methoxy-phenoxy);

$R^{10}$ is hydrogen; $C_{1-6}$alkyl (e.g. methyl, ethyl or isopropyl); $C_{1-6}$alkoxy (e.g. methoxy, ethoxy or isopropoxy); cyano.

In the previous paragraph, aryl and Het are as specified above or herein after, in particular aryl is phenyl optionally substituted with $C_{1-6}$alkoxy (e.g. with methoxy, ethoxy or isopropoxy), more in particular 4-substituted phenyl; and Het in particular is pyridyl or pyrimidinyl.

Preferred embodiments of the invention are compounds of formula (I) or any of the subgroups of compounds of formula (I) wherein one of $R^9$ is hydrogen, methoxy or cyano.

Preferred embodiments of the invention are compounds of formula (I) or any of the subgroups of compounds of formula (I) wherein $R^9$ is cyano, $C_{1-6}$alkyloxycarbonyl, mono- and di($C_{1-6}$alkylamino), halo, amino, $C_{1-6}$alkoxy, aryloxy, $C_{1-6}$alkyl, Het; or wherein $R^9$ is cyano, $C_{1-6}$alkyloxycarbonyl (e.g. methoxycarbonyl), mono($C_{1-6}$alkyl-amino) (e.g.

methylamino), halo (e.g. chloro), $C_{1-6}$alkoxy (e.g. methoxy), phenoxy, $C_{1-6}$alkyl (e.g. methyl), thiazolyl optionally substituted with $C_{1-6}$alkyl (e.g. 2-methyl-4-thiazolyl).

Preferred embodiments of the invention are compounds of formula (I) or any of the subgroups of compounds of formula (I) wherein $R^{10}$ is hydrogen, $C_{1-6}$alkoxy (e.g. methoxy) or halo.

Preferred embodiments of the invention are compounds of formula (I) or any of the subgroups of compounds of formula (I) wherein one of $R^9$ and $R^{10}$ is halo (in particular fluoro) or trifluoromethyl. Other preferred embodiments are those wherein one of $R^9$ is halo (in particular fluoro) or trifluoromethyl and $R^{10}$ is hydrogen.

Preferred embodiments of the invention are compounds of formula (I) or any of the subgroups of compounds of formula (I) wherein $R^8$ is a radical of formula:

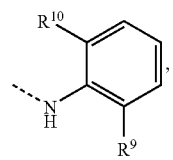

wherein $R^9$ is cyano or methyl and $R^{10}$ is hydrogen or methoxy; or wherein $R^9$ is cyano or methoxy and $R^{10}$ is hydrogen.

Other preferred embodiments of the invention are compounds of formula (I) or any of the subgroups of compounds of formula (I) wherein $R^8$ is a radical of formula:

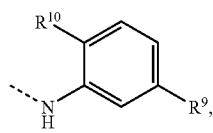

or of formula:

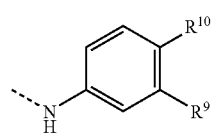

or of formula:

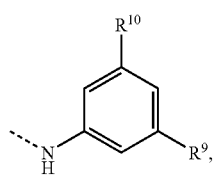

wherein either or both of the following (a) or (b) apply:
(a) $R^9$ is cyano, $C_{1-6}$alkyloxycarbonyl, mono- and di($C_{1-6}$alkylamino), halo, amino, $C_{1-6}$alkoxy, aryloxy, $C_{1-6}$alkyl, Het; or wherein $R^9$ is cyano, $C_{1-6}$alkyloxycarbonyl (e.g. methoxycarbonyl), mono($C_{1-6}$alkylamino) (e.g. methylamino), halo (e.g. chloro), $C_{1-6}$alkoxy (e.g. methoxy), phenoxy, $C_{1-6}$alkyl (e.g. methyl), thiazolyl optionally substituted with $C_{1-6}$alkyl (e.g. 2-methyl-4-thiazolyl);
(b) $R^{10}$ is hydrogen, $C_{1-6}$alkoxy (e.g. methoxy) or halo.

Embodiments of the invention are compounds of formula (I) or any of the subgroups of compounds of formula (I) wherein the group

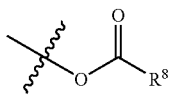

is a group:

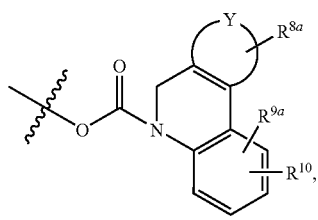

which has the following structure:

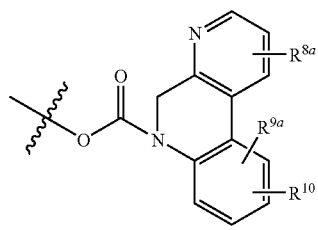

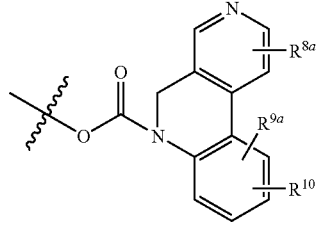

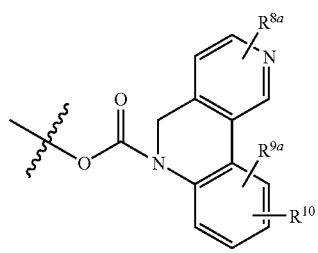

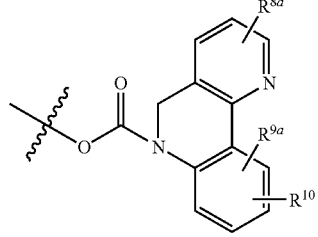

-continued

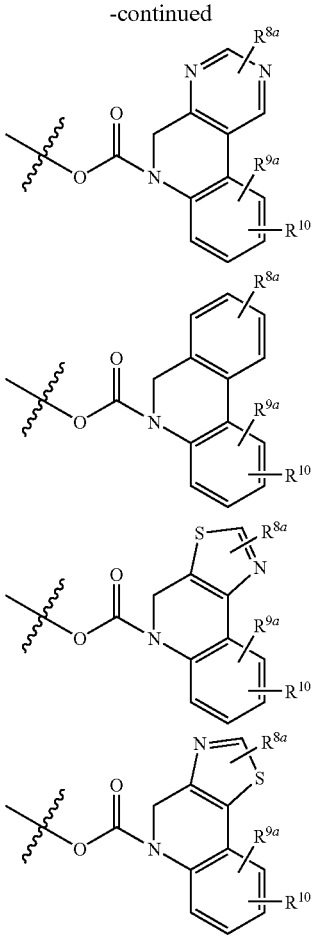

Embodiments of the invention are compounds of formula (I) or any of the subgroups of compounds of formula (I) wherein the group

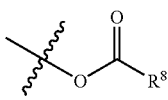

is as in the previous paragraph and $R^{8a}$, $R^{9a}$ and $R^{10}$, or one of $R^{8a}$, $R^9$ and $R^{10}$ are in particular: $R^{8a}$, $R^{9a}$ independently are hydrogen, $C_{1-6}$alkyl (e.g. methyl, ethyl or isopropyl); $C_{1-6}$alkoxy (e.g. methoxy, ethoxy or isopropoxy); aryloxy; Het-O—; cyano; or $R^{10}$ is hydrogen, $C_{1-6}$alkoxy (e.g. methoxy, ethoxy or isopropoxy) or aryloxy (e.g. phenoxy or 4-methoxy-phenoxy);

$R^{8a}$, $R^{9a}$ independently are hydrogen; $C_{1-6}$alkyl (e.g. methyl, ethyl or isopropyl); $C_{1-6}$alkoxy (e.g. methoxy, ethoxy or isopropoxy); cyano; or $R^{10}$ is hydrogen, $C_{1-6}$alkoxy (e.g. methoxy, ethoxy or isopropoxy).

Embodiments of the invention are compounds of formula (I) or any of the subgroups of compounds of formula (I) wherein $R^8$ is hydrogen.

In the previous paragraph, aryl and Het are as specified above or herein after, in particular aryl is phenyl optionally substituted with $C_{1-6}$alkoxy (e.g. with methoxy, ethoxy or isopropoxy), more in particular 4-substituted phenyl; and Het in particular is pyridyl or pyrimidinyl.

Preferred embodiments of the invention are compounds of formula (I) or any of the subgroups of compounds of formula (I) wherein one of $R^9$ is hydrogen, methoxy or cyano.

The compounds of formula (I) consist of three building blocks P1, P2, P3. Building block P1 further contains a P1' tail. The carbonyl group marked with an asterisk in compound (I-i) below may be part of either building block P2 or of building block P3. For reasons of chemistry, building block P2 of the compounds of formula (I) wherein X is C incorporates the carbonyl group attached to the position 1'.

The linking of building blocks P1 with P2, P2 with P3, and P1 with P1' (when $R^1$ is —NH—SO$_2$R$^2$) involves forming an amide bond. The linking of blocks P1 and P3 involves double bond formation. The linking of building blocks P1, P2 and P3 to prepare compounds (I-i) or (I-j) can be done in any given sequence. One of the steps involves a cyclization whereby the macrocycle is formed.

Represented herebelow are compounds (I-i) which are compounds of formula (I) wherein carbon atoms C7 and C8 are linked by a double bond, and compounds (I-j) which are compounds of formula (I) wherein carbon atoms C7 and C8 are linked by a single bond. The compounds of formula (I-j) can be prepared from the corresponding compounds of formula (I-i) by reducing the double bond in the macrocycle.

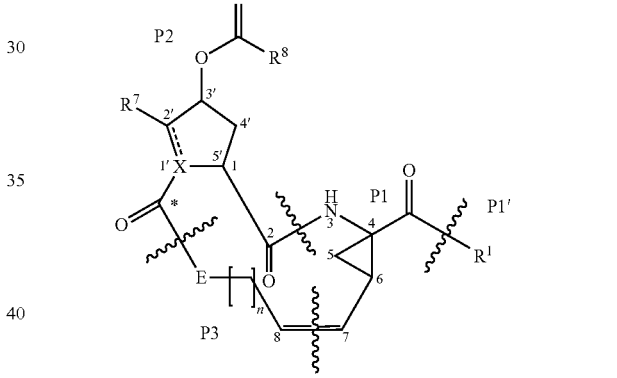

(I-i)

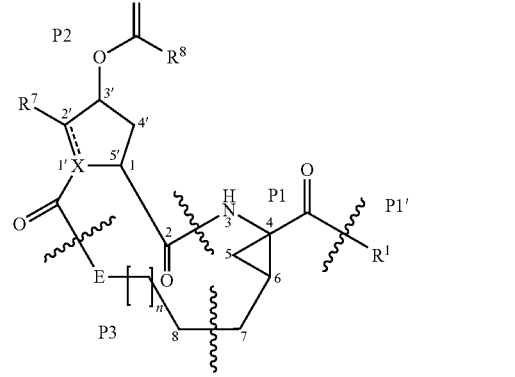

(I-j)

The synthesis procedures described hereinafter are meant to be applicable for as well the racemates, stereochemically pure intermediates or end products, or any stereoisomeric mixtures. The racemates or stereochemical mixtures may be separated into stereoisomeric forms at any stage of the synthesis procedures. In one embodiment, the intermediates and end products have the stereochemistry specified above in the compounds of formula (I-a) and (I-b).

In the following description, $R^{11}$ represents a radical

In one embodiment, compounds (I-i) are prepared by first forming the amide bonds and subsequent forming the double bond linkage between P3 and P1 with concomitant cyclization to the macrocycle.

In one embodiment, compounds (I) wherein the bond between $C_7$ and $C_8$ is a double bond, which are compounds of formula (I-i), as defined above, may be prepared as outlined in the following reaction scheme:

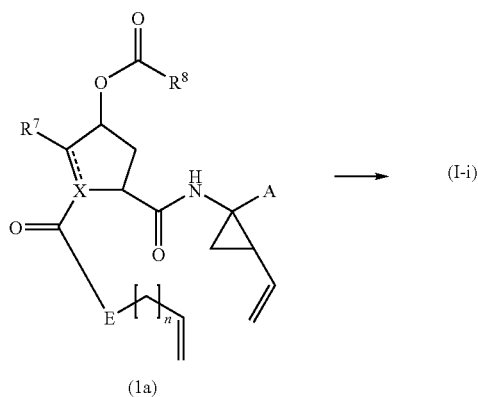

(1a)

Formation of the macrocycle can be carried out via an olefin metathesis reaction in the presence of a suitable metal catalyst such as e.g. the Ru-based catalyst reported by Miller, S. J., Blackwell, H. E., Grubbs, R. H. J. Am. Chem. Soc. 118, (1996), 9606-9614; Kingsbury, J. S., Harrity, J. P. A., Bonitatebus, P. J., Hoveyda, A. H., J. Am. Chem. Soc. 121, (1999), 791-799; and Huang et al., J. Am. Chem. Soc. 121, (1999), 2674-2678; for example a Hoveyda-Grubbs catalyst.

Air-stable ruthenium catalysts such as bis(tricyclohexylphosphine)-3-phenyl-1H-inden-1-ylidene ruthenium chloride (Neolyst M1®) or bis(tricyclohexylphosphine)-[(phenyl-thio)methylene]ruthenium (IV) dichloride can be used. Other catalysts that can be used are Grubbs first and second generation catalysts, i.e. benzylidene-bis(tricyclohexylphosphine)dichlororuthenium and (1,3-bis-(2,4,6-trimethylphenyl)-2-imidazolidinylidene)dichloro(phenylmethylene)(tricyclohexylphosphine)ruthenium, respectively. Of particular interest are the Hoveyda-Grubbs first and second generation catalysts, which are dichloro(o-isopropoxyphenylmethylene)(tricyclohexylphosphine)-ruthenium(II) and 1,3-bis-(2,4,6-trimethylphenyl)-2-imidazolidinylidene) dichloro-(o-isopropoxyphenylmethylene)ruthenium respectively. Also other catalysts containing other transition metals such as Mo can be used for this reaction.

The metathesis reactions may be conducted in a suitable solvent such as for example ethers, e.g. THF, dioxane; halogenated hydrocarbons, e.g. dichoromethane, $CHCl_3$, 1,2-dichloroethane and the like, hydrocarbons, e.g. toluene. In a preferred embodiment, the metathesis reaction is conducted in toluene. These reactions are conducted at increased temperatures under nitrogen atmosphere.

Compounds of formula (I) wherein the link between C7 and C8 in the macrocycle is a single bond, i.e. compounds of formula (I-j), can be prepared from the compounds of formula (I-i) by a reduction of the C7-C8 double bond in the compounds of formula (I-i). This reduction may be conducted by catalytic hydrogenation with hydrogen in the presence of a noble metal catalyst such as, for example, Pt, Pd, Rh, Ru or Raney nickel. Of interest is Rh on alumina. The hydrogenation reaction preferably is conducted in a solvent such as, e.g. an alcohol such as methanol, ethanol, or an ether such as THF, or mixtures thereof. Water can also be added to these solvents or solvent mixtures.

The A group can be connected to the P1 building block at any stage of the synthesis, i.e. before or after the cyclization, or before or after the cyclization and reduction as described herein above. The compounds of formula (I) wherein A represents —CO—$NHSO_2R^2$, said compounds being represented by formula (I-k-1), can be prepared by linking the A group to P1 by forming an amide bond between both moieties. Similarly, the compounds of formula (I) wherein $R^1$ represents —C(=O)$OR^1$, i.e. compounds (I-k-2), can be prepared by linking the $R^1$ group to P1 by forming an ester bond. In one embodiment, the —C(=O)$OR^1$ groups are introduced in the last step of the synthesis of the compounds (I) as outlined in the following reaction schemes wherein G represents a group:

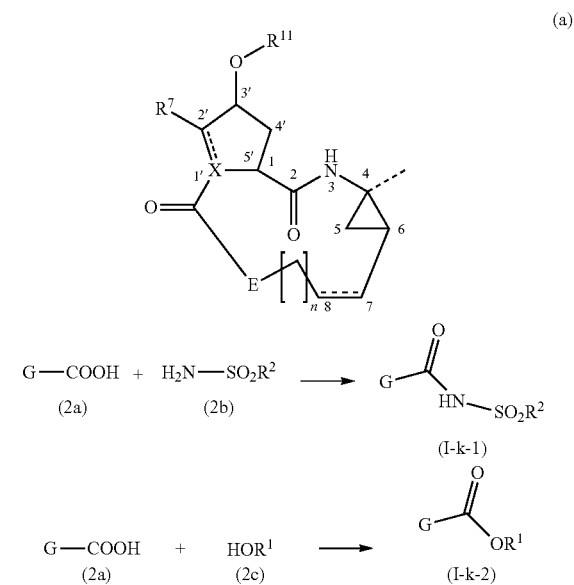

Intermediate (2a) can be coupled with sulfonamide (2b) by an amide forming reaction such as any of the procedures for the formation of an amide bond described hereinafter. In particular, (2a) may be treated with a coupling agent, for example N,N'-carbonyl-diimidazole (CDI), EEDQ, IIDQ, EDCI or benzotriazol-1-yl-oxy-tris-pyrrolidino-phosphonium hexafluorophosphate (commercially available as PyBOP®), in a solvent such as an ether, e.g. THF, or a halogenated hydrocarbon, e.g. dichloromethane, chloroform, dichloroethane, and reacted with the desired sulfonamide (2b), preferably after reacting (2a) with the coupling agent. The reactions of (2a) with (2b) preferably are conducted in the presence of a base, for example a trialkylamine such as triethylamine or diisopropylethylamine, or 1,8-diazabicyclo [5.4.0]undec-7-ene (DBU). Intermediate (2a) can also be converted into an activated form, e.g. an activated form of general formula G-CO—Z, wherein Z represents halo, or the rest of an active ester, e.g. Z is an aryloxy group such as phenoxy, p.nitrophenoxy, pentafluorophenoxy, trichlorophenoxy, pentachlorophenoxy and the like; or Z can be the rest of a mixed anhydride. In one embodiment, G-CO—Z is an acid chloride (G-CO—Cl) or a mixed acid anhydride (G-CO—O—CO—R or G-CO—O—CO—OR, R in the latter being e.g. $C_{1-4}$alkyl, such as methyl, ethyl, propyl, i.propyl, butyl, t.butyl, i.butyl, or benzyl). The activated form G-CO—Z is reacted with the sulfonamide (2b).

The compounds of formula (I) wherein A represents —C(=O)—NH—P(=O)(OR$^{4a}$)(R$^{4b}$), said compounds being represented by formula (I-k-3), can be prepared by forming an amide bond between intermediate (2a) and phosphoramidate (2d), following the procedures for the formation of an amide bond described hereinafter. In particular, (2a) may be treated with a coupling agent in an appropriate solvent followed by reaction with phosphoramidate (2d), preferably in the presence of a base such as sodium hydride, preferably after reacting (2a) with the coupling agent. Intermediate (2a) can also be converted into an activated form, e.g. an activated form of general formula G-CO—Z, wherein Z represents halo, or the rest of an active ester, e.g. Z is an aryloxy group such as phenoxy, p-nitrophenoxy, pentafluorophenoxy, trichlorophenoxy, pentachlorophenoxy and the like; or Z can be the rest of a mixed anhydride. In one embodiment, G-CO—Z is an acid chloride (G-CO—Cl) or a mixed acid anhydride (G-CO—O—CO—R or G-CO—O—CO—OR, R in the latter being e.g. $C_{1-4}$alkyl, such as methyl, ethyl, propyl, i.propyl, butyl, t.butyl, i.butyl, or benzyl). The activated form G-CO—Z is reacted with the desired (2b). The coupling agent, solvent and base may be as described hereinafter in the general description of the preparation of amide bonds.

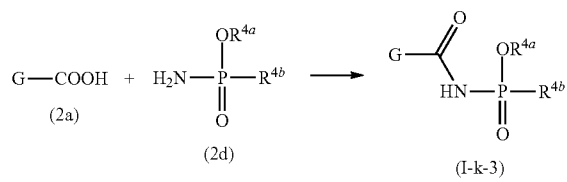

The activation of the carboxylic acid in (2a) as described in the above reactions may lead to an internal cyclization reaction to an azalactone intermediate of formula

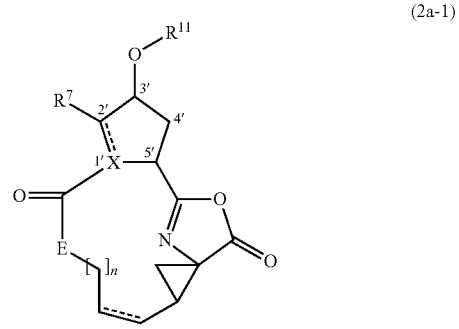

wherein X, E, R$^7$, R$^{11}$ and n are as specified above and wherein the stereogenic centers may have the stereochemical configuration as specified above, for example as in (I-a) or (I-b). The intermediates (2a-1) can be isolated from the reaction mixture, using conventional methodology, and the isolated intermediate (2a-1) is then reacted with (2b), or the reaction mixture containing (2a-1) can be reacted further with (2b) or (2d) without isolation of (2a-1). In one embodiment, where the reaction with the coupling agent is conducted in a water-immiscible solvent, the reaction mixture containing (2a-1) may be washed with water or with slightly basic water in order to remove all water-soluble side products. The thus obtained washed solution may then be reacted with (2b) or (2d) without additional purification steps. The isolation of intermediates (2a-1) on the other hand may provide certain advantages in that the isolated product, after optional further purification, may be reacted with (2b) or (2d), giving rise to less side products and an easier work-up of the reaction.

Intermediate (2a) can be coupled with the alcohol (2c) by an ester forming reaction. For example, (2a) and (2c) are reacted together with removal of water either physically, e.g. by azeotropical water removal, or chemically by using a dehydrating agent. Intermediate (2a) can also be converted into an activated form G-CO—Z, such as the activated forms mentioned above, and subsequently reacted with the alcohol (2c). The ester forming reactions preferably are conducted in the presence of a base such as an alkali metal carbonate or hydrogen carbonate, e.g. sodium or potassium hydrogen carbonate, or a tertairy amine such as the amines mentioned herein in relation to the amide forming reactions, in particular a trialkylamine, e.g. triethylamine. Solvents that can be used in the ester forming reactions comprise ethers such as THF; halogenated hydrocarbons such as dichoromethane, $CH_2Cl_2$; hydrocarbons such as toluene; polar aprotic solvents such as DMF, DMSO, DMA; and the like solvents.

The compounds of formula (I) wherein E is NH, said compounds being represented by (I-l), can also be prepared by removal of a protecting group PG, from a corresponding nitrogen-protected intermediate (3a), as in the following reaction scheme. The protecting group PG in particular is any of the nitrogen protecting groups mentioned hereinafter and can be removed using procedures also mentioned hereinafter:

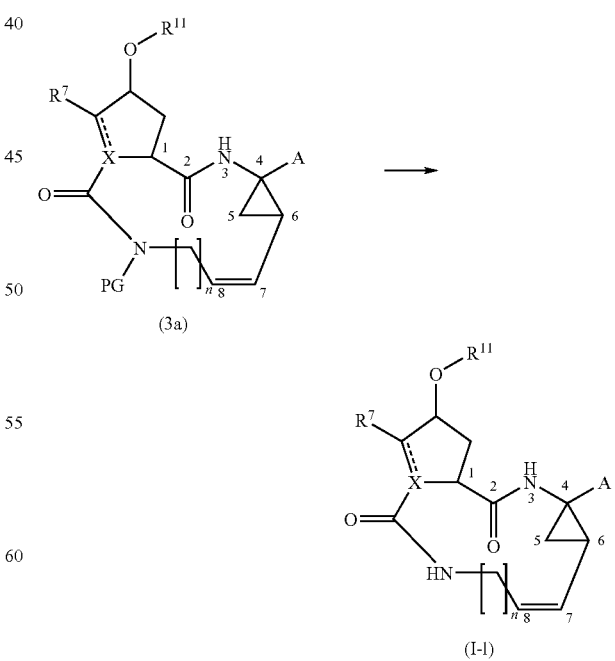

The starting materials (3a) in the above reaction can be prepared following the procedures for the preparation of compounds of formula (I), but using intermediates wherein the group $R^5$ is a N-protecting group PG as defined herein.

The compounds of formula (I) can also be prepared by reacting an intermediate (4a) with an amine (4b-1), (4b-2) or (4b-3) in the presence of a carbamate forming reagent as outlined in the following reaction scheme wherein the various radicals have the meanings specified above:

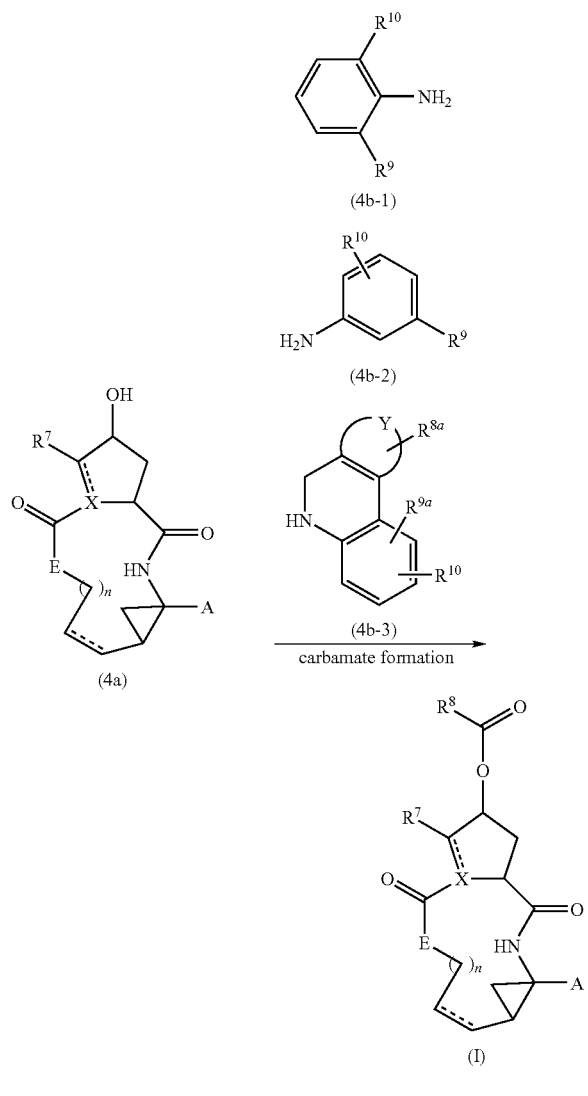

The reaction of intermediates (4a) with the carbamate forming reagent is conducted in the same solvents and bases as those used for the amide bond formation as described hereinafter.

Carbamate forming reactions may be conducted using a variety of methods, in particular by reaction of amines with alkyl chloroformates; by reaction of alcohols with carbamoyl chlorides or isocyanates; via reactions involving metal complexes or acyl transfer agents. See for example, Greene, T. W. and Wuts, P. G. M., "Protective Groups in Organic Synthesis"; 1999; Wiley and Sons, p. 309-348. Carbon monoxide and certain metal catalysts can be used to synthesize carbamates from several starting compounds, including amines. Metals such as palladium, iridium, uranium, and platinum may be used as catalysts. Methods using carbon dioxide for synthesis of carbamates that have been also been reported, can also be used (see for example, Yoshida, Y., et al., Bull. Chem. Soc. Japan 1989, 62, 1534; and Aresta, M., et al., Tetrahedron, 1991, 47, 9489).

One approach for the preparation of carbamates involves the use of intermediates

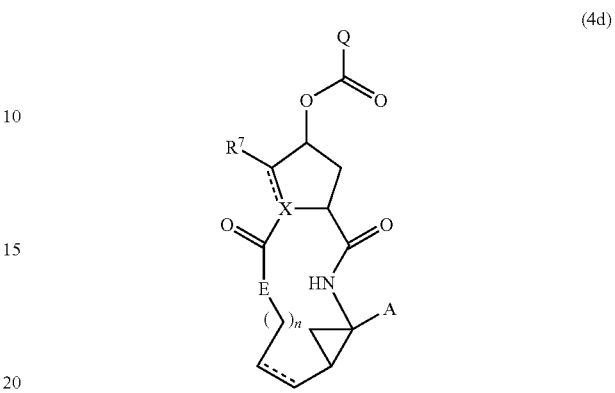

wherein Q is leaving group such as halo, in particular chloro and bromo, or a group used in active esters for amide bond formation, such as those mentioned above, for example phenoxy or substituted phenoxy such as p.chloro and p.nitrophenoxy, trichlorophenoxy, pentachlorophenoxy, N-hydroxy-succinimidyl, and the like. Intermediates (4d) can be derived from alcohols (4a) and phosgene, thus forming a chloroformate, or by transferring the chloro in the latter to intermediates (5a) which are intermediates of formula (4d) wherein Q is $Q^1$. In this and the following reaction procedures, $Q^1$ represents any of the active ester moieties such as those mentioned above. Intermediates (4d) are reacted with the amines (4b-1), (4b-2), or (4b-3) thus obtaining compounds (I).

Intermediates (4e), which are intermediates (4d) wherein Q is $Q^1$, can also be prepared by reacting the alcohol (4a) with carbonates $Q^1$-CO-$Q^1$ such as e.g. bisphenol, bis-(substituted phenol) or bis N-hydroxy-succinimidyl carbonates:

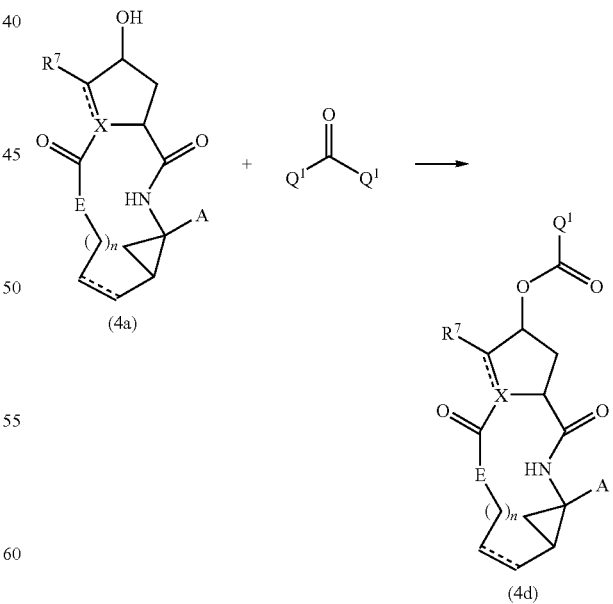

The above reactions to prepare intermediates (4d) may be conducted in the presence of the bases and solvents mentioned hereinafter for the synthesis of amide bonds, in particular triethylamine as base and dichloromethane as solvent.

Alternatively, in order to prepare the compounds of formula (I), first an amide bond between building blocks P2 and P1 is formed, followed by coupling of the P3 building block to the P1 moiety in P1-P2, and a subsequent carbamate or ester bond formation between P3 and the P2 moiety in P2-P1-P3 with concomitant ring closure.

Yet another alternative synthetic methodology is the formation of an amide bond between building blocks P2 and P3, followed by the coupling of building block P1 to the P3 moiety in P3-P2, and a last amide bond formation between P1 and P2 in P1-P3-P2 with concomitant ring closure.

Building blocks P1 and P3 can be linked to a P1-P3 sequence. If desired, the double bond linking P1 and P3 may be reduced. The thus formed P1-P3 sequence, either reduced or not, can be coupled to building block P2 and the thus forming sequence P1-P3-P2 subsequently cyclized, by forming an amide bond.

Building blocks P1 and P3 in any of the previous approaches can be linked via double bond formation, e.g. by the olefin metathesis reaction described hereinafter, or a Wittig type reaction. If desired, the thus formed double bond can be reduced, similarly as described above for the conversion of (I-i) to (I-j). The double bond can also be reduced at a later stage, i.e. after addition of a third building block, or after formation of the macrocycle. Building blocks P2 and P1 are linked by amide bond formation and P3 and P2 are linked by carbamate or ester formation.

The tail P1' can be linked to the P1 building block at any stage of the synthesis of the compounds of formula (I), for example before or after coupling the building blocks P2 and P1; before or after coupling the P3 building block to P1; or before or after ring closure.

The individual building blocks can first be prepared and subsequently coupled together or alternatively, precursors of the building blocks can be coupled together and modified at a later stage to the desired molecular composition.

The functionalities in each of the building blocks may be protected to avoid side reactions.

The formation of amide bonds can be carried out using standard procedures such as those used for coupling amino acids in peptide synthesis. The latter involves the dehydrative coupling of a carboxyl group of one reactant with an amino group of the other reactant to form a linking amide bond. The amide bond formation may be performed by reacting the starting materials in the presence of a coupling agent or by converting the carboxyl functionality into an active form such as an active ester, mixed anhydride or a carboxyl acid chloride or bromide. General descriptions of such coupling reactions and the reagents used therein can be found in general textbooks on peptide chemistry, for example, M. Bodanszky, "Peptide Chemistry", 2nd rev. ed., Springer-Verlag, Berlin, Germany, (1993).

Examples of coupling reactions with amide bond formation include the azide method, mixed carbonic-carboxylic acid anhydride (isobutyl chloroformate) method, the carbodiimide (dicyclohexylcarbodiimide, diisopropylcarbodiimide, or water-soluble carbodiimide such as N-ethyl-N'-[(3-dimethylamino)propyl]carbodiimide) method, the active ester method (e.g. p-nitrophenyl, p-chlorophenyl, trichlorophenyl, pentachloro-phenyl, pentafluorophenyl, N-hydroxysuccinic imido and the like esters), the Woodward reagent K-method, the 1,1-carbonyldiimidazole (CDI or N,N'-carbonyl-diimidazole) method, the phosphorus reagents or oxidation-reduction methods. Some of these methods can be enhanced by adding suitable catalysts, e.g. in the carbodiimide method by adding 1-hydroxybenzotriazole, DBU (1,8-diazabicyclo[5.4.0]undec-7-ene), or 4-DMAP. Further coupling agents are (benzotriazol-1-yloxy)tris-(dimethylamino)phosphonium hexafluorophosphate, either by itself or in the presence of 1-hydroxy-benzotriazole or 4-DMAP; or 2-(1H-benzotriazol-1-yl)-N,N,N',N'-tetra-methyluronium tetrafluoroborate, or O-(7-azabenzotriazol-1-yl)-N,N,N',N'-tetramethyluronium hexafluorophosphate. These coupling reactions can be performed in either solution (liquid phase) or solid phase.

A preferred amide bond formation is performed employing N-ethyloxycarbonyl-2-ethyloxy-1,2-dihydroquinoline (EEDQ) or N-isobutyloxy-carbonyl-2-isobutyloxy-1,2-dihydroquinoline (IIDQ). Unlike the classical anhydride procedure, EEDQ and IIDQ do not require base nor low reaction temperatures. Typically, the procedure involves reacting equimolar amounts of the carboxyl and amine components in an organic solvent (a wide variety of solvents can be used). Then EEDQ or IIDQ is added in excess and the mixture is allowed to stir at room temperature.

The coupling reactions preferably are conducted in an inert solvent, such as halogenated hydrocarbons, e.g. dichloromethane, chloroform, dipolar aprotic solvents such as acetonitrile, dimethylformamide, dimethylacetamide, DMSO, HMPT, ethers such as tetrahydrofuran (THF).

In many instances the coupling reactions are done in the presence of a suitable base such as a tertiary amine, e.g. triethylamine, diisopropylethylamine (DIPEA), N-methylmorpholine, N-methylpyrrolidine, 4-DMAP or 1,8-diazabicycle[5.4.0]undec-7-ene (DBU). The reaction temperature may range between 0° C. and 50° C. and the reaction time may range between 15 min and 24 h.

The functional groups in the building blocks that are linked together may be protected to avoid formation of undesired bonds. Appropriate protecting groups that can be used are listed for example in Greene, "Protective Groups in Organic Chemistry", John Wiley & Sons, New York (1999) and "The Peptides: Analysis, Synthesis, Biology", Vol. 3, Academic Press, New York (1987).

Carboxyl groups can be protected as an ester that can be cleaved off to give the carboxylic acid. Protecting groups that can be used include 1) alkyl esters such as methyl, trimethylsilyl and tert-butyl; 2) arylalkyl esters such as benzyl and substituted benzyl; or 3) esters that can be cleaved by a mild base or mild reductive means such as trichloroethyl and phenacyl esters.

Amino groups can be protected by a variety of N-protecting groups, such as:

1) acyl groups such as formyl, trifluoroacetyl, phthalyl, and p-toluenesulfonyl;
2) aromatic carbamate groups such as benzyloxycarbonyl (Cbz or Z) and substituted benzyloxycarbonyls, and 9-fluorenylmethyloxycarbonyl (Fmoc);
3) aliphatic carbamate groups such as tert-butyloxycarbonyl (Boc), ethoxycarbonyl, diisopropylmethoxy-carbonyl, and allyloxycarbonyl;
4) cyclic alkyl carbamate groups such as cyclopentyloxycarbonyl and adamantyloxycarbonyl;
5) alkyl groups such as triphenylmethyl, benzyl or substituted benzyl such as 4-methoxybenzyl;
6) trialkylsilyl such as trimethylsilyl or t.Bu dimethylsilyl; and
7) thiol containing groups such as phenylthiocarbonyl and dithiasuccinoyl. Interesting amino protecting groups are Boc and Fmoc.

Preferably the amino protecting group is cleaved off prior to the next coupling step. Removal of N-protecting groups can be done following art-known procedures. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethyl-formamide. When the Fmoc group is used, the reagents of choice are piperidine or substituted piperidine in dimethylformamide, but any secondary amine can be used. The deprotection is carried out at a temperature between 0° C. and room temperature, usually around 15-25° C., or 20-22° C.

Other functional groups that can interfere in the coupling reactions of the building blocks may also be protected. For example hydroxyl groups may be protected as benzyl or substituted benzyl ethers, e.g. 4-methoxybenzyl ether, benzoyl or substituted benzoyl esters, e.g. 4-nitrobenzoyl ester, or with trialkylsilyl groups (e.g. trimethylsilyl or tert-butyldimethylsilyl).

Further amino groups may be protected by protecting groups that can be cleaved off selectively. For example, when Boc is used as the α-amino protecting group, the following side chain protecting groups are suitable: p-toluenesulfonyl (tosyl) moieties can be used to protect further amino groups; benzyl (Bn) ethers can be used to protect hydroxy groups; and benzyl esters can be used to protect further carboxyl groups. Or when Fmoc is chosen for the α-amino protection, usually tert-butyl based protecting groups are acceptable. For instance, Boc can be used for further amino groups; tert-butyl ethers for hydroxyl groups; and tert-butyl esters for further carboxyl groups.

Any of the protecting groups may be removed at any stage of the synthesis procedure but preferably, the protecting groups of any of the functionalities not involved in the reaction steps are removed after completion of the build-up of the macrocycle. Removal of the protecting groups can be done in whatever manner is dictated by the choice of protecting groups, which manners are well known to those skilled in the art.

The intermediates of formula (1a) wherein X is N, said intermediates being represented by formula (1a-1), may be prepared starting from intermediates (5a) which are reacted with an alkenamine (5b) in the presence of a carbonyl introducing agent as outlined in the following reaction scheme.

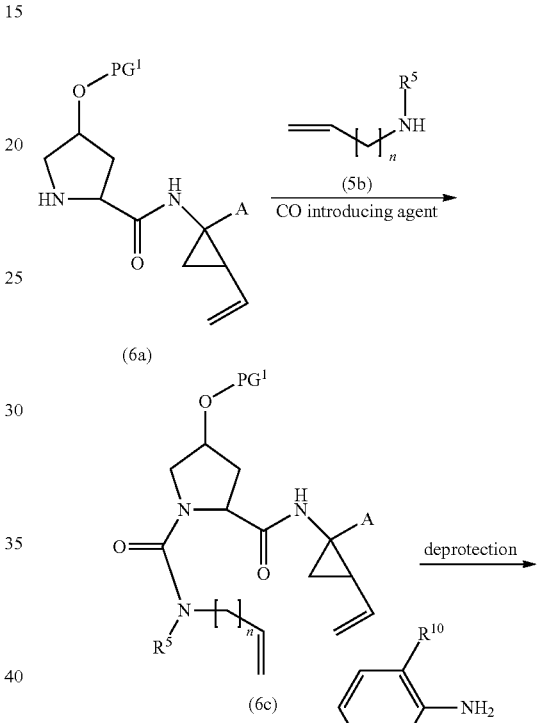

Carbonyl (CO) introducing agents include phosgene, or phosgene derivatives such as carbonyl diimidazole (CDI), and the like. In one embodiment (5a) is reacted with the CO introducing agent in the presence of a suitable base and a solvent, which can be the bases and solvents used in the amide forming reactions as described above. In a particular embodiment, the base is a hydrogencarbonate, e.g. $NaHCO_3$, or a tertiary amine such as triethylamine and the like, and the solvent is an ether or halogenated hydrocarbon, e.g. THF, $CH_2Cl_2$, $CHCl_3$, and the like. Thereafter, the amine (5b) is added thereby obtaining intermediates (1a-1) as in the above scheme. An alternative route using similar reaction conditions involves first reacting the CO introducing agent with the alkenamine (5b) and then reacting the thus formed intermediate with (5a).

The intermediates (1a-1) can alternatively be prepared as follows:

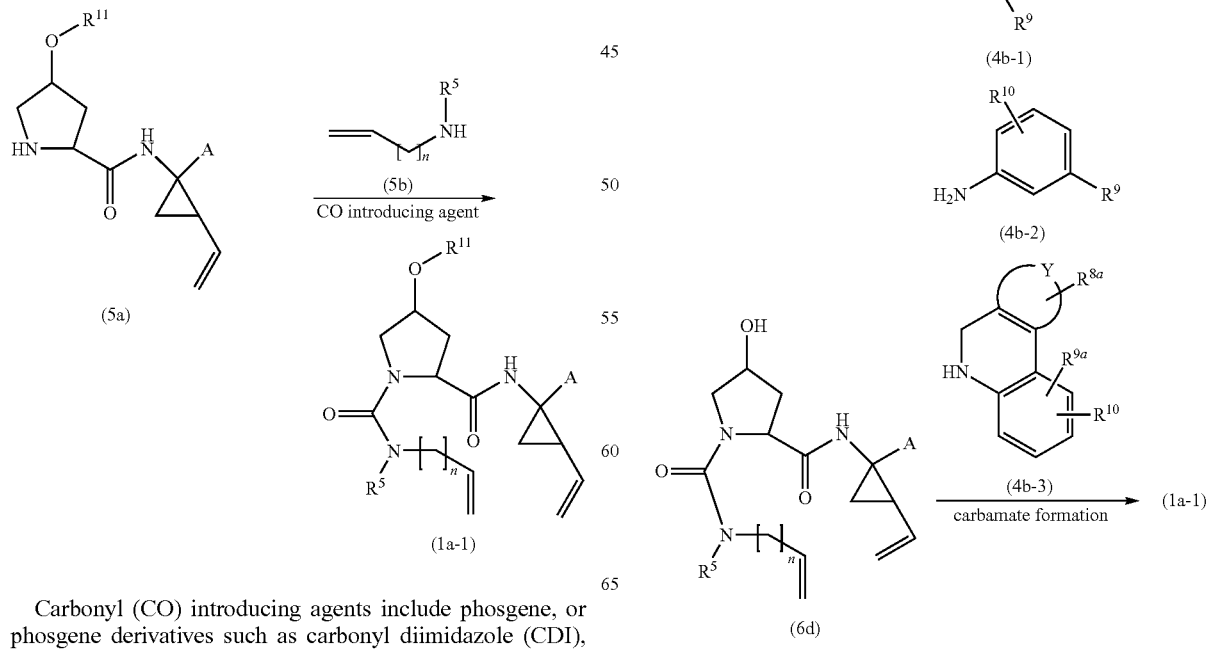

PG$^1$ is an O-protecting group, which can be any of the groups mentioned herein and in particular is a benzoyl or substituted benzoyl group such as 4-nitrobenzoyl. In the latter instance this group can be removed by reaction with a an alkali metal hydroxide (LiOH, NaOH, KOH), in particular where PG$^1$ is 4-nitrobenzoyl, with LiOH, in an aqueous medium comprising water and a water-soluble organic solvent such as an alkanol (methanol, ethanol) and THF.

Intermediates (6a) are reacted with an alkenamine (5b) in the presence of a carbonyl introducing agent, similar as described above, and this reaction yields intermediates (6c). These are deprotected, in particular using the reaction conditions mentioned above. The resulting alcohol (6d) is reacted with intermediates (4b-1), (4b-2), or (4b-3) as described above for the reaction of (4a) with (4b-1), (4b-2), or (4b-3), and this reaction results in intermediates (1a-1).

The intermediates of formula (1a) wherein X is C, said intermediates being represented by formula (1a-2), may be prepared by an amide forming reaction starting from intermediates (7a) which are reacted with an alkenamine (5b) as shown in the following reaction scheme, using reaction conditions for preparing amides such as those described above.

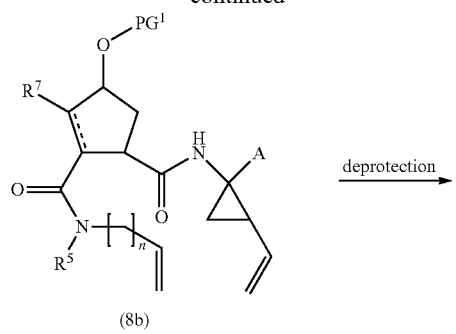

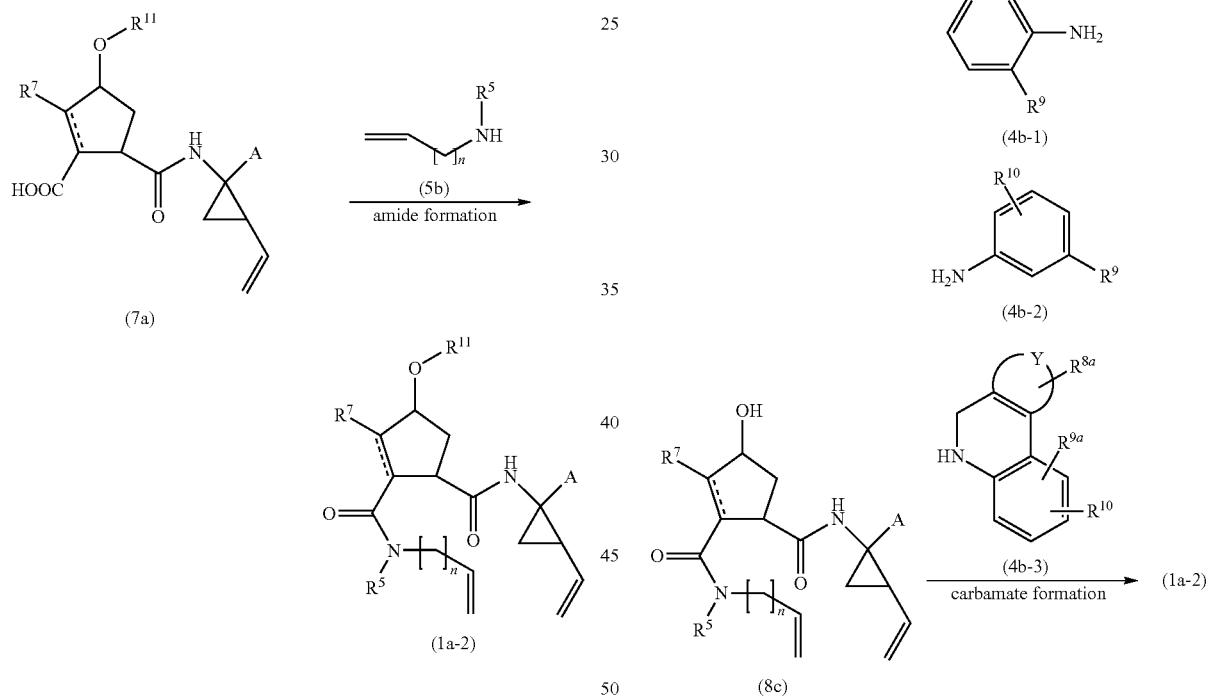

The intermediates (1a-2) can alternatively be prepared as follows:

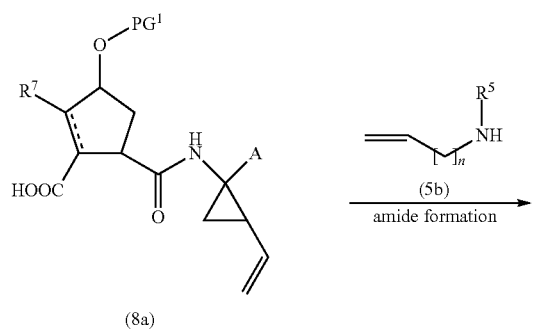

PG$^1$ is an O-protecting group as described above. The same reaction conditions as described above may be used: amide formation as described above, removal of PG$^1$ as in the description of the protecting groups and introduction of —OR$^{11}$ as in the reactions of (4a) with the amines (4b-1), (4b-2), or (4b-3).

The intermediates of formula (2a) may be prepared by first cyclizing the open amide (9a) to a macrocyclic ester (9b), which in turn is converted to (2a) as follows:

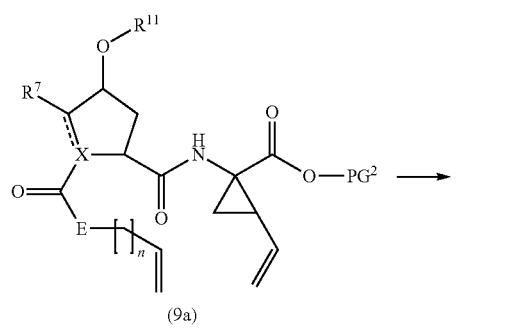

(9a)

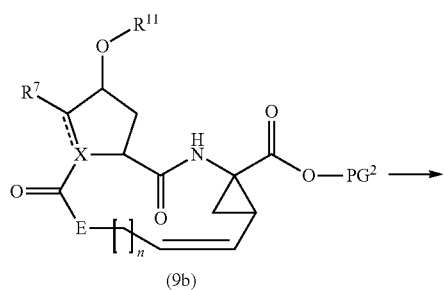

(9b)

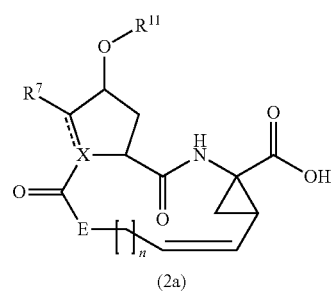

(2a)

PG² is a carboxyl protecting group, e.g. one of the carboxyl protecting groups mentioned above, in particular a C₁₋₄alkyl or benzyl ester, e.g. a methyl, ethyl or t.butyl ester. The reaction of (9a) to (9b) is a metathesis reaction and is conducted as described above. The group PG² is removed following procedures also described above. Where PG² is a C₁₋₄alkyl ester, it is removed by alkaline hydrolysis, e.g. with NaOH or preferably LiOH, in an aqueous solvent, e.g. a C₁₋₄alkanol/water mixture. A benzyl group can be removed by catalytic hydrogenation.

In an alternative synthesis, intermediates (2a) can be prepared as follows:

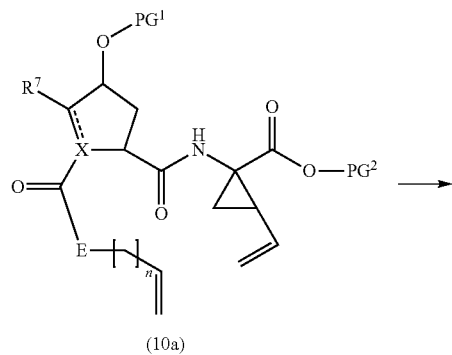

(10a)

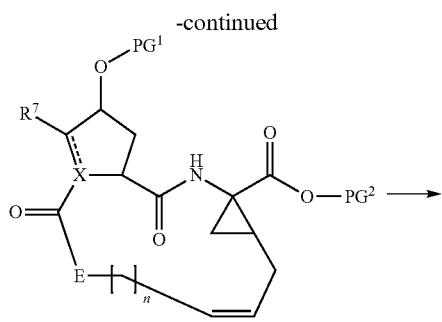

(10b)

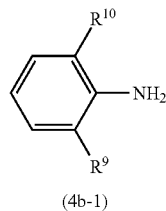

(4b-1)

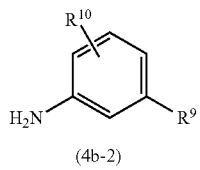

(4b-2)

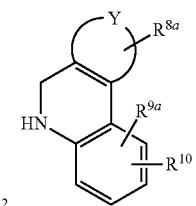

(4b-3)

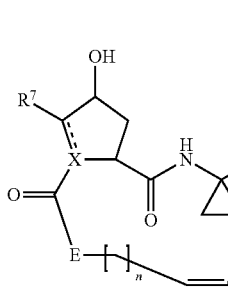

(10c)

(9b) ⟶ (2a)

The PG¹ group is selected such that it is selectively cleavable towards PG². PG² may be e.g. methyl or ethyl esters, which can be removed by treatment with an alkali metal hydroxide in an aqueous medium, in which case PG¹ e.g. is t.butyl or benzyl. PG² may be t.butyl esters removable under weakly acidic conditions or PG¹ may be benzyl ethers removable with strong acid or by catalytic hydrogenation, in the latter two cases PG¹ e.g. is a benzoic ester such as a 4-nitrobenzoic ester.

First, intermediates (10a) are cyclized to the macrocyclic esters (10b), the latter are deprotected by removal of the PG¹ group to (10c), which are reacted with intermediates (4b) in a carbamate forming reaction as described above, followed by removal of carboxyl protecting group PG². The cyclization, deprotection of PG¹ and PG² and the carbamate forming reaction with (4b-1), (4b-2), or (4b-3) are as described above.

The A groups can be introduced at any stage of the synthesis, either as the last step as described above, or earlier, before the macrocycle formation. In the following scheme, the groups A being —CO—NH—SO₂R² or —CO—OR⁵ (which are as specified above) are introduced:

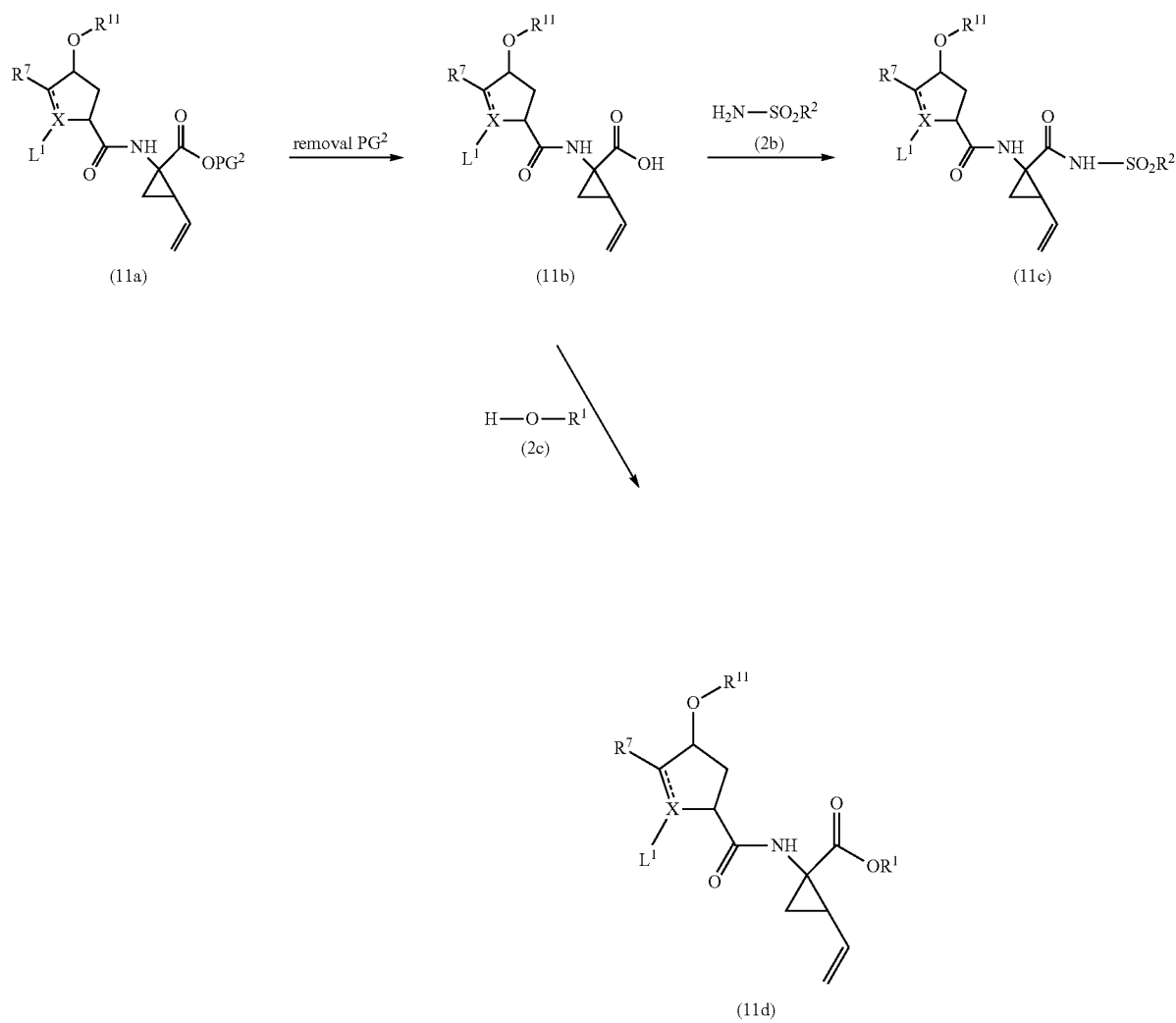

In the above scheme, $PG^2$ is as defined above and $L^1$ is a P3 group

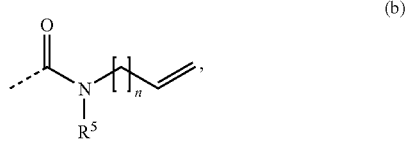

(b)

wherein n and $R^5$ are as defined above and where X is N, $L^1$ may also be a nitrogen-protecting group (PG, as defined above) and where X is C, $L^1$ may also be a group —$COOPG^{2a}$, wherein the group $PG^{2a}$ is a carboxyl protecting group similar as $PG^2$, but wherein $PG^{2a}$ is selectively cleavable towards $PG^2$. In one embodiment $PG^{2a}$ is t.butyl and $PG^2$ is methyl or ethyl.

The intermediates (11c) and (11d) wherein $L^1$ represents a group (b) correspond to the intermediates (1a) and may be processed further as specified above.

Coupling of P1 and P2 Building Blocks

The P1 and P2 building blocks are linked using an amide forming reaction following the procedures described above. The P1 building block may have a carboxyl protecting group $PG^2$ (as in (12b)) or may already be linked to P1' group (as in (12c)). $L^2$ is a N-protecting group (PG), or a group (b), as specified above. $L^3$ is hydroxy, —$OPG^1$ or a group —O—$R^{11}$ as specified above. Where in any of the following reaction schemes $L^3$ is hydroxy, prior to each reaction step, it may be protected as a group —$OPG^1$ and, if desired, subsequently deprotected back to a free hydroxy function. Similarly as described above, the hydroxy function may be converted to a group —O—$R^{11}$.

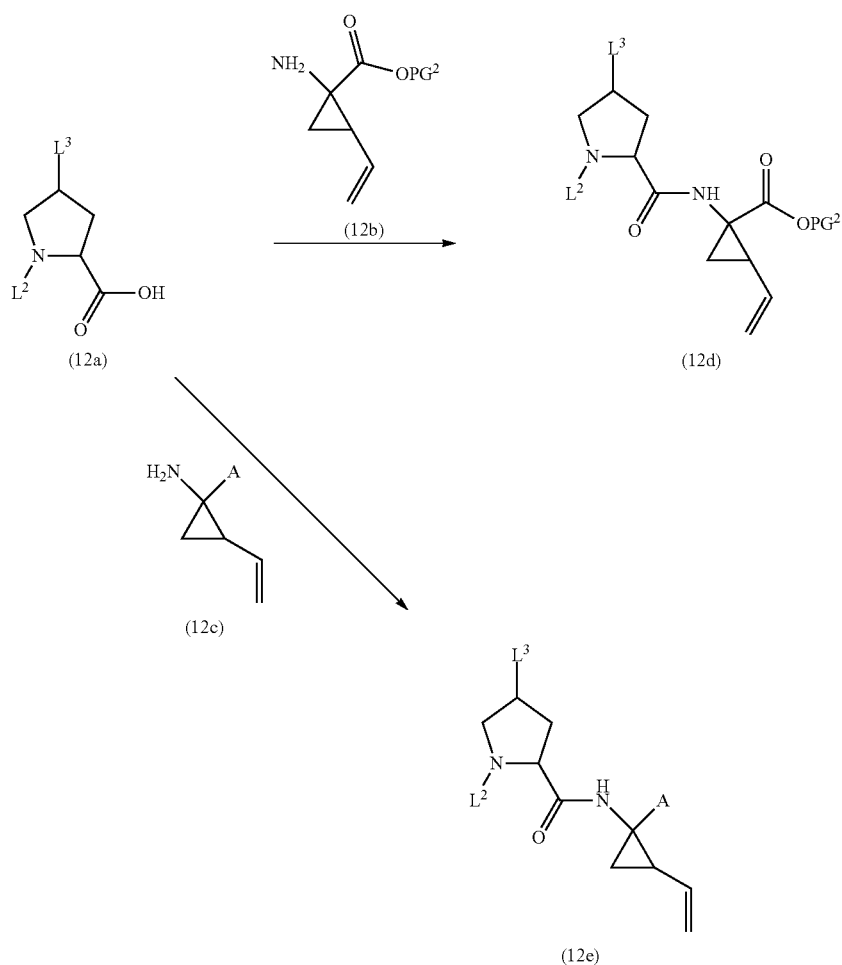

In the procedure of the above scheme, a cyclopropyl amino acid (12b) or (12c) is coupled to the acid function of the P2 building block (12a) with the formation of an amide linkage, following the procedures described above. Intermediates (12d) or (12e) are obtained. Where in the latter $L^2$ is a group (b), the resulting products are P3-P2-P1 sequences encompassing some of the intermediates (11c) or (11d) in the previous reaction scheme. Removal of the acid protecting group in (12d), using the appropriate conditions for the protecting group used, followed by coupling with an sulfonamide $H_2N-SO_2R^2$ (2b), a phosphoramide (2d), or with $HOR^1$ (2c) as described above, again yields the intermediates (12e), wherein -A are amide or ester groups. Where $L^2$ is a N-protecting group, it can be removed yielding intermediates (5a) or (6a). In one embodiment, PG in this reaction is a BOC group and $PG^2$ is methyl or ethyl. Where additionally $L^3$ is hydroxy, the starting material (12a) is Boc-L-hydroxyproline. In a particular embodiment, PG is BOC, $PG^2$ is methyl or ethyl and $L^3$ is $-O-R^{11}$.

In one embodiment, $L^2$ is a group (b) and these reactions involve coupling P1 to P2-P3, which results in the intermediates (1a-1) or (1a) mentioned above. In another embodiment, $L^2$ is a N-protecting group PG, which is as specified above, and the coupling reaction results in intermediates (12d-1) or (12e-1), from which the group PG can be removed, using reaction conditions mentioned above, obtaining intermediates (12-f) or respectively (12g), which encompass intermediates (5a) and (6a) as specified above:

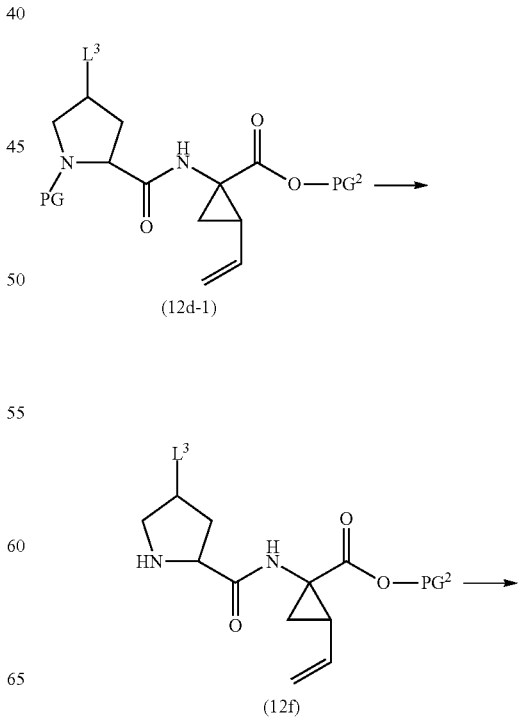

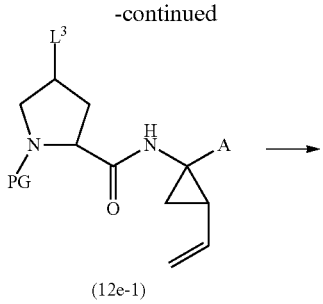

(12e-1)

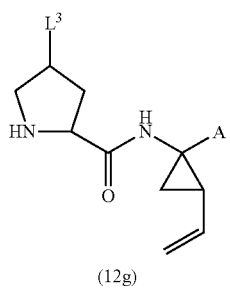

(12g)

In one embodiment, the group $L^3$ in the above schemes represents a group —O—$PG^1$ which can be introduced on a starting material (12a) wherein $L^3$ is hydroxy. In this instance $PG^1$ is chosen such that it is selectively cleavable towards group $L^2$ being PG.

In a similar way, P2 building blocks wherein X is C, which are cyclopentane or cyclopentene derivatives, can be linked to P1 building blocks as outlined in the following scheme wherein A, $R^7$, $L^3$ are as specified above and $PG^2$ and $PG^{2a}$ are carboxyl protecting groups. $PG^{2a}$ typically is chosen such that it is selectively cleavable towards group $PG^2$. Removal of the $PG^{2a}$ group in (13c) yields intermediates (7a) or (8a), which can be reacted with (5b) as described above.

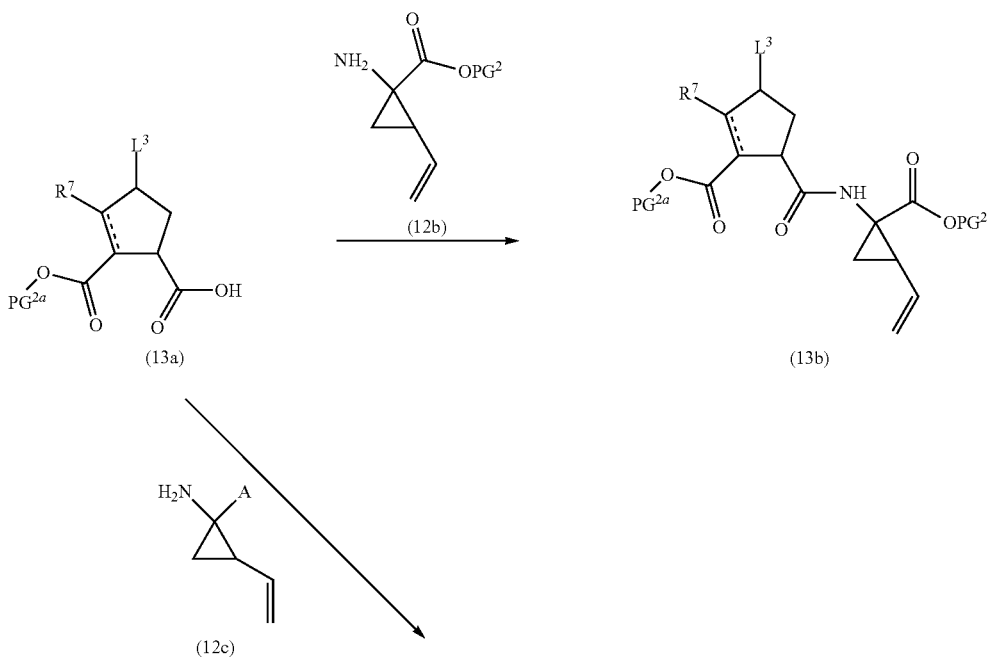

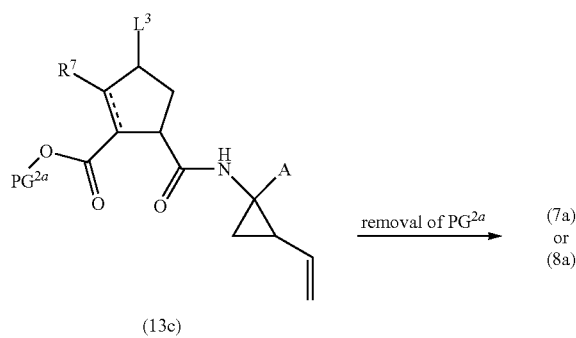

In a particular embodiment, where X is C, $R^7$ is H, and where X and the carbon bearing $R^7$ are linked by a single bond (P2 being a cyclopentane moiety), $PG^{2a}$ and $L^3$ taken together form a bond and the P2 building block is represented by formula:

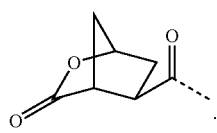

(c)

Bicyclic acid (14a) is reacted with (12b) or (12c) similar as described above to (14b) and (14c) respectively, wherein the lactone is opened giving intermediates (14c) and (14e). The lactones can be opened using ester hydrolysis procedures, for example using the reaction conditions described above for the alkaline removal of a $PG^1$ group in (9b), in particular using basic conditions such as an alkali metal hydroxide, e.g. NaOH, KOH, in particular LiOH.

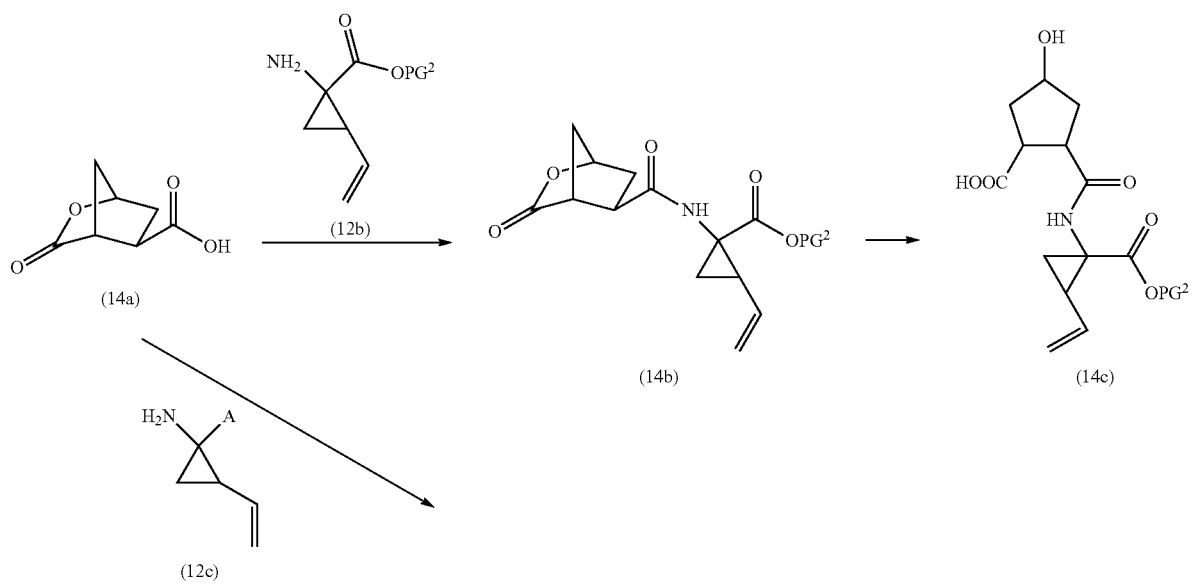

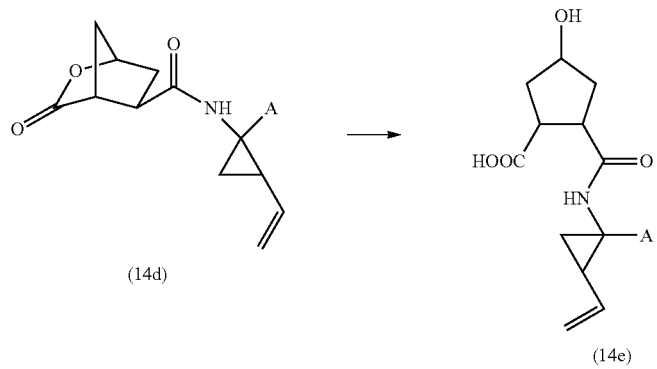

Intermediates (14c) and (14e) can be processed further as described hereinafter.

Coupling of P3 and P2 Building Blocks

For P2 building blocks that have a pyrrolidine moiety, the P3 and P2 or P3 and P2-P1 building blocks are linked using a carbamate forming reaction following the procedures described above for the coupling of (5a) with (5b). A general procedure for coupling P2 blocks having a pyrrolidine moiety is represented in the following reaction scheme wherein $L^3$ is as specified above and $L^4$ is a group —O—$PG^2$, a group

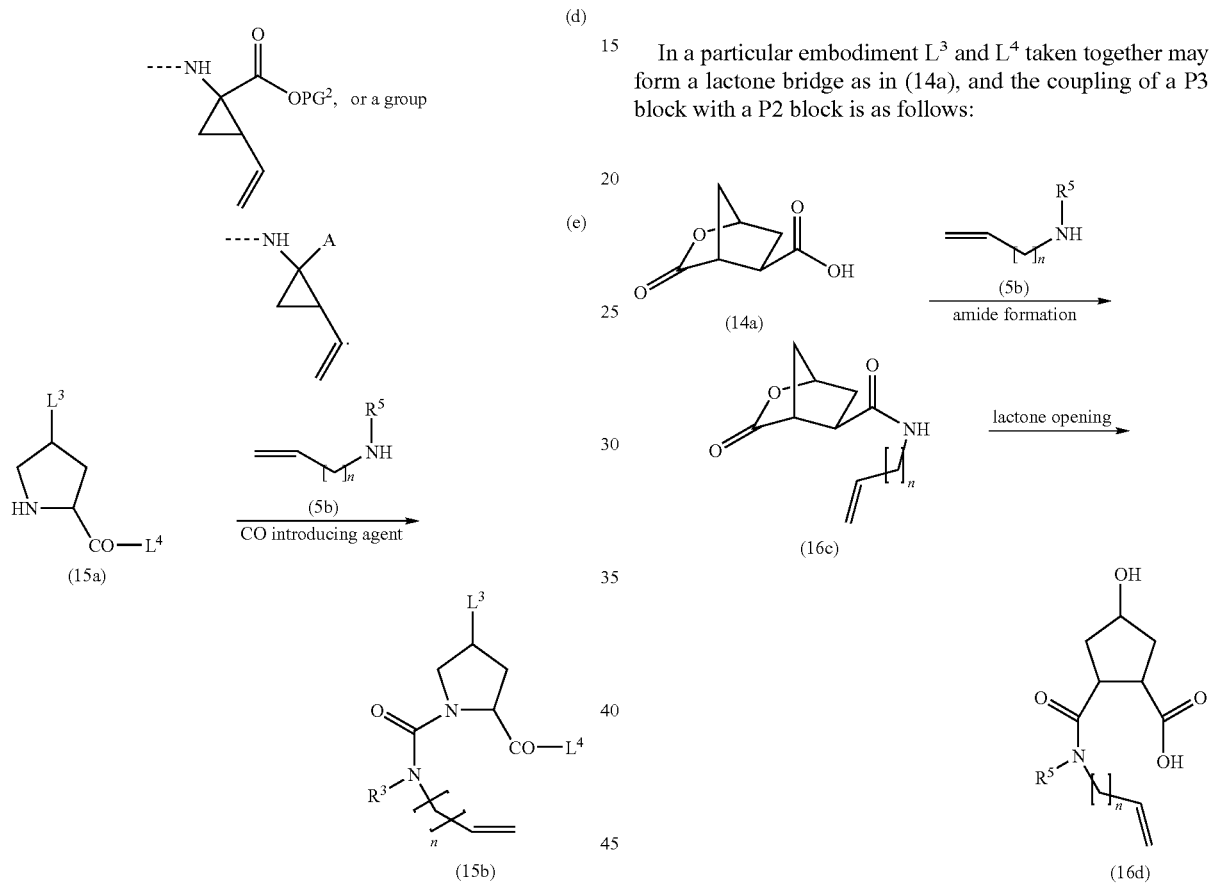

In one embodiment $L^4$ in (15a) is a group —$OPG^2$, the $PG^2$ group may be removed and the resulting acid coupled with cyclopropyl amino acids (12a) or (12b), yielding intermediates (12d) or (12e) wherein $L^2$ is a radical (d) or (e).

A general procedure for coupling P3 blocks with a P2 block or a with a P2-P1 block wherein the P2 is a cyclopentane or cyclopentene is shown in the following scheme. $L^3$ and $L^4$ are as specified above.

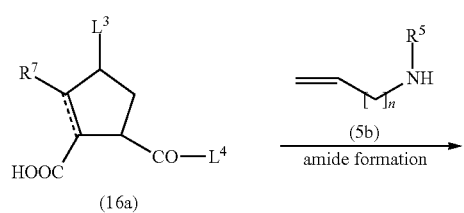

In a particular embodiment $L^3$ and $L^4$ taken together may form a lactone bridge as in (14a), and the coupling of a P3 block with a P2 block is as follows:

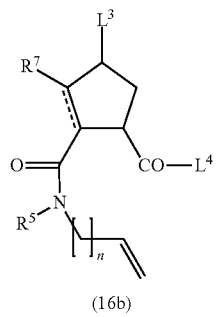

Bicyclic lactone (14a) is reacted with (5b) in an amide forming reaction to amide (16c) in which the lactone bridge is opened to (16d). The reaction conditions for the amide forming and lactone opening reactions are as described above or hereinafter. Intermediate (16d) in turn can be coupled to a P1 group as described above.

The reactions in the above schemes are conducted using the same procedures as described above for the reactions of (5a), (7a) or (8a) with (5b) and in particular the above reactions wherein $L^4$ is a group (d) or (e) correspond to the reactions of (5a), (7a) or (8a) with (5b), as described above.

The building blocks P1, P1', P2 and P3 used in the preparation of the compounds of formula (I) can be prepared starting from art-known intermediates. A number of such syntheses are described hereafter in more detail.

The individual building blocks can first be prepared and subsequently coupled together or alternatively, precursors of the building blocks can be coupled together and modified at a later stage to the desired molecular composition.

The functionalities in each of the building blocks may be protected to avoid side reactions.

Synthesis of P2 Building Blocks

The P2 building blocks contain either a pyrrolidine, a cyclopentane, or a cyclopentene moiety substituted with a group —O—R$^{11}$.

P2 building blocks containing a pyrrolidine moiety can be derived from commercially available hydroxy proline.

The preparation of P2 building blocks that contain a cylopentane ring may be performed as shown in the scheme below.

Lewis acid or with di-tert-butyl dicarbonate in the presence of a base such as a tertiary amine like dimethylamino-pyridine or triethylamine in a solvent like dichloromethane. Lactone opening of (17c) using reaction conditions described above, in particular with lithium hydroxide, yields the acid (17d), which can be used further in coupling reactions with P1 building blocks. The free acid in (17d) may also be protected, preferably with an acid protecting group PG$^{2a}$ that is selectively cleavable towards PG$^2$, and the hydroxy function may be converted to a group —OPG$^1$ or to a group —O—R$^{11}$. The products obtained upon removal of the group PG$^2$ are inter-

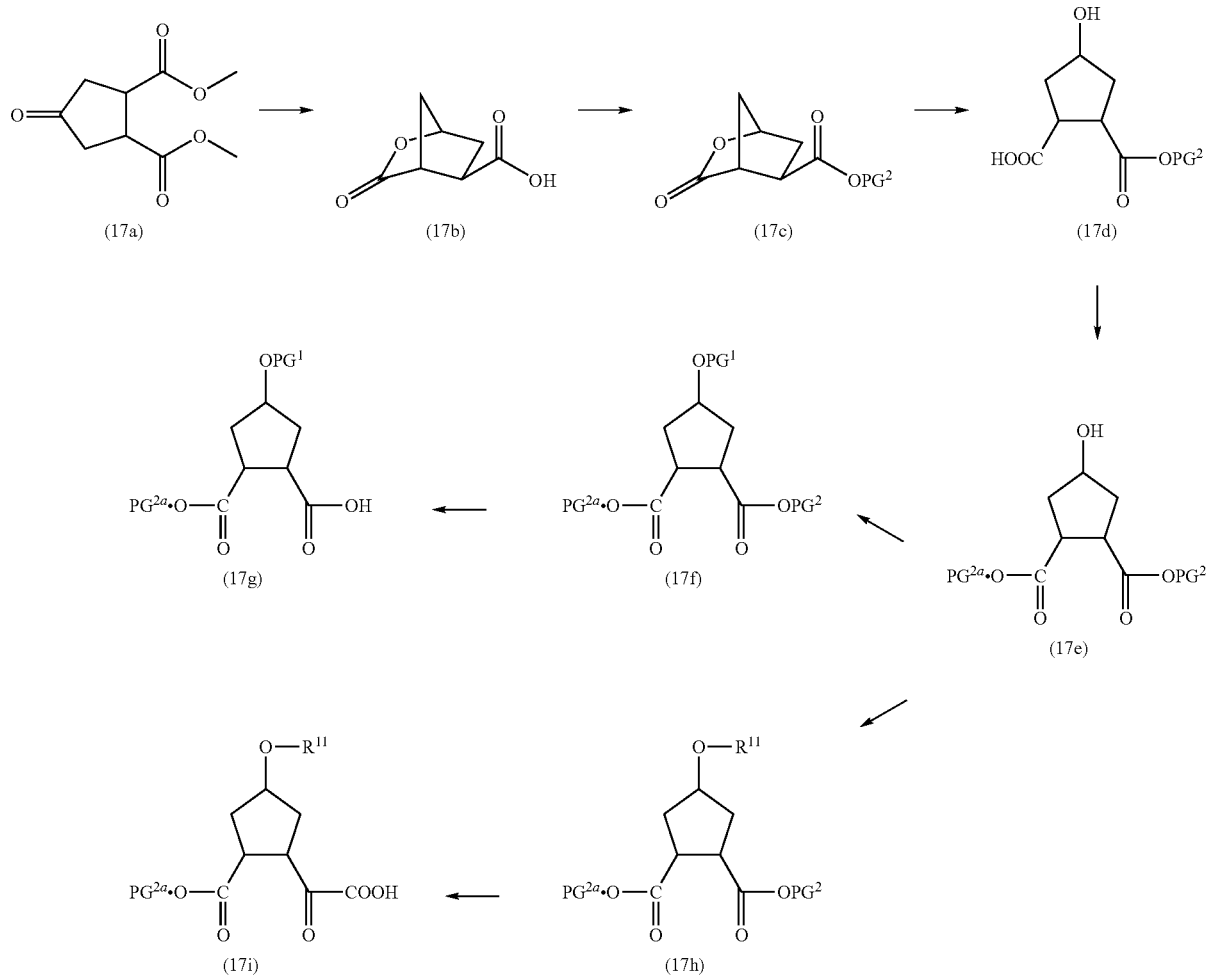

The bicyclic acid (17b) can be prepared, for example, from 3,4-bis(methoxycarbonyl)-cyclopentanone (17a), as described by Rosenquist et al. in Acta Chem. Scand. 46 (1992) 1127-1129. A first step in this procedure involves the reduction of the keto group with a reducing agent like sodium borohydride in a solvent such as methanol, followed by hydrolysis of the esters and finally ring closure to the bicyclic lactone (17b) using lactone forming procedures, in particular by using acetic anhydride in the presence of a weak base such as pyridine. The carboxylic acid functionality in (17b) can then be protected by introducing an appropriate carboxyl protecting group, such as a group PG$^2$, which is as specified above, thus providing bicyclic ester (17c). The group PG$^2$ in particular is acid-labile such as a t.butyl group and is introduced e.g. by treatment with isobutene in the presence of a mediates (17g) and (17i) which correspond to intermediates (13a) or (16a) specified above.

Intermediates with specific stereochemistry may be prepared by resolving the intermediates in the above reaction sequence. For example, (17b) may be resolved following art-known procedures, e.g. by salt form action with an optically active base or by chiral chromatography, and the resulting stereoisomers may be processed further as described above. The OH and COOH groups in (17d) are in cis position. Trans analogs can be prepared by inverting the stereochemistry at the carbon bearing the —OH function by using specific reagents in the reactions introducing —OPG$^1$ or —O—R$^{11}$ that invert the stereochemistry, such as, e.g. by applying a Mitsunobu reaction.

In one embodiment, the intermediates (17d) are coupled to P1 blocks (12b) or (12c), which coupling reactions correspond to the coupling of (13a) or (16a) with the same P1 blocks, using the same conditions. Subsequent introduction of a —O—R$^{11}$ substituent as described above followed by removal of the acid protection group PG$^2$ yields intermediates (8a-1), which are a subclass of the intermediates (7a), or part of the intermediates (16a). The reaction products of the PG$^2$ removal can be further coupled to a P3 building block. In one embodiment PG$^2$ in (17d) is t.butyl which can be removed under acidic conditions, e.g. with trifluoroacetic acid.

An unsaturated P2 building block, i.e. a cyclopentene ring, may be prepared as illustrated in the scheme below.

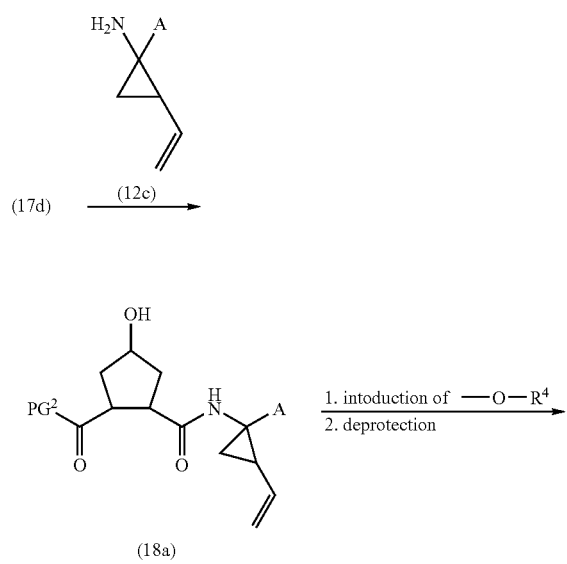

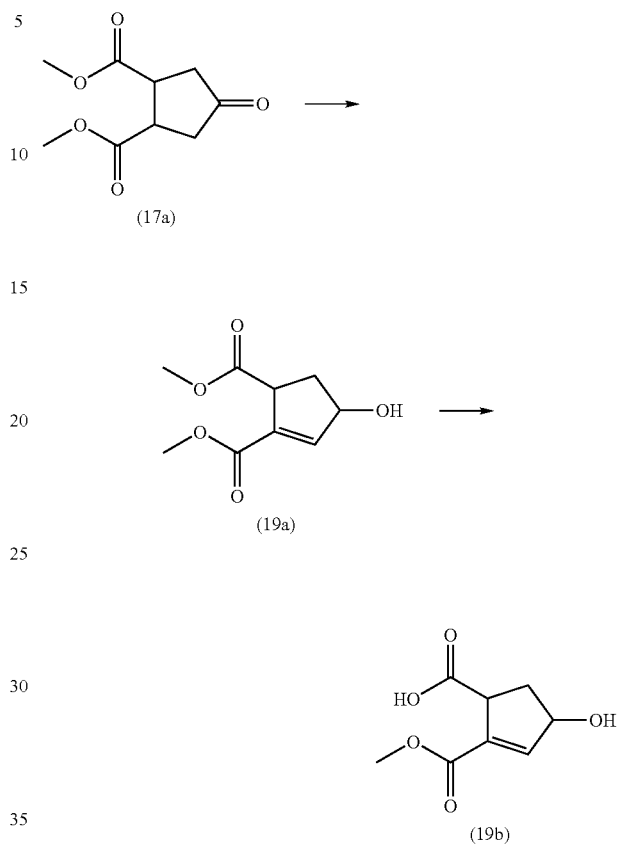

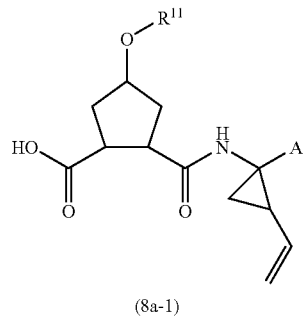

A bromination-elimination reaction of 3,4-bis(methoxycarbonyl)cyclopentanone (17a) as described by Dolby et al. in J. Org. Chem. 36 (1971) 1277-1285 followed by reduction of the keto functionality with a reducing agent like sodium borohydride provides the cyclopentenol (19a). Selective ester hydrolysis using for example lithium hydroxide in a solvent like a mixture of dioxane and water, provides the hydroxy substituted monoester cyclopentenol (19b).

An unsaturated P2 building block wherein R$^7$ can also be other than hydrogen, may be prepared as shown in the scheme below.

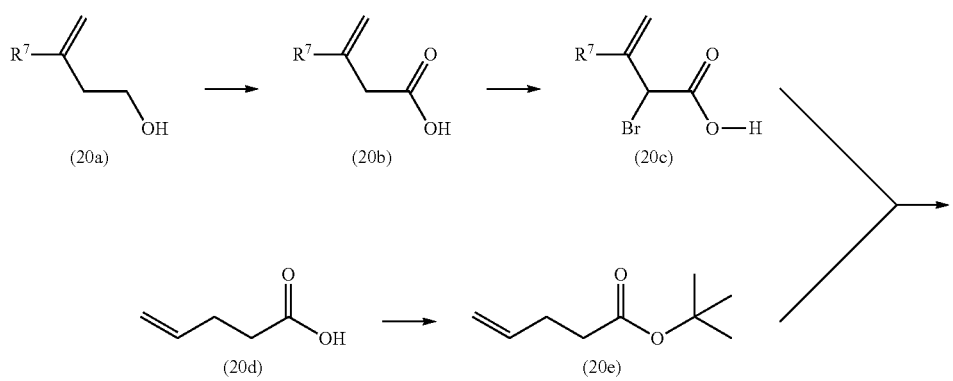

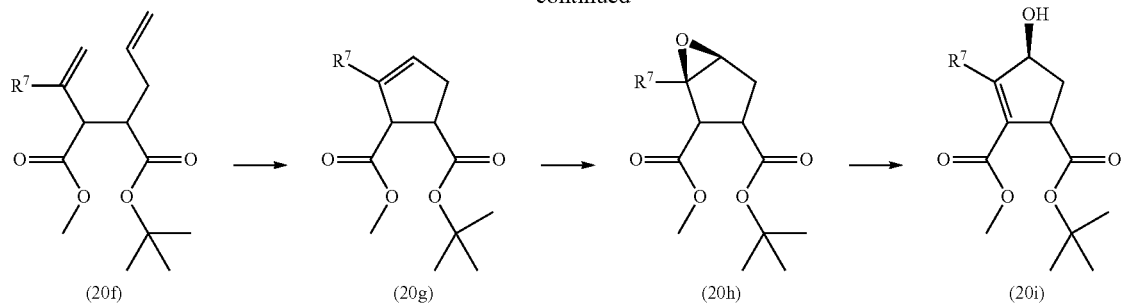

Oxidation of commercially available 3-methyl-3-buten-1-ol (20a), in particular by an oxidizing agent like pyridinium chlorochromate, yields (20b), which is converted to the corresponding methyl ester, e.g. by treatment with acetyl chloride in methanol, followed by a bromination reaction with bromine yielding the α-bromo ester (20c). The latter can then be condensed with the alkenyl ester (20e), obtained from (20d) by an ester forming reaction. The ester in (20e) preferably is a t.butyl ester which can be prepared from the corresponding commercially available acid (20d), e.g. by treatment with di-tert-butyl dicarbonate in the presence of a base like dimethylaminopyridine. Intermediate (20e) is treated with a base such as lithium diisopropyl amide in a solvent like tetrahydrofuran, and reacted with (20c) to give the alkenyl diester (20f). Cyclisation of (20f) by an olefin metathesis reaction, performed as described above, provides cyclopentene derivative (20g). Stereoselective epoxidation of (20g) can be carried out using the Jacobsen asymmetric epoxidation method to obtain epoxide (20h). Finally, an epoxide opening reaction under basic conditions, e.g. by addition of a base, in particular DBN (1,5-diazabicyclo-[4.3.0]non-5-ene), yields the alcohol (20i). Optionally, the double bond in intermediate (20i) can be reduced, for example by catalytic hydrogenation using a catalyst like palladium on carbon, yielding the corresponding cyclopentane compound. The t.butyl ester may be removed to the corresponding acid, which subsequently is coupled to a P1 building block.

The —O—$R^{11}$ group can be introduced on the pyrrolidine, cyclopentane or cyclopentene rings at any convenient stage of the synthesis of the compounds according to the present invention. One approach is to first introduce the —O—$R^{11}$ group to the said rings and subsequently add the other desired building blocks, i.e. P1 (optionally with the P1' tail) and P3, followed by the macrocycle formation. Another approach is to couple the building blocks P2, bearing no —O—$R^{11}$ substituent, with each P1 and P3, and to add the —O—$R^{11}$ group either before or after the macrocycle formation. In the latter procedure, the P2 moieties have a hydroxy group, which may be protected by a hydroxy protecting group $PG^1$.

$R^{11}$ groups can be introduced on building blocks P2 by reacting hydroxy substituted intermediates (21a) or (21b) with intermediates (4b) similar as described above for the synthesis of (I) starting from (4a). These reactions are represented in the schemes below, wherein $L^2$ is as specified above and $L^5$ and $L^{5a}$ independently from one another, represent hydroxy, a carboxyl protecting group —$OPG^2$ or —$OPG^{2a}$, or $L^5$ may also represent a P1 group such as a group (d) or (e) as specified above, or $L^{5a}$ may also represent a P3 group such as a group (b) as specified above The groups $PG^2$ and $PG^{2a}$ are as specified above. Where the groups $L^5$ and $L^{5a}$ are $PG^2$ or $PG^{2a}$, they are chosen such that each group is selectively cleavable towards the other. For example, one of $L^5$ and $L^{5a}$ may be a methyl or ethyl group and the other a benzyl or t.butyl group.

In one embodiment in (21a), $L^2$ is PG and $L^5$ is —$OPG^2$, or in (21d), $L^{5a}$ is —$OPG^2$ and $L^5$ is —$OPG^2$ and the $PG^2$ groups are removed as described above.

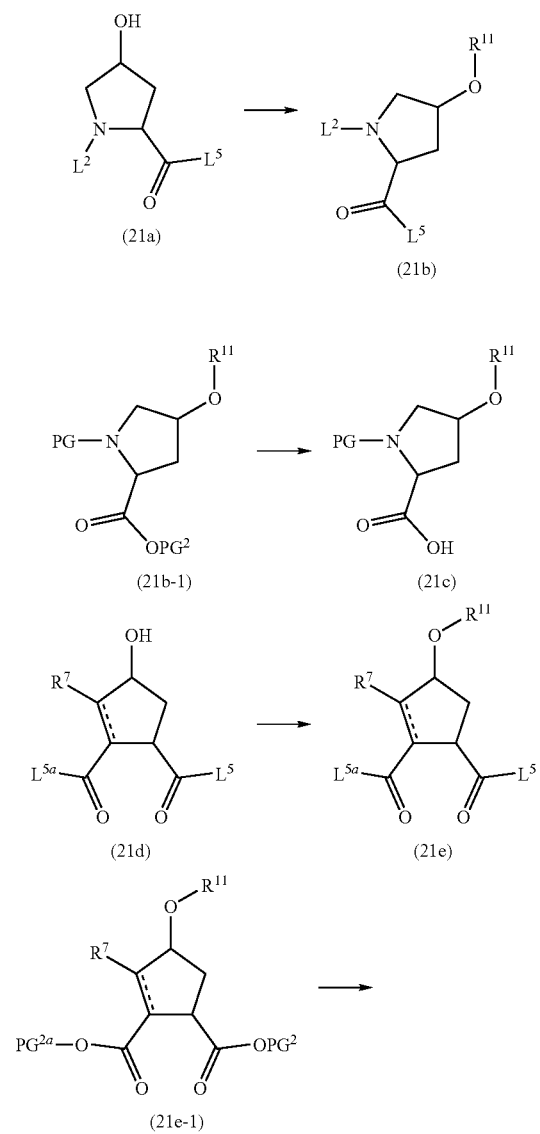

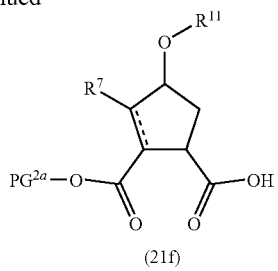

(21f)

In another embodiment the group L² is BOC, L⁵ is hydroxy and the starting material (21a) is commercially available BOC-hydroxyproline, or any other stereoisomeric form thereof, e.g. BOC-L-hydroxyproline, in particular the trans isomer of the latter. Where L⁵ in (21b) is a carboxyl-protecting group, it may be removed following procedures described above to (21c). In still another embodiment PG in (21b-1) is Boc and PG² is a lower alkyl ester, in particular a methyl or ethyl ester. Hydrolysis of the latter ester to the acid can be done by standard procedures, e.g. acid hydrolysis with hydrochloric acid in methanol or with an alkali metal hydroxide such as NaOH, in particular with LiOH. In another embodiment, hydroxy substituted cyclopentane or cyclopentene analogs (21d) are converted to (21e), which, where L⁵ and L⁵ᵃ are —OPG² or —OPG²ᵃ, may be converted to the corresponding acids (21f) by removal of the group PG². Removal of PG²ᵃ in (21e-1) leads to similar intermediates.

Synthesis of P1 Building Blocks

The cyclopropane amino acid used in the preparation of the P1 fragment is commercially available or can be prepared using art-known procedures.

In particular the amino-vinyl-cyclopropyl ethyl ester (12b) may be obtained according to the procedure described in WO 00/09543 or as illustrated in the following scheme, wherein PG² is a carboxyl protecting group as specified above:

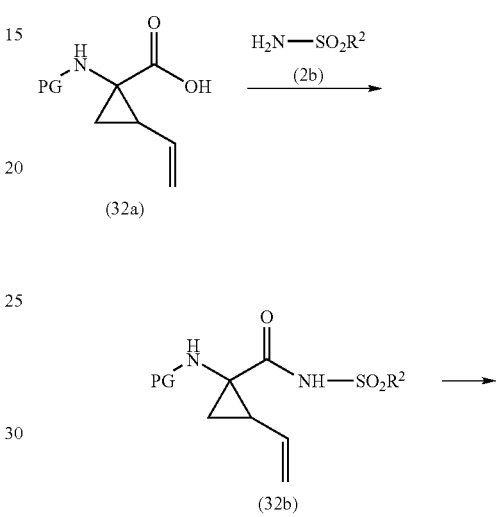

Treatment of commercially available or easily obtainable imine (31a) with 1,4-dihalo-butene in presence of a base produces (31b), which after hydrolysis yields cyclopropyl amino acid (12b), having the allyl substituent syn to the carboxyl group. Resolution of the enantiomeric mixture (12b) results in (12b-1). The resolution is performed using art-known procedures such as enzymatic separation; crystallization with a chiral acid; or chemical derivatization; or by chiral column chromatography. Intermediates (12b) or (12b-1) may be coupled to the appropriate P2 derivatives as described above.

P1 building blocks for the preparation of compounds according to general formula (I) wherein A is —COOR¹, —CO—NH—SO₂R² or —CO—NH—PO(OR⁴ᵃ)(OR⁴ᵇ) can be prepared by reacting amino acids (32a) with the appropriate alcohol, sulfonamide or phosphoramide respectively under standard conditions for ester or amide formation. Cyclopropyl amino acids (32a) are prepared by introducing a N-protecting group PG, and removal of PG², and the resulting PG protected amino acids (32a) are converted to the amides (12c-1) or esters (12c-2), which are subgroups of the intermediates (12c), as outlined in the following reaction scheme, wherein PG is as specified above.

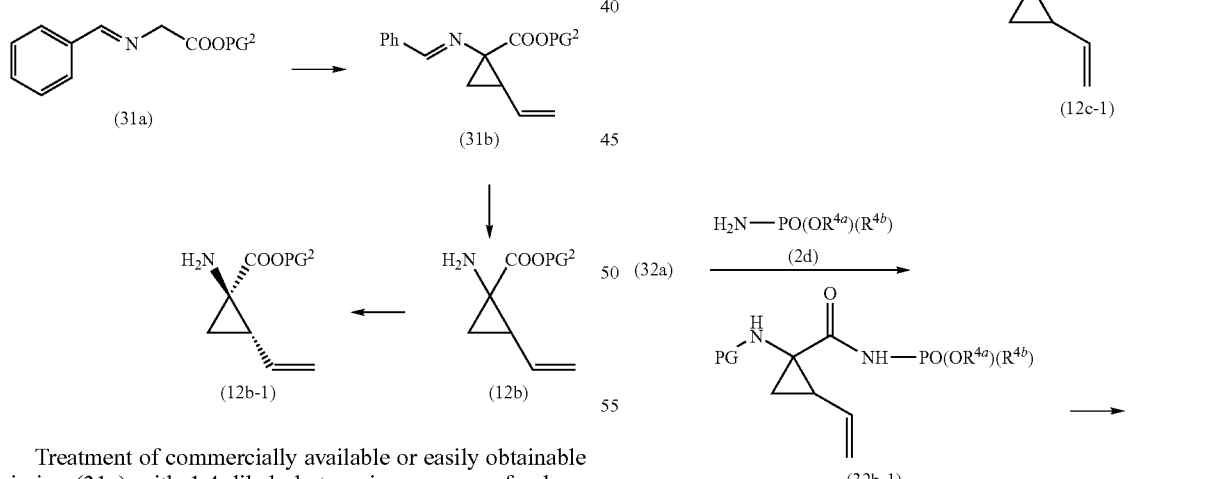

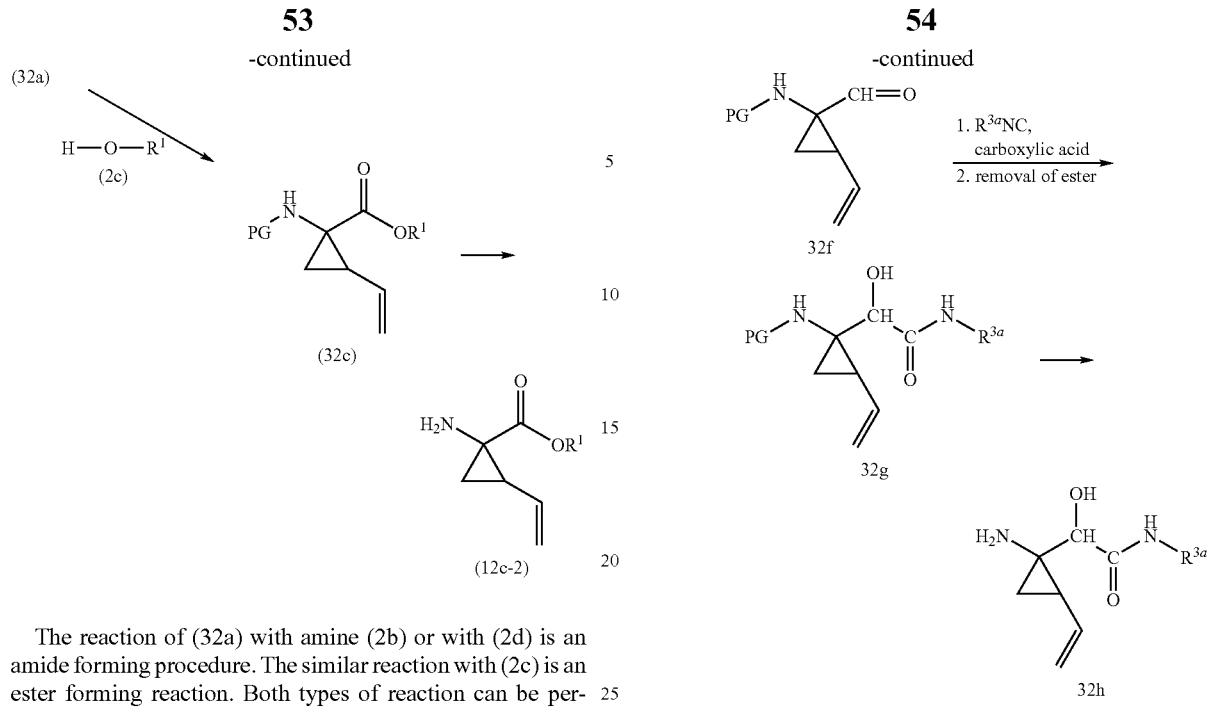

The reaction of (32a) with amine (2b) or with (2d) is an amide forming procedure. The similar reaction with (2c) is an ester forming reaction. Both types of reaction can be performed following the procedures described above. This reaction yields intermediates (32b), (32b-1), or (32c), from which the amino protecting group is removed by standard methods such as those described above. This in turn results in the desired intermediate (12c-1), (12c-1a), or (12c-2). Starting materials (32a) may be prepared from the above-mentioned intermediates (12b) by first introducing a N-protecting group PG and subsequent removal of the group $PG^2$.

In one embodiment the reaction of (32a) with (2b) or with (2d) is done by treatment of the amino acid with a coupling agent, for example N,N'-carbonyl-diimidazole (CDI) or the like, in a solvent like THF followed by reaction with (2b) or with (2b-1) in the presence of a base such as 1,8-diazabicyclo[5.4.0]undec-7-ene (DBU). Alternatively the amino acid can be treated with (2b) or (2d) in the presence of a base like diisopropylethylamine, or with sodium hydride in case of (2d), followed by treatment with a coupling agent such as benzotriazole-1-yl-oxy-tris-pyrrolidino-phosphonium hexafluorophosphate (commercially available as PyBOP®) to effect the introduction of the sulfonamide group.

P1 building blocks for the preparation of compounds according to general formula (I) wherein A is —C(=O)C(=O)NR$^{3a}$R$^{3b}$ are conveniently prepared as outlined in the following scheme.

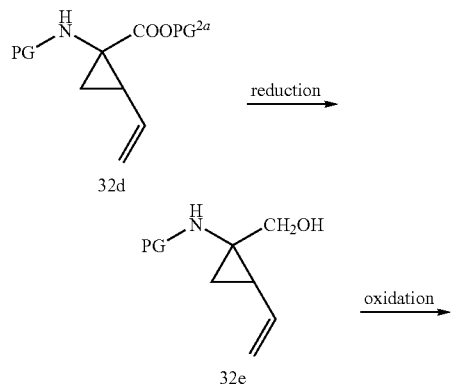

$PG^{2a}$ in starting material (32d) is an alkyl group, in particular $C_{1-6}$alkyl such as methyl or ethyl. (32d) can be obtained by an ester formation reaction of (32a) with an appropriate alkanol, or by introducing a nitrogen-protecting group PG on (12b), as described above. Reduction of the ester group in the amino acid derivative (32d) to the corresponding hydroxymethylene intermediate (32e), effected for example by treatment with lithium borohydride, followed by oxidation of the resulting hydroxymethylene group using a mild oxidant such as for instance Dess-Martin periodinane, provides the aldehyde (32f). Reaction of the latter aldehyde (32f) with a suitable isonitrile derivative and in the presence of a carboxylic acid such as trifluoroacetic acid (TFA) in the presence of a base, e.g. pyridine, in a Passerini reaction (as described, for example, in Org. Lett., Vol. 2, No 18, 2000), gives the carboxylic acid ester of the resulting α-hydroxy amide, e.g. in case of TFA, the trifluoroacetate. The carboxylic ester in the thus obtained α-hydroxy amide can then be removed using standard procedures, e.g. using basic conditions such as LiOH, thus yielding α-hydroxy amide (32g). Removal of group PG results in intermediates (32h), which can be coupled to a P2 group. The hydroxy function in (32g) can be oxidized to the corresponding α-keto amide, but in order to avoid side reactions the α-hydroxy amide or its precursor carboxylic ester are used in further reactions (such as removal of the N-protecting group, coupling with a P2 moiety, etc.). Oxidation of the α-hydroxy group of the P1 moiety is then performed at any convenient stage of the synthesis, e.g. after this coupling with a P2 moiety or at later stages of the synthesis, e.g. the last step, using a mild oxidant such as for instance Dess-Martin periodinane, thus giving compounds of formula I, or intermediates, wherein A is —C(=O)C(=O)NR$^{3a}$R$^{3b}$.

The above procedure, i.e. reduction of the ester, oxidation to the aldehyde, reaction with an isonitrile can also be performed at later stages of the synthesis procedure, e.g. after building up the macrocycle.

P1 building blocks useful for the preparation of compounds according to general formula (I) wherein A is —C(=O)NH—P(=O)(OR$^{4a}$)(R$^{4b}$), or —P(=O)(OR$^{4a}$)

($R^{4b}$) a phosphonate can be prepared following procedures described in WO 2006/020276. In particular compounds of formula (I) wherein A is —P(=O)(OR$^{4a}$)(R$^{4b}$) can be prepared as follows:

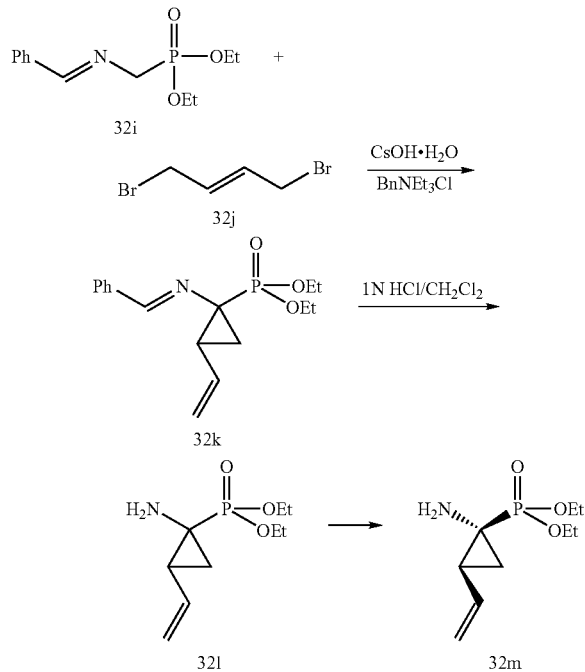

Starting material 32i is reacted with a base, in particular with CsOH, preferably in the presence of a phase transfer catalyst such as triethylbenzylammonium chloride, and 32j is added forming a cyclopropyl ring with a vinyl side chain, i.e. cyclopropyl phosphonate 32k. The phenyl-CH= protecting group is removed under acidic conditions (e.g. HCl in dichloromethane) yielding 32l. The latter can be resolved in its stereoisomers using art-known methodolgy, e.g. by formation of a salt with an optically active acid, for example with dibenzoyl-L-tartaric acid, which after removal of the tartaric acid derivative yields 32m. Analogues other that the ethyl phophonates can be prepared from starting materials 32i having ester groups other than ethyl. The starting materials 32i are known materials or can easily be prepared using art-known methods.

Intermediates (12c-1) or (12c-2) in turn may be coupled to the appropriate proline, cyclopentane or cyclopentene derivatives as described above.

Synthesis of the P3 Building Blocks

The P3 building blocks are available commercially or can be prepared according to methodologies known to the skilled in the art. One of these methodologies is shown in the scheme below and uses monoacylated amines, such as trifluoroacetamide or a Boc-protected amine.

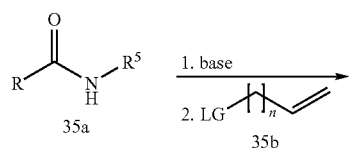

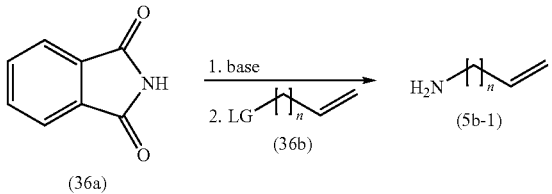

In the above scheme, R together with the CO group forms a N-protecting group, in particular R is t-butoxy, trifluoromethyl; $R^5$ and n are as defined above and LG is a leaving group, in particular halogen, e.g. chloro or bromo.

The monoacylated amines (33a) are treated with a strong base such as sodium hydride and are subsequently reacted with a reagent LG-C$_{5-8}$alkenyl (33b), in particular haloC$_{5-8}$ alkenyl, to form the corresponding protected amines (33c). Deprotection of (33c) affords (5b), which are building blocks P3. Deprotection will depend on the functional group R, thus if R is t-butoxy, deprotection of the corresponding Boc-protected amine can be accomplished with an acidic treatment, e.g. trifluoroacetic acid. Alternatively, when R is for instance trifluoromethyl, removal of the R group is accomplished with a base, e.g. sodium hydroxide.

The following scheme illustrates yet another method for preparing a P3 building block, namely a Gabriel synthesis of primary C$_{5-8}$alkenylamines, which can be carried out by the treatment of a phthalimide (34a) with a base, such as NaOH or KOH, and with (33b), which is as specified above, followed by hydrolysis of the intermediate N-alkenyl imide to generate a primary C$_{5-8}$alkenylamine (5b-1).

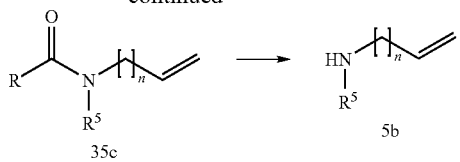

In the above scheme, n is as defined above.

Compounds of formula (I) may be converted into each other following art-known functional group transformation reactions. For example, amino groups may be N-alkylated, nitro groups reduced to amino groups, a halo atom may be exchanged for another halo.

A number of the intermediates used to prepare the compounds of formula (I) are known compounds or are analogues of known compounds, which can be prepared following modifications of art-known methodologies readily accessible to the skilled person.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzene-carboperoxoic acid, peroxoalkanoic acids, e.g. peroxoacetic acid, alkylhydroperoxides, e.g. tert-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) may be obtained as racemic mixtures of enantiomers which can be separated from one another following art-known resolution procedures. The racemic compounds of formula (I) that are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound may be synthesized by stereospecific methods of preparation. These methods may advantageously employ enantiomerically pure starting materials.

In a further aspect, the present invention concerns a pharmaceutical composition comprising a therapeutically effective amount of a compound of formula (I) as specified herein, or a compound of any of the subgroups of compounds of formula (I) as specified herein, and a pharmaceutically acceptable carrier. A therapeutically effective amount in this context is an amount sufficient to act in a prophylactic way against, to stabilize or to reduce viral infection, and in particular HCV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the subgroups of compounds of formula (I) as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties. Viral infections and their associated diseases treatable using the compounds and methods of the present invention include those infections brought on by HCV and other pathogenic flaviviruses such as Yellow fever, Dengue fever (types 1-4), St. Louis encephalitis, Japanese encephalitis, Murray valley encephalitis, West Nile virus and Kunjin virus. The diseases associated with HCV include progressive liver fibrosis, inflammation and necrosis leading to cirrhosis, end-stage liver disease, and HCC; and for the other pathogenic flaviruses the diseases include yellow fever, dengue fever, hemorraghic fever and encephalitis. A number of the compounds of this invention moreover are active against mutated strains of HCV. Additionally, many of the compounds of this invention show a favorable pharmacokinetic profile and have attractive properties in terms of bioavailability, including an acceptable half-life, AUC (area under the curve) and peak values and lacking unfavourable phenomena such as insufficient quick onset and tissue retention.

The in vitro antiviral activity against HCV of the compounds of formula (I) can be tested in a cellular HCV replicon system based on Lohmann et al. (1999) Science 285:110-113, with the further modifications described by Krieger et al. (2001) Journal of Virology 75: 4614-4624 (incorporated herein by reference), which is further exemplified in the examples section. This model, while not a complete infection model for HCV, is widely accepted as the most robust and efficient model of autonomous HCV RNA replication currently available. Compounds exhibiting anti-HCV activity in this cellular model are considered as candidates for further development in the treatment of HCV infections in mammals. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to their antiviral properties, particularly their anti-HCV properties, the compounds of formula (I) or any subgroup thereof, N-oxides, pharmaceutically acceptable addition salts, and stereochemically isomeric forms, are useful in the treatment of individuals infected with a virus, particularly a virus that is HCV, and for the prophylaxis of viral infections, in particular HCV infections. In general, the compounds of the present invention may be useful in the treatment of warm-blooded animals infected with viruses, in particular flaviviruses such as HCV.

The compounds of the present invention or any subgroup thereof may therefore be used as a medicine. Said use as a medicine or method of treatment comprises the systemic administration to virally infected subjects or to subjects susceptible to viral infections of an amount effective to combat the conditions associated with the viral infection, in particular HCV infection.

The present invention also relates to the use of the present compounds or any subgroup thereof in the manufacture of a medicament for the treatment or the prevention of a viral infection, particularly HCV infection.

The present invention furthermore relates to a method of treating a warm-blooded animal infected by a virus, or being at risk of infection by a virus, in particular by HCV, said method comprising the administration of an anti-virally effective amount of a compound of formula (I), as specified herein, or of a compound of any of the subgroups of compounds of formula (I), as specified herein.

In general it is contemplated that an antiviral effective daily amount would be from 0.01 mg/kg to 500 mg/kg body weight, or from 0.1 mg/kg to 50 mg/kg body weight, or from 0.5 mg/kg to 5 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The invention also relates to a combination of a compound of formula (I), including a stereoisomeric form thereof, a pharmaceutically acceptable salt, or a pharmaceutically acceptable solvate thereof, and another antiviral compound, in particular another anti-HCV compound. The term "combination" may relate to a product containing (a) a compound of formula (I), as specified above, and (b) optionally another anti-HCV compound, as a combined preparation for simultaneous, separate or sequential use in treatment of HCV infections.

Anti-HCV compounds that can be used in such combinations include agents selected from an HCV polymerase inhibitor, an HCV protease inhibitor, an inhibitor of another target in the HCV life cycle, and an immunomodulatory agent, and combinations thereof. HCV polymerase inhibitors include, NM283 (valopicitabine), R803, JTK-109, JTK-003, HCV-371, HCV-086, HCV-796 and R-1479. Inhibitors of HCV proteases (NS2-NS3 inhibitors and NS3-NS4A inhibitors) include the compounds of WO 02/18369 (see, e.g., page 273, lines 9-22 and page 274, line 4 to page 276, line 11); BILN-2061, VX-950, GS-9132 (ACH-806), SCH-503034, and SCH-6. Further agents that can be used are those disclosed in WO 98/17679, WO 00/056331 (Vertex); WO 98/22496 (Roche); WO 99/07734, (Boehringer Ingelheim), WO 2005/073216, WO 2005/073195 (Medivir) and structurally similar agents.

Inhibitors of other targets in the HCV life cycle, including NS3 helicase; metallo-protease inhibitors; antisense oligonucleotide inhibitors, such as ISIS-14803, AVI-4065 and the like; siRNA's such as SIRPLEX-140-N and the like; vector-encoded short hairpin RNA (shRNA); DNAzymes; HCV specific ribozymes such as heptazyme, RPI.13919 and the like; entry inhibitors such as HepeX-C, HuMax-HepC and the like; alpha glucosidase inhibitors such as celgosivir, UT-231B and the like; KPE-02003002; and BIVN 401.

Immunomodulatory agents include, natural and recombinant interferon isoform compounds, including α-interferon, β-interferon, γ-interferon, ω-interferon and the like, such as Intron A®, Roferon-A®, Canferon-A300®, Advaferon®, Infergen®, Humoferon®, Sumiferon MP®, Alfaferone®, IFN-beta®, Feron® and the like; polyethylene glycol derivatized (pegylated) interferon compounds, such as PEG interferon-α-2a (Pegasys®), PEG interferon-α-2b (PEG-Intron®), pegylated IFN-α-con1 and the like; long acting formulations and derivatizations of interferon compounds such as the albumin-fused interferon albuferon α and the like; compounds that stimulate the synthesis of interferon in cells, such as resiquimod and the like; interleukins; compounds that enhance the development of type 1 helper T cell response, such as SCV-07 and the like; TOLL-like receptor agonists such as CpG-10101 (actilon), isatoribine and the like; thymosin α-1; ANA-245; ANA-246; histamine dihydrochloride; propagermanium; tetrachlorodecaoxide; ampligen; IMP-321; KRN-7000; antibodies, such as civacir, XTL-6865, and the like; and prophylactic and therapeutic vaccines such as InnoVac C, HCV E1E2/MF59, and the like.

Other antiviral agents include, ribavirin, amantadine, viramidine, nitazoxanide; telbivudine; NOV-205; taribavirin; inhibitors of internal ribosome entry; broad-spectrum viral inhibitors, such as IMPDH inhibitors, and mycophenolic acid and derivatives thereof, and including, but not limited to VX-950, merimepodib (VX-497), VX-148, and/or VX-944); or combinations of any of the above.

Particular agents for use in said combinations include interferon-α (IFN-α), pegylated interferon-α or ribavirin, as well as therapeutics based on antibodies targeted against HCV epitopes, small interfering RNA (Si RNA), ribozymes, DNAzymes, antisense RNA, small molecule antagonists of for instance NS3 protease, NS3 helicase and NS5B polymerase.

In another aspect there are provided combinations of a compound of formula (I) as specified herein and an anti-HIV compound. The latter preferably are those HIV inhibitors that have a positive effect on drug metabolism and/or pharmacokinetics that improve bioavailability. An example of such an HIV inhibitor is ritonavir. As such, this invention further provides a combination comprising (a) an HCV NS3/4a protease inhibitor of formula (I) or a pharmaceutically acceptable salt thereof, and (b) ritonavir or a pharmaceutically acceptable salt thereof. The compound ritonavir, its pharmaceutically acceptable salts, and methods for its preparation are described in WO 94/14436. U.S. Pat. No. 6,037,157, and references cited therein: U.S. Pat. No. 5,484,801, U.S. Ser. No. 08/402,690, WO95/07696, and WO95/09614, disclose preferred dosage forms of ritonavir. One embodiment relates to a combination comprising (a) an HCV NS3/4a protease inhibitor of formula (I) or a pharmaceutically acceptable salt thereof; and (b) ritonavir or a pharmaceutically acceptable salt thereof; optionally comprising an additional anti-HCV compound selected from the compounds mentioned above.

The invention also concerns a process for preparing a combination as described herein, comprising the step of combining a compound of formula (I), as specified above, and another agent, such as an antiviral, including an anti-HCV or anti-HIV agent, in particular those mentioned above.

The said combinations may find use in the manufacture of a medicament for treating HCV infection, or another pathogenic flavi- or pestivirus, in a mammal infected therewith, said combination in particular comprising a compound of formula (I), as specified above and interferon-α (IFN-α), pegylated interferon-α, or ribavirin. Or the invention provides a method of treating a mammal, in particular a human, infected with HCV, or another pathogenic flavi- or pestivirus, comprising the administration to said mammal of an effective amount of a combination as specified herein. In particular, said treating comprises the systemic administration of the said combination and an effective amount is such amount that is effective in treating the clinical conditions associated with HCV infection.

In one embodiment the above-mentioned combinations are formulated in the form of a pharmaceutical composition that includes the active ingredients described above and a carrier, as described above. Each of the active ingredients may be formulated separately and the formulations may be co-administered, or one formulation containing both and if desired further active ingredients may be provided. In the former instance, the combinations may also be formulated as a combined preparation for simultaneous, separate or sequential use in HCV therapy. The said composition may take any of the forms described above. In one embodiment, both ingredients are formulated in one dosage form such as a fixed dosage combination. In a particular embodiment, the present invention provides a pharmaceutical composition comprising (a) a therapeutically effective amount of a compound of formula (I), including a stereoisomeric form thereof, or a pharmaceutically acceptable salt thereof, or a pharmaceutically acceptable solvate thereof, and (b) a therapeutically effective amount of ritonavir or a pharmaceutically acceptable salt thereof, and (c) a carrier.

The individual components of the combinations of the present invention can be administered separately at different times during the course of therapy or concurrently in divided or single combination forms. The present invention is meant to embrace all such regimes of simultaneous or alternating treatment and the term "administering" is to be interpreted accordingly. In a preferred embodiment, the separate dosage forms are administered simultaneously.

In one embodiment, the combinations of the present invention contains an amount of ritonavir, or a pharmaceutically acceptable salt thereof, that is sufficient to clinically improve the bioavailability of the HCV NS3/4a protease inhibitor of formula (I) relative to the bioavailability when said HCV NS3/4a protease inhibitor of formula (I) is administered alone. Or, the combinations of the present invention contains an amount of ritonavir, or a pharmaceutically acceptable salt thereof, which is sufficient to increase at least one of the pharmacokinetic variables of the HCV NS3/4a protease inhibitor of formula (I) selected from $t_{1/2}$, $C_{min}$, $C_{max}$, $C_{ss}$, AUC at 12 hours, or AUC at 24 hours, relative to said at least one pharmacokinetic variable when the HCV NS3/4a protease inhibitor of formula (I) is administered alone.

The combinations of this invention can be administered to humans in dosage ranges specific for each component comprised in said combinations, e.g the compound of formula (I) as specified above, and ritonavir or a pharmaceutically acceptable salt, may have dosage levels in the range of 0.02 to 5.0 g/day.

The weight ratio of the compound of formula (I) to ritonavir may be in the range of from about 30:1 to about 1:15, or about 15:1 to about 1:10, or about 15:1 to about 1:1, or about 10:1 to about 1:1, or about 8:1 to about 1:1, or about 1:5 to 1:1 to about 5:1, or about 3:1 to about 1:1, or about 2:1 to 1:1. The compound formula (I) and ritonavir may be co-administered once or twice a day, preferably orally, wherein the amount of the compound of formula (I) per dose is from about 1 to about 2500 mg, or about 50 to about 1500 mg, or about 100 to about 1000 mg, or about 200 to about 600 mg, or about 100 to about 400 mg; and the amount of ritonavir per dose is from 1 to about 2500 mg, or about 50 to about 1500 mg, or about 100 to about 800 mg, or about 100 to about 400 mg, or 40 to about 100 mg of ritonavir.

EXAMPLES

The following examples are intended to illustrate the present invention and not to limit it thereto. Some examples show the preparation of building blocks, which may be coupled to any other appropriate building block described herein and not only to the building blocks of the exemplified end products of formula I.

Example 1
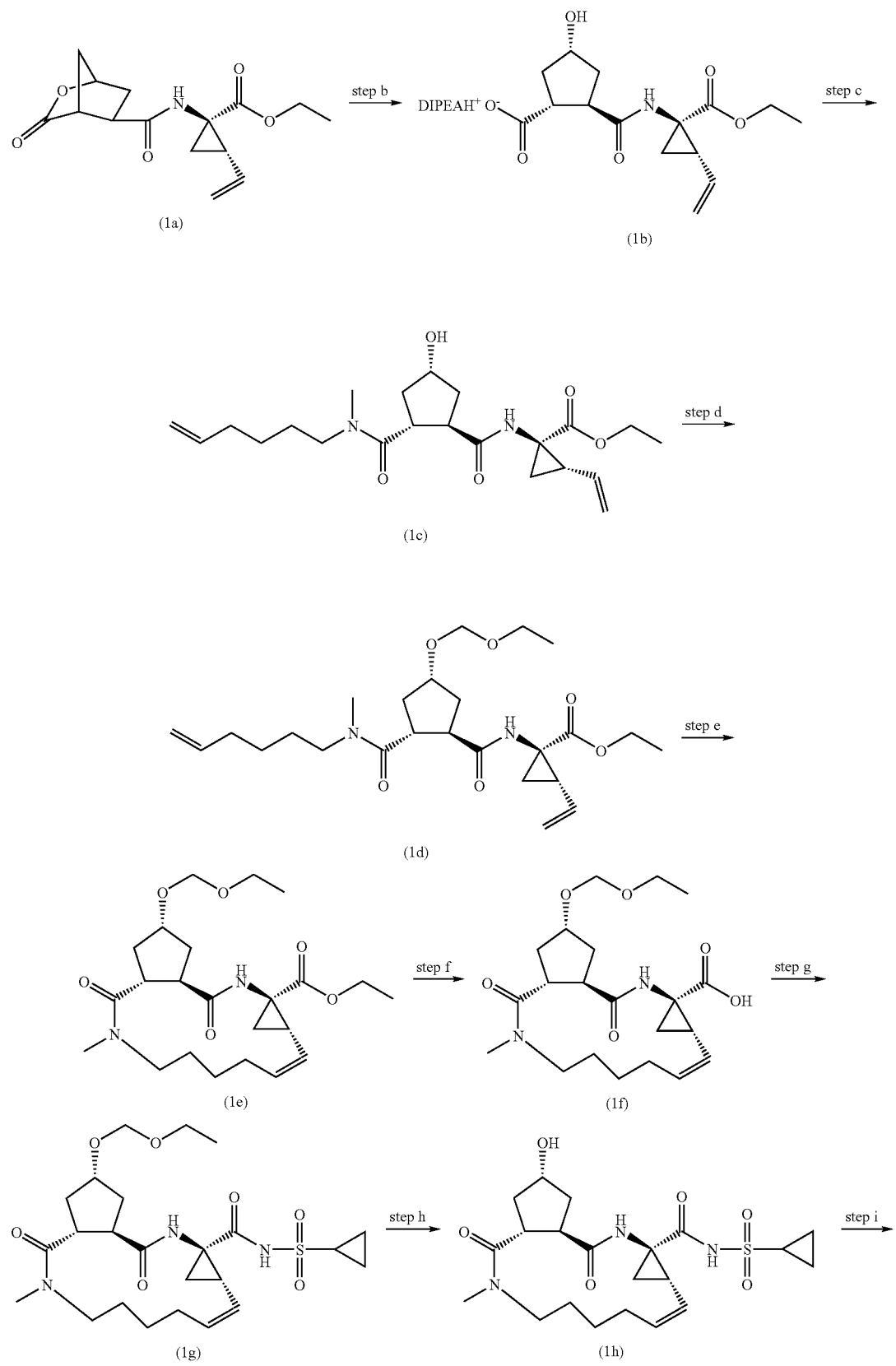

-continued

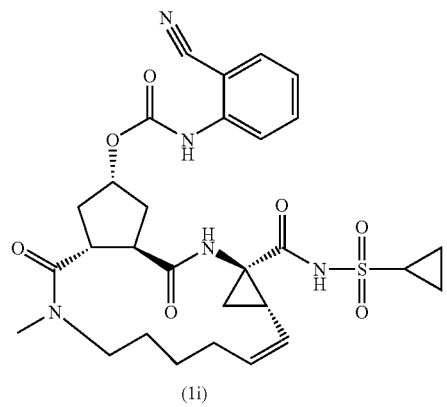 [SMILES: CN1CCCC/C=C\[C@@H]2C[C@@]2(C(=O)NS(=O)(=O)C2CC2)NC(=O)[C@@H]2C[C@@H](OC(=O)Nc3ccccc3C#N)C[C@H]2C1=O]

(1i)

Step a: 1-[(3-Oxo-2-oxa-bicyclo[2.2.1]heptane-5-carbonyl)-amino]-2-vinyl-cyclo-propane carboxylic acid ethyl ester (1a)

To a solution of 3-oxo-2-oxa-bicyclo[2.2.1]heptane-5-carboxylic acid (857 mg, 5.5 mmol), in DMF (14 ml) and DCM (25 ml) at room temperature, was added 1-amino-2-vinylcyclopropanecarboxylic acid ethyl ester (1.15 g, 6.0 mmol), HATU (2.29 g, 6.0 mmol) and DIPEA (3.82 ml, 22 mmol). The reaction was stirred under $N_2$-atmosphere at ambient temperature for 1 h. LC/MS analysis showed complete conversion and the reaction mixture was concentrated in vacuo. The residue was re-dissolved in DCM (100 ml) and 0.1 M HCl (aq) and the layers separated. The organic phase was washed with $NaHCO_3$ (aq) and brine, dried ($MgSO_4$) and filtered. Removal of the solvent in vacuo afforded the title compound (1.6 g, 99%). LC/MS (Method A): $t_R$=2.46 min, >95%, m/z ($ESI^+$)=294($MH^+$)

Step b: 2-(1-Ethoxycarbonyl-2-vinylcyclopropylcarbamoyl)-4-hydroxy-cyclopentane carboxylic acid diisopropylethylamine salt (1b)

To a solution of the ester (1a) (800 mg, 2.73 mmol) in water (15 ml) in a 20 ml microwave reaction vessel was added DIPEA (1.2 ml, 6.8 mmol) and a magnetic stirring bar. The reaction vessel was sealed and the immiscible slurry was shaken vigorously before insertion in the microwave cavity. After 1 min of pre-stirring, the reaction was irradiated for 40 min to a set temperature of 100° C. After cooling to 40° C., the transparent solution was concentrated in vacuo, and the residual brown oil co-evaporated 3 times with acetonitrile to remove any residual water. The crude title compound in the form of a DIPEA salt, was immediately taken forward to the next step. LC/MS (Method A): $t_R$=1.29 min, >95%, m/z ($ESI^+$)=312($MH^+$).

Step c: 1-{[2-(Hex-5-enylmethylcarbamoyl)-4-hydroxycyclopentanecarbonyl]amino}-2-vinylcyclopropane carboxylic acid ethyl ester (1c)

The crude acid (1b) (5.5 mmol) was dissolved in DCM (50 ml) and DMF (14 ml) followed by addition of HATU (2.09 g, 5.5 mmol), hex-5-enyl-methyl-amine (678 mg, 6.0 mmol) and DIPEA (3.08 ml, 17.5 mmol) at room temperature. The reaction was stirred at ambient temperature for 1 h. LC/MS analysis showed complete conversion and the reaction mixture was concentrated in vacuo. The residue was re-dissolved in EtOAc (100 ml) and the organic layer washed with 0.1 M HCl (aq), $K_2CO_3$ (aq) and brine, dried ($MgSO_4$) and filtered. Evaporation of the solvent in vacuo gave an oil which was purified by flash chromatography (Silica, EtOAc:MeOH) to afford the title compound (1.65 g, 74%). TLC (Silica): MeOH:EtOAc 5:95, $R_f$=0.5; LC/MS (Method A): $t_R$=3.44 min, >95%, m/z ($ESI^+$)=407($MH^+$).

Step d: 1-{[4-Ethoxymethoxy-2-(hex-5-enyl-methyl-carbamoyl)-cyclopentanecarbonyl]-amino}-2-vinyl-cyclopropanecarboxylic acid ethyl ester (1d)

To a stirred solution of the diene 1c (7.94 g, 0.02 mol) in DCM and DIPEA (9.7 ml, 6 eq) at 0° C. (ice-bath) was added chloromethylethyl ether (2.79 g, 3 eq). The reaction mixture was stirred at room temperature overnight, concentrated by rotary evaporation and purified by column chromatography on silica gel (EtOAc/petroleum ether 1:1→1:0) which gave the pure title compound as slightly yellow syrup (6.67 g, 74%).

Step e: 17-Ethoxymethoxy-13-methyl-2,14-dioxo-3,13-diaza-tricyclo[13.3.0.0*4,6*]-octadec-7-ene-4-carboxylic acid ethyl ester (1e)

The diene (1d) (1.75 g) was dissolved in dry dichloroethane (800 ml, 0.0046M solution). The solution was bubbled with argon for 10 min whereafter Hoveyda-Grubbs 1:st gen. catalyst (20 mg 3.5 mol %) was added and the reaction mixture was stirred at 95° C. overnight. Additional catalyst (25 mg) was added to the reaction mixture (at argon flow) and the reaction was stirred at 97° C. The reaction mixture was cooled to room temperature and scavenger (100 mg) was added and reaction mixture was stirred for 4 h at room temperature. The reaction mixture was filtered, the filtrate was concentrated by rotary evaporation and the residue was purified by column chromatography on silica which gave the pure title compound (1.23 g. Yield 75%).

Step f: 17-Ethoxymethoxy-13-methyl-2,14-dioxo-3,13-diaza-tricyclo[13.3.0.0*4,6*]-octadec-7-ene-4-carboxylic acid (1f)

The ester 1e (2.26 g) was mixed with THF (20 ml), MeOH (20 ml) and a solution of LiOH (1N 20, ml) and stirred at 55° C. for ~17 h. The reaction mixture was concentrated by rotary evaporation, diluted with water (30-50 ml) and acidified with 10% citric acid to pH 3-4. The cloudy solution was extracted into ethyl acetate (3×50 ml). The combined organic extracts were washed with water and brine, and dried over magnesium sulfate. The drying agent was removed by filtration and the ethyl acetate was removed by rotary evaporation. The residue was dried on high vacuum which gave 2 g of the title compound as a white foam. The product was used directly without further purification.

Step g: Cyclopropanesulfonic acid (17-ethoxymethoxy-13-methyl-2,14-dioxo-3,13-diaza-tricyclo[13.3.0.0*4,6*]octadec-7-ene-4-carbonyl)-amide (1g)

The acid 1f was dissolved in dry DCM (20 ml). EDC (1.2 eq) was added and the reaction mixture was stirred for 3 h at room temperature LC-MS, showed full conversion of starting material. The solution was diluted with DCM and washed with water (3×20 ml). The water phase was extracted into DCM and the combined DCM extracts were washed with brine, dried over magnesium sulfate, filtered and concentrated by rotary evaporation which gave brownish syrup, which was used in the next step without additional purification.

The syrup was dissolved in dry DCM (20 ml) and cyclopropane sulfonamide (1.1 eq) was added to the solution followed by DBU. The solution was stirred at room temperature for 17 h. The reaction was monitored by LC-MS. The reaction mixture was diluted with DCM (70 ml) washed with 10% citric acid (2×20 ml) and brine, dried over magnesium sulfate, concentrated by rotary evaporation and purified by column chromatography on YCM silica (about 50 g, eluted with ether) which gave the pure title compound as a white foam (83%), (M+H)+ 512.

Step h: Cyclopropanesulfonic acid (17-hydroxy-13-methyl-2,14-dioxo-3,13-diaza-tricyclo[13.3.0.0*4,6*]octadec-7-ene-4-carbonyl)-amide (1h)

The ethoxy ether 1g was dissolved in a mixture of THF/MeOH/water (1:1:1, total volume 30 ml) whereafter 2.5 ml conc. hydrochloric acid was added while stirring. The reaction was stirred overnight at room temperature and was monitored by LC-MS. The reaction mixture was then poured into sat. aq. NaHCO₃ (50 ml) and concentrated to half of the volume by rotary evaporation. The resulting mixture was acidified with 10% citric acid and extracted into DCM (3×20 ml). The combined organic phases were washed with brine, dried over magnesium sulfate, filtered and concentrated by rotary evaporation and dried at high vacuum overnight. The product was used without additional purification.

Step i: (2-Cyanophenyl)-carbamic acid 4-cyclopropanesulfonylaminocarbonyl-13-methyl-2,14-dioxo-3,13-diaza-tricyclo[13.3.0.0*4,6*]octadec-7-en-17-yl ester (1i)

The alcohol 1h (11 mg) was dissolved in dry dichloromethane (2 ml) and 2-isocyanbenzonitrile (2 eq) was added followed by triethylamine (5 µl). The reaction mixture was stirred overnight at room temperature and then concentrated by rotary evaporation. Purification of the residue by prep HPLC (water/acetonitrile with 0.1% TFA, grad 30-80) gave the title compound (5 mg, 27%), [M+H]⁻ 598.

Example 2

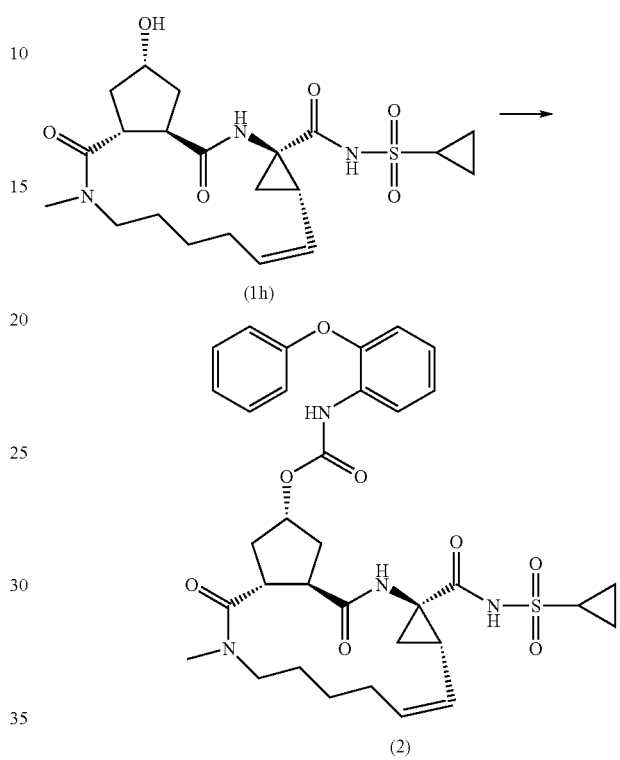

(2-Phenoxyphenyl)-carbamic acid 4-cyclopropane-sulfonylaminocarbonyl-13-methyl-2,14-dioxo-3,13-diaza-tricyclo[13.3.0.0*4,6*]octadec-7-en-17-yl ester (2)

The alcohol 1h (11 mg) was reacted according to the procedure described in Example 1 Step i but using 2-isocyanophenoxybenzene ester instead of 2-isocyanbenzonitrile, which gave the title compound (10 mg, 63%), [M+H]+ 665.

Example 3

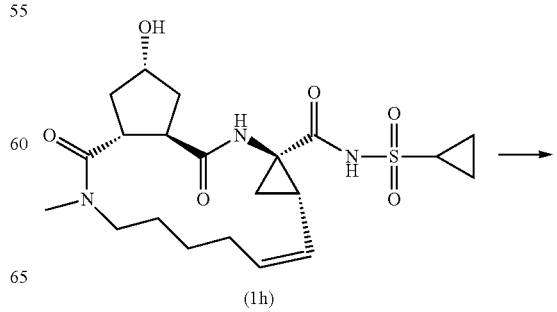

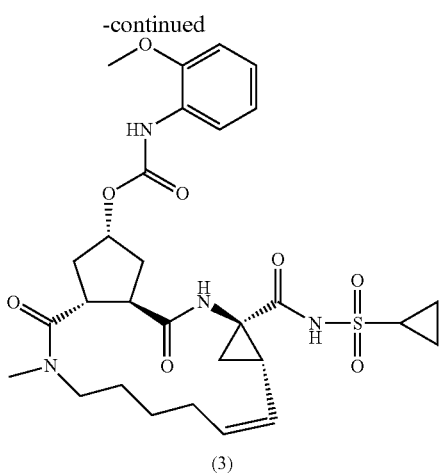

(3)

(2-Methoxy-phenyl)-carbamic acid 4-cyclopropane-sulfonylaminocarbonyl-13-methyl-2,14-dioxo-3,13-diaza-tricyclo[13.3.0.0*4,6*]octadec-7-en-17-yl ester (3)

The alcohol 1h (11 mg) was reacted according to the procedure described in Example 1 Step i but using 2-isocyanomethoxybenzene ester instead of 2-isocyanbenzonitrile, which gave the title compound (9 mg, 58%), [M+H]+ 603.

Example 4

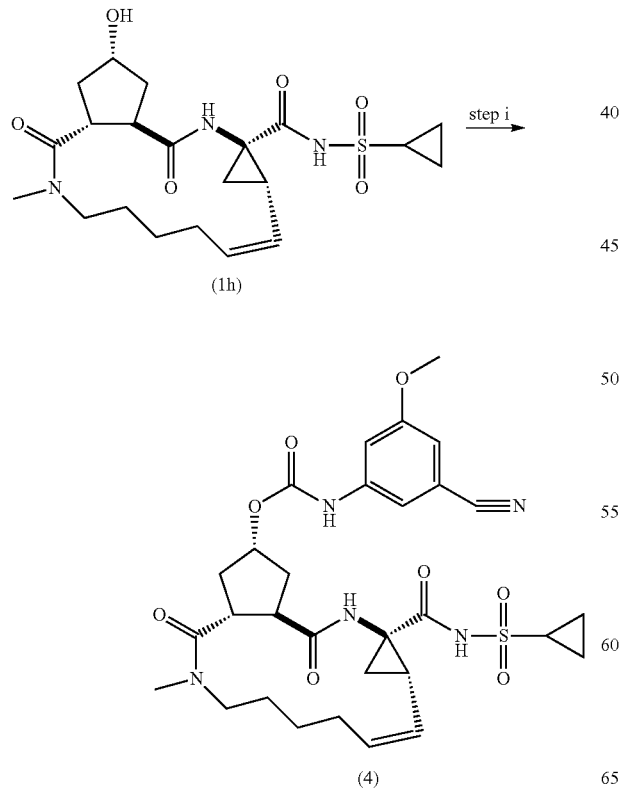

(3-Cyano-5-methoxy-phenyl)-carbamic acid 4-cyclopropanesulfonylaminocarbonyl-13-methyl-2,14-dioxo-3,13-diaza-tricyclo[13.3.0.0*4,6*]octadec-7-en-17-yl ester (4)

The alcohol 1h (15 mg) was dissolved in dry DCE and 20 mg of sodium bicarbonate was added, followed by 2 ml of a phosgene solution in toluene (20%). The reaction mixture was stirred at room temperature for 3 h (full conversion to chloroimidate according to LC-MS) and then concentrated by rotary evaporation and dried from excess of phosgene in high vacuum (1.5 h). The dry reaction mixture was transferred into a "microwave" vial (2-5 ml), mixed with dry DCE (3 ml), 3-amino-5-methoxy-benzonitrile (2 eq), potassium carbonate (9 mg, 1.5 eq), pulverized molecular sieves (4 Å, 5 mg) and heated in a microwave at 100° C. for 45 min. The reaction mixture was passed through short pad of silica (eluent DCM, then 10% methanol in DCM). The resulting fractions containing the desired carbamate compound were combined, concentrated by rotary evaporation and purified by column chromatography on YMC silica (15 g, ethyl acetate/petroleum ether 1:3 to remove excess of aniline, followed by dichloromethane and then 2% methanol in dichloromethane) to give the title compound as a powder (15 mg, 8%), [M+H]+ 628.

Example 5

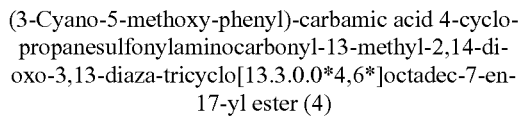

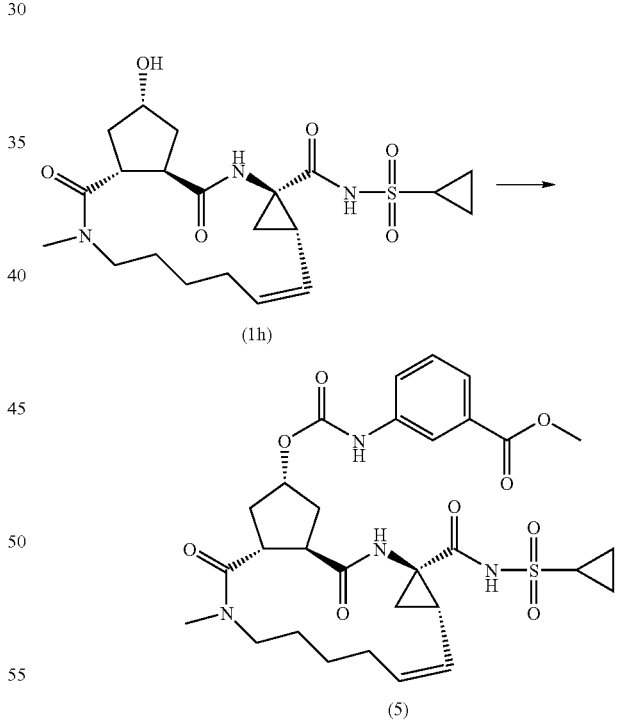

3-(4-Cyclopropanesulfonylaminocarbonyl-13-methyl-2,14-dioxo-3,13-diaza-tricyclo-[13.3.0.0*4,6*]octadec-7-en-17-yloxycarbonylamino)-benzoic acid methyl ester (5)

The alcohol 1h (20 mg) was reacted according to the procedure described in Example 1 Step i but using 3-aminobenzoic acid methyl ester instead of 3-amino-5-methoxy-benzonitrile, which gave the title compound (10 mg, 36%), [M+H]+ 631.

Example 6

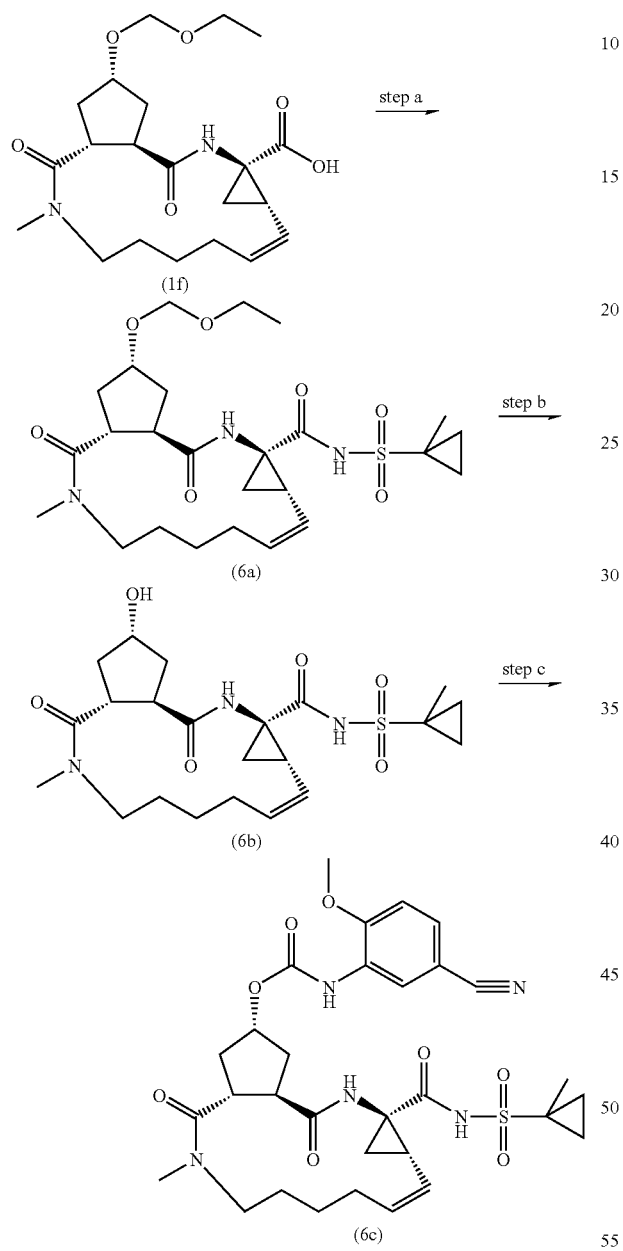

Step a: 1-Methyl-cyclopropanesulfonic acid (17-ethoxymethoxy-13-methyl-2,14-dioxo-3,13-diaza-tricyclo[13.3.0.0*4,6*]octadec-7-ene-4-carbonyl)-amide (6a)

The acid 1f was reacted according to the procedure described in Example 1 Step g but using methylcyclopropanesulphone amide instead of cyclopropanesulphone amide which gave the title compound.

Step b: 1-Methylcyclopropanesulfonic acid (17-hydroxy-13-methyl-2,14-dioxo-3,13-diaza-tricyclo[13.3.0.0*4,6*]octadec-7-ene-4-carbonyl)-amide (6b)

The ethoxy ether 3a was treated according to the procedure described in Example 1 Step h, which gave the title compound.

Step c: (5-Cyano-2-methoxy-phenyl)-carbamic acid 13-methyl-4-(1-methyl-cyclopropanesulfonylaminocarbonyl)-2,14-dioxo-3,13-diaza-tricyclo[13.3.0.0*4,6*]-octadec-7-en-17-yl ester (6c)

The alcohol 3b (30 mg) was reacted according to the procedure described in Example 1 Step i but using 3-amino-4-methoxybenzonitrile instead of 3-amino-5-methoxy-benzonitrile, which gave the title compound (12 mg, 33%), [M+H]+ 642.

Example 7

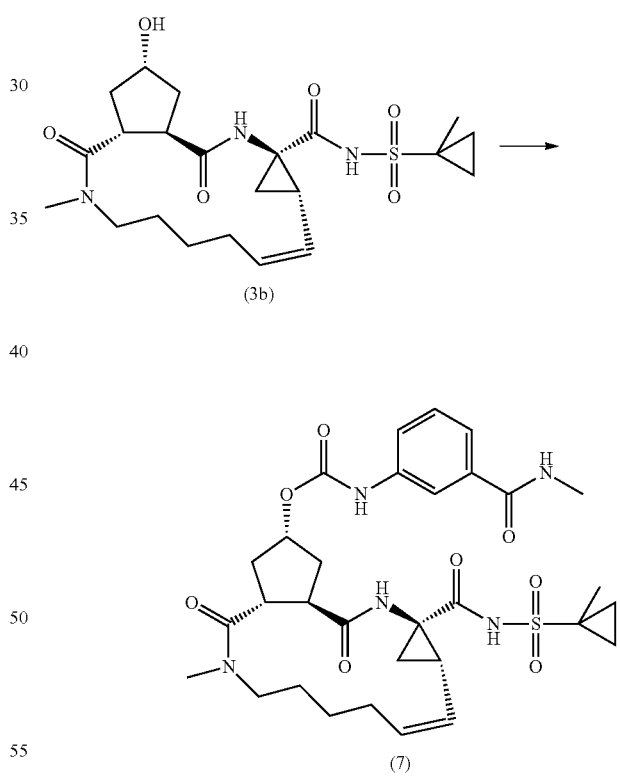

(3-Methylcarbamoyl-phenyl)-carbamic acid 13-methyl-4-(1-methyl-cyclopropane-sulfonylaminocarbonyl)-2,14-dioxo-3,13-diaza-tricyclo[13.3.0.0*4,6*] octadec-7-en-17-yl ester (7)

The alcohol 3b (34 mg) was reacted according to the procedure described in Example 1 Step i_but using_3-amino- N-methylbenzamide instead of 3-amino-5-methoxy-benzonitrile, which gave the title compound (8 mg, 19%), [M+H]+ 644.

Example 8

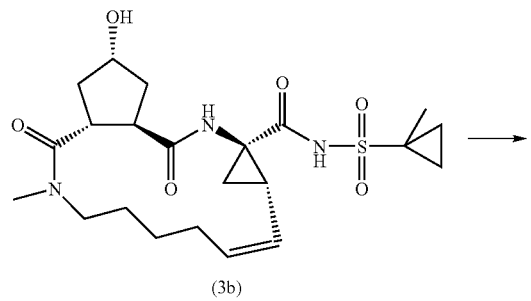
(3b)

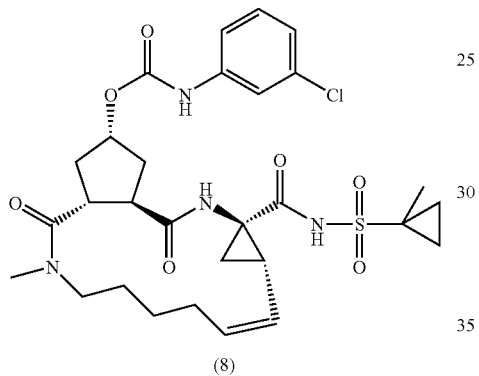
(8)

(3-Chloro-phenyl)-carbamic acid 4-(1-methylcyclopropanesulfonylaminocarbonyl)-13-methyl-2,14-dioxo-3,13-diaza-tricyclo[13.3.0.0*4,6*]octadec-7-en-17-yl ester (5)

The alcohol 3b (35 mg) was reacted according to the procedure described in Example 1 Step i_but using_3-chloroaniline instead of 3-amino-5-methoxybenzonitrile, which gave the title compound (27 mg, 66%), [M+H]+ 622.

Example 9

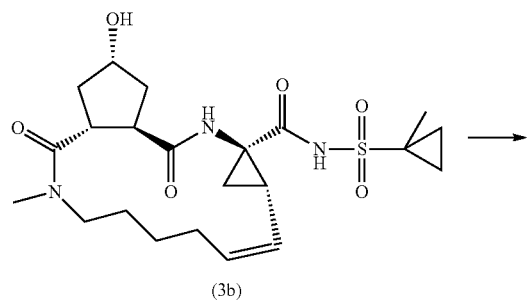
(3b)

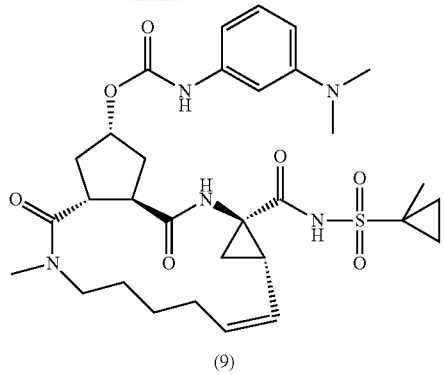
(9)

(3-Dimethylaminophenyl)-carbamic acid 13-methyl-4-(1-methyl-cyclopropane-sulfonylaminocarbonyl)-2,14-dioxo-3,13-diaza-tricyclo[13.3.0.0*4,6*]octadec-7-en-17-yl ester (6)

The alcohol 3b (80 mg) was reacted according to the procedure described in Example 1, Step i, but using 3-dimethylaminoaniline instead of 3-amino-5-methoxybenzonitrile which gave the title compound (50 mg, 40%), [M+H]+ 63.

Example 10

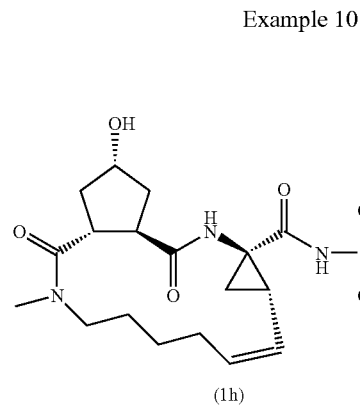
(1h)

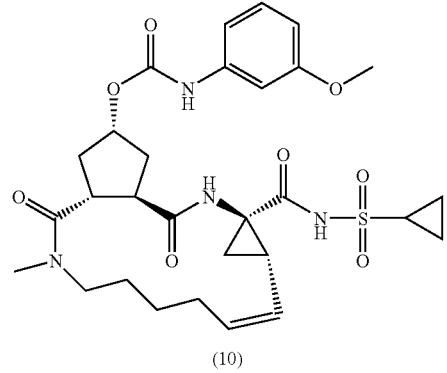
(10)

(3-Methoxyphenyl)-carbamic acid 4-cyclopropanesulfonylaminocarbonyl-13-methyl-2,14-dioxo-3,13-diaza-tricyclo[13.3.0.0*4,6*]octadec-7-en-17-yl ester (10)

The alcohol 1h (6 mg) was dissolved in dry dichloromethane (2 ml) and 3-isocyanomethoxybenzene (2 eq) was added followed by triethylamine (5 µl). The reaction mixture was stirred overnight at room temperature and then concentrated by rotary evaporation. Purification of the residue by prep HPLC (water/acetonitrile with 0.1% TFA, grad 30-80) gave the title compound (2 mg, 27%), [M+H]⁻ 603.

Example 11

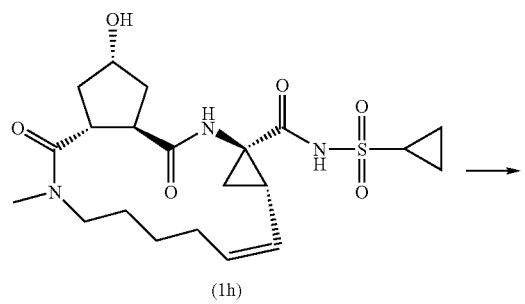

(1h)

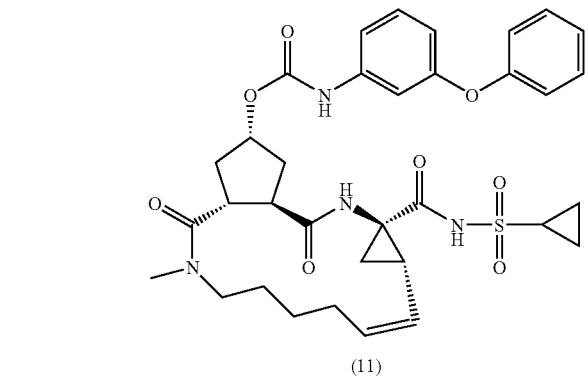

(11)

(3-Phenoxy-phenyl)-carbamic acid 4-cyclopropane-sulfonylaminocarbonyl-13-methyl-2,14-dioxo-3,13-diaza-tricyclo[13.3.0.0*4,6*]octadec-7-en-17-yl ester (11)

The alcohol 1h (10 mg) was reacted according to the procedure described in Example 1 Step i but using 3-isocyanophenoxybenzene instead of 3-isocyanomethoxybenzene, which gave the title compound (11 mg, 72%), [M+H]⁺ 665.

Example 12

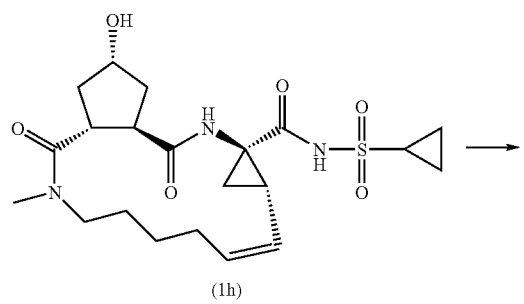

(1h)

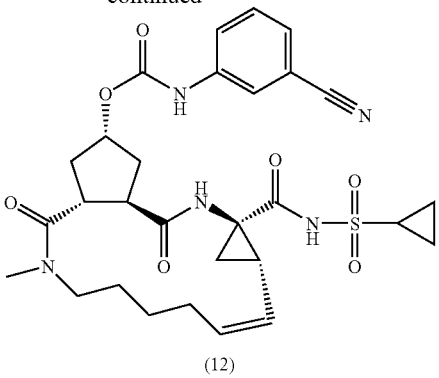

(12)

(3-Cyano-phenyl)-carbamic acid 4-cyclopropane-sulfonylaminocarbonyl-13-methyl-2,14-dioxo-3,13-diaza-tricyclo[13.3.0.0*4,6*]octadec-7-en-17-yl ester (12)

The alcohol 1h (10 mg) was reacted according to the procedure described in Example 1 Step i but using 3-isocyanobenzonitrile instead of 3-isocyanomethoxybenzene, which gave the title compound (10 mg, 75%), [M+H]⁺ 598.

Example 13

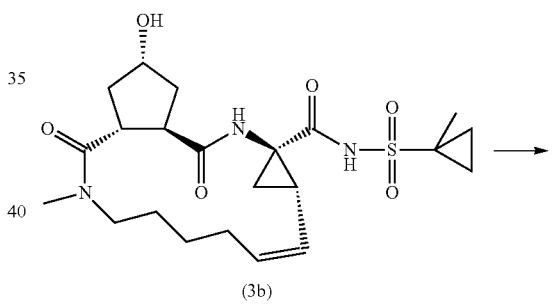

(3b)

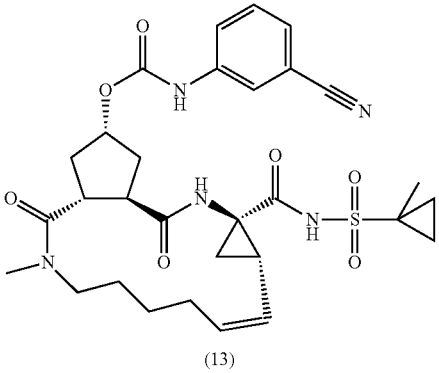

(13)

(3-Cyanophenyl)-carbamic acid 13-methyl-4-(1-methylcyclopropanesulfonylamino-carbonyl)-2,14-dioxo-3,13-diaza-tricyclo[13.3.0.0*4,6*]octadec-7-en-17-yl ester (13)

The alcohol 3b (20 mg) was reacted according to the procedure described in Example 7 Step i but using 3-isocyanobenzonitrile instead of 3-isocyanomethoxybenzene, which gave the title compound (13 mg, 51%), [M+H]⁺ 612.

Example 14

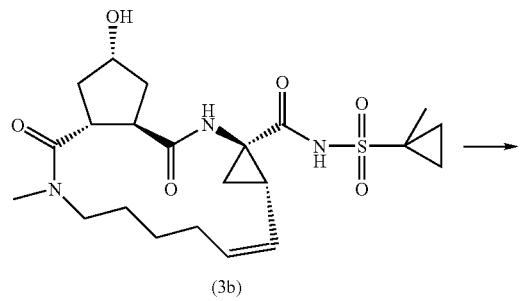

(3b)

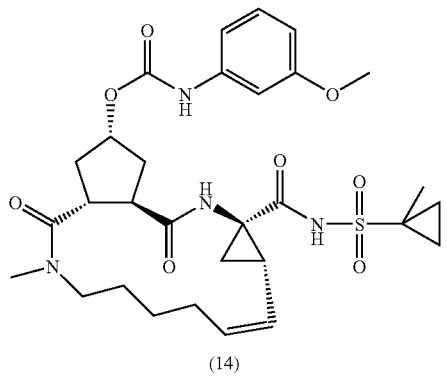

(14)

(3-Methoxy-phenyl)-carbamic acid 13-methyl-4-(1-methyl-cyclopropanesulfonyl-aminocarbonyl)-2,14-dioxo-3,13-diaza-tricyclo[13.3.0.0*4,6*]octadec-7-en-17-yl ester (14)

The alcohol 3b (18 mg) was reacted according to the procedure described in Example 7 Step i, which gave the title compound (14 mg, 59%), [M+H]⁻ 617.

Example 15

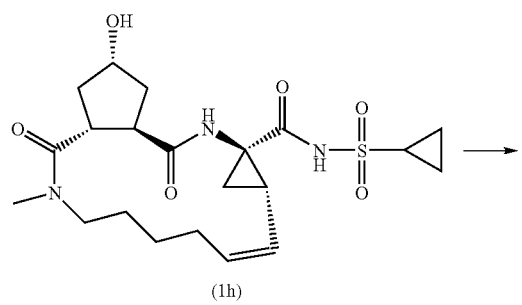

(1h)

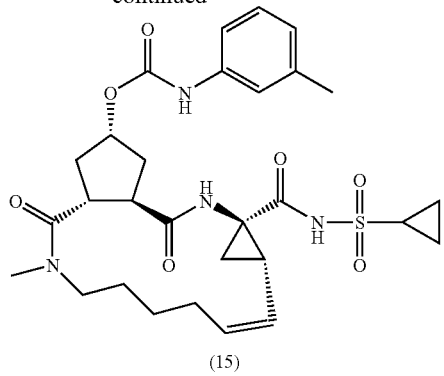

(15)

m-Tolyl-carbamic acid 4-cyclopropanesulfonylaminocarbonyl-13-methyl-2,14-dioxo-3,13-diaza-tricyclo[13.3.0.0*4,6*]octadec-7-en-17-yl ester (15)

The alcohol 1h (17 mg) was reacted according to the procedure described in Example 1 Step i but using 3-isocyanotoluene instead of 3-isocyanomethoxybenzene, which gave the title compound (6 mg, 26%), [M+H]⁺ 587.

Example 16

(1h)

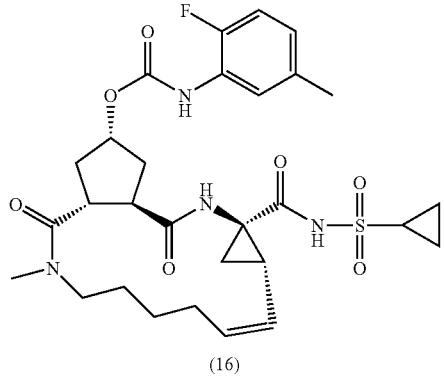

(16)

(2-Fluoro-5-methyl-phenyl)-carbamic acid 4-cyclopropanesulfonylaminocarbonyl-13-methyl-2,14-dioxo-3,13-diaza-tricyclo[13.3.0.0*4,6*]octadec-7-en-17-yl ester (16)

The alcohol 1h (23 mg) was reacted according to the procedure described in Example 1 Step i but using 4-fluoro-3- isocyanotoluene instead of 3-isocyanomethoxybenzene, which gave the title compound (14 mg, 46%), [M+H]+ 605.

Example 17

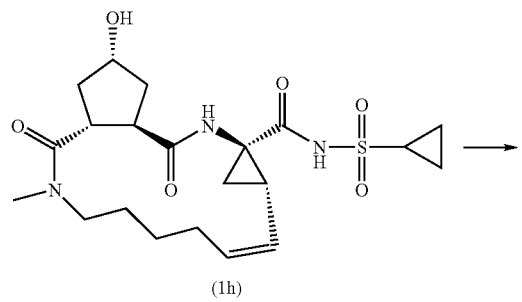

(1h)

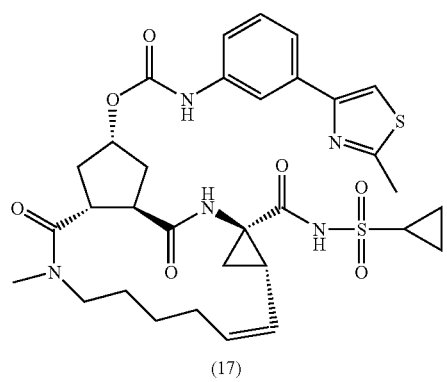

(17)

[3-(2-Methyl-thiazol-4-yl)-phenyl]-carbamic acid 4-cyclopropanesulfonylamino-carbonyl-13-methyl-2, 14-dioxo-3,13-diaza-tricyclo[13.3.0.0*4,6*]octadec-7-en-17-yl ester (17)

The alcohol 1h (30 mg) was reacted according to the procedure described in Example 1 Step i but using 4-(3-isocyanophenyl)-2-methyl-thiazole instead of 3-isocyanomethoxy-benzene, which gave the title compound (19 mg, 49%), [M+H]+ 670.

Example 18

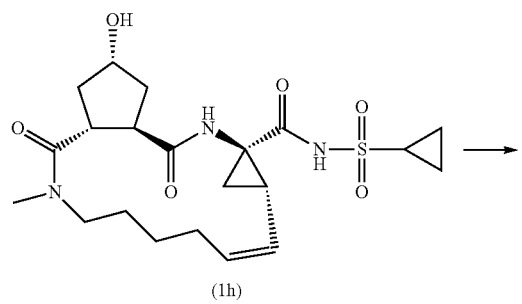

(1h)

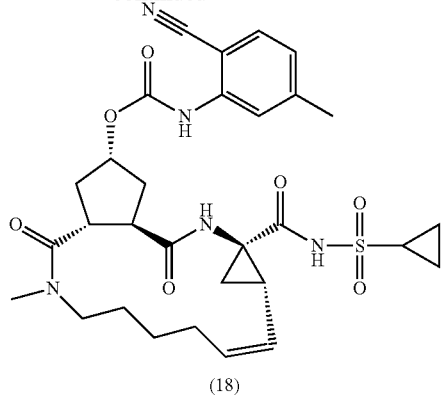

(18)

(2-Cyano-5-methyl-phenyl)-carbamic acid 4-cyclopropanesulfonylaminocarbonyl-13-methyl-2,14-dioxo-3,13-diaza-tricyclo[13.3.0.0*4,6*]octadec-7-en-17-yl ester (18)

The alcohol 1h (30 mg) was reacted according to the procedure described in Example 1 Step i but using 2-amino-4-methylbenzonitrile instead of 3-amino-5-methoxy-benzonitrile, which gave the title compound (25 mg, 70%).

Example 19

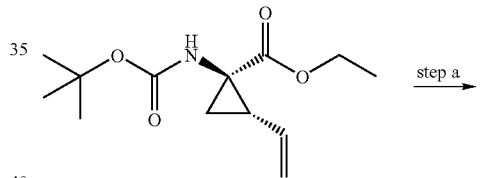

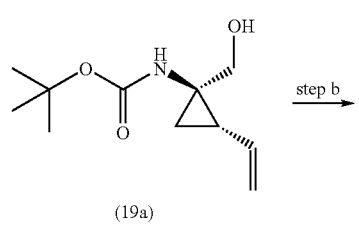

(19a)

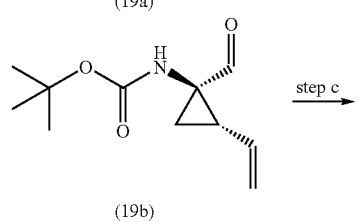

(19b)

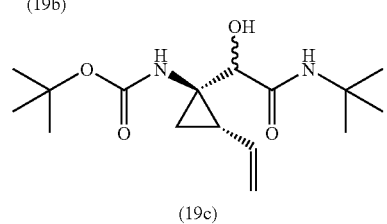

(19c)

Step a: (1-Hydroxymethyl-2-vinylcyclopropyl)-carbamic acid tert-butyl ester (19a)

To a solution of 1-tert-butoxycarbonylamino-2-vinyl-cyclopropanecarboxylic acid ethyl ester (0.51 g, 2.0 mmol) in THF (10 ml) at 0° C. was added a 2M solution of lithiumborohydride (4 ml, 8 mmol). The reaction mixture was monitored by TLC (7:3 hexane-ethyl acetate, stained using ammoniummolybdate-cerium sulfate in aq. 10% sulfuric acid) and after stirring overnight at rt, the reaction was carefully quenched using aq. 10% citric acid (25 ml, dropwise addition at 0° C.). The obtained mixture was washed with dichloromethane (3×10 ml), and the combined org. layers were dried ($Na_2SO_4$), filtered and concentrated. Flash chromatography of the residue using 1:1 hexane-ethyl acetate as eluent, followed by concentration of the appropriate fractions and drying the residue in vacuum overnight, gave the product as a colorless syrup (0.407 g, 1.91 mmol, 96%).

NMR data (400 MHz, $CDCl_3$): $^1H$, δ 0.98 (m, 1H), 1.15 (m, 1H), 1.44 (s, 9H), 1.84 (m, 1H), 3.20 (brs, 1H), 3.60 (dd, 1H), 3.78 (brm, 1H), 5.10-5.26 (m, 3H), 5.70 (m, 1H).

Step b: (1-Formyl-2-vinyl-cyclopropyl)-carbamic acid tert-butyl ester (19b)

To a stirred solution of the alcohol 19a (0.152 g, 0.71 mmol) in dichloromethane (5 ml) was added Dess-Martin periodinane (0.33 g, 0.78 mmol) at rt. The reaction was monitored by TLC (3:2 Hexane-ethyl acetate, UV-monitoring and staining using ammoniummolybdate-cerium sulfate in aq. 10% sulfuric acid). Staining indicates a fairly clean reaction, but UV monitoring indicates several byproducts. After 1 h the obtained yellow-red solution was diluted with dichloromethane (20 ml), then washed with 1:1 aq. 10% sodium thiosulfate/aq. saturated sodium hydrogen carbonate (3×20 ml), then dried ($Na_2SO_4$), filtered and concentrated. Flash chromatography of the residue using stepwise gradient elution (ethyl acetate in hexane 20-30%) followed by concentration of the appropriate fractions and drying the residue in vacuum overnight, gave the title compound as a colorless oil (0.054 g, 0.255 mmol, 36%).

Step c: [1-(tert-Butylcarbamoyl-hydroxy-methyl)-2-vinyl-cyclopropyl]-carbamic acid tert-butyl ester (19c)

To a solution of the aldehyde 19b (0.054 g, 0.255 mmol) and tert-butylisonitrile (0.043 ml, 0.38 mmol) in dichloromethane (1 ml) and pyridine (0.083 ml, 1.02 mmol) under nitrogen was added trifluoroacetic acid (0.039 ml, 0.51 mmol). After 30 min at rt, the reaction mixture was allowed to reach rt and was stirred for another 2 days. TLC (7:3 hexane-ethyl acetate) and LC-MS monitoring then indicated approx 60% conversion and the reaction mixture was diluted with ethyl acetate (10 ml). The solution was washed successively with aq. 10% citric acid (3×5 ml) and aq. saturated sodium hydrogen carbonate (3×5 ml), then dried ($Na_2SO_4$), filtered and concentrated. The residue was then treated with 1:1:1 aq. 1M LiOH/THF/MeOH (1.5 ml) for 10 min at rt, then diluted with aq. 10% citric acid and taken into ethyl acetate, then dried ($Na_2SO_4$), filtered and concentrated. Column chromatography of the residue using 7:3 hexane-ethyl acetate as eluent followed by concentration of the appropriate fractions and drying the residue in vacuum overnight, gave the product as a colorless solid (0.027 g, 0.086 mmol, 34%).

NMR data (400 MHz, $CDCl_3$): $^1H$, δ 1.24 (m, 1H), 1.33-1.40 (m, 10H), 1.44 (s, 9H), 1.87 (m, 1H), 3.65 (d, 1H), 5.21 (m, 3H), 5.50 (d, 1H), 5.89 (m, 1H), 7.03 (brs, 1H).

α-Hydroxyamide derivatives of the compounds of formula (I) of the invention are then obtained by removing the N-BOC group from the title compound followed by coupling of the afforded amine to an acid, such as the acid 1f, according to the procedure described in Example 1 step g, followed by removal of the hydroxy protecting group and a carbamoylation reaction as described in Example 1 step h and i respectively.

General Procedure for Oxidizing α-Hydroxyamides into α-Ketoamides:

Typically the α-hydroxyamide is dissolved in dichloromethane (20-30 ml/g) at rt, then Dess-Martin Periodinane (1.1 equivalents) is added and the reaction mixture is monitored by TLC and LC-MS. After or near completion of the reaction the reaction mixture is diluted with dichloromethane and then washed with 1:1 aq. 10% sodium thiosulphate/aq. saturated sodium hydrogen carbonate (3 times), then dried ($Na_2SO_4$), filtered and concentrated. The residue is purified by column chromatography or preparative-LC.

Example 20

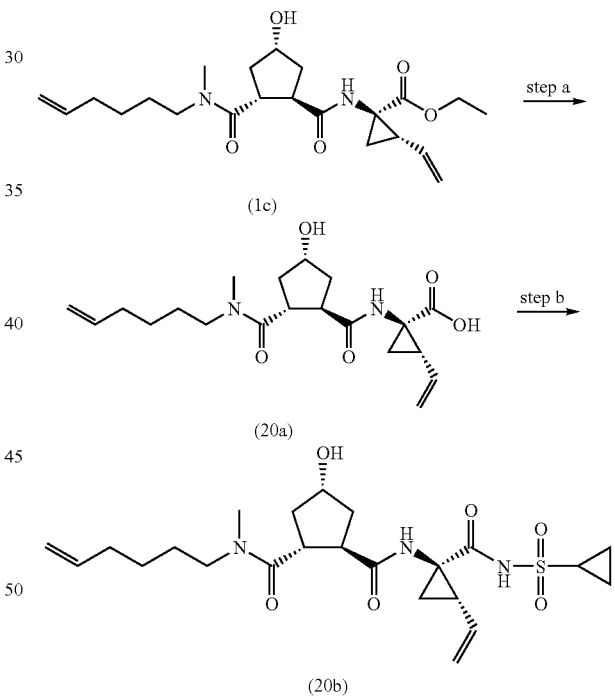

Step a: 1-{[2-(Hex-5-enylmethylcarbamoyl)-4-hydroxycyclopentanecarbonyl]amino}-2-vinylcyclopropanecarboxylic acid (20a)

Compound 1c (493 mg, 1.21 mmol) was dissolved in DMF (1 ml) and transferred to a 20 ml microwave reaction vessel. Then, aqueous LiOH (2 M, 10.5 ml) and a stirbar were added. The reaction vessel was sealed and the immiscible slurry was shaken vigorously before insertion in the microwave cavity. The reaction was irradiated for 30 min to 130° C. The reaction mixture was cooled to 40° C. and the clear solution acidified to pH 2 with aqueous HCl (1 M, 24 ml) and extracted 3 times with EtOAc (20 ml). The pooled organic layers were washed with brine, dried (MgSO$_4$) and filtered. The solvent was evaporated in vacuo to afford the title compound (410 mg, 90%). LC/MS >95%, m/z (ESI$^+$)=379(MH$^+$).

Step b: 2-(Hex-5-enyl-methyl-amino-carbonyl)-4-hydroxy-cyclopentanecarboxylic acid (1-cyclopropanesulfonylamino carbonyl-2-vinyl-cyclopropyl)-amide (20b)

The crude acid 20a (410 mg, 1.09 mmol) was dissolved in DMF (1.5 ml) and DCM (4.5 ml) followed by addition of EDAC (417 mg, 2.18 mmol) at room temperature. The mixture was allowed to incubate with stirring at room temperature. After 10 min, DMAP (133 mg, 1.09 mmol) was added followed by another 20 min incubation at room temperature. Subsequently, a pre-mixed solution of cyclopropanesulfonic acid amide (527 mg, 4.36 mmol) and DBU (663 mg, 4.36 mmol) in DMF (2 ml) and DCM (2 ml) was added followed by heating in the microwave to 100° C. for 30 min. The resulting red solution was concentrated in vacuo and re-dissolved in EtOAc (20 ml). The organic phase was washed with 1 M HCl (aq) (3×10 ml) and brine (10 ml), dried (MgSO$_4$) and filtered. The solvent was evaporated in vacuo to yield the crude sulfonamide which was further purified by chromatography (Silica, EtOAc/MeOH, 97.5:2.5) to afford the title compound (403 mg, 77%); LC/MS, >95%, m/z (ESI$^+$)=482 (MH$^+$)

Compounds of formula (I) can be obtained from intermediate 20b by performing a carbamoylation reaction using any of the methods described above, for example as described in Example 1 step i, or in Example 10, followed by a ring closing metathesis reaction as described in Example 1 step e.

Example 21

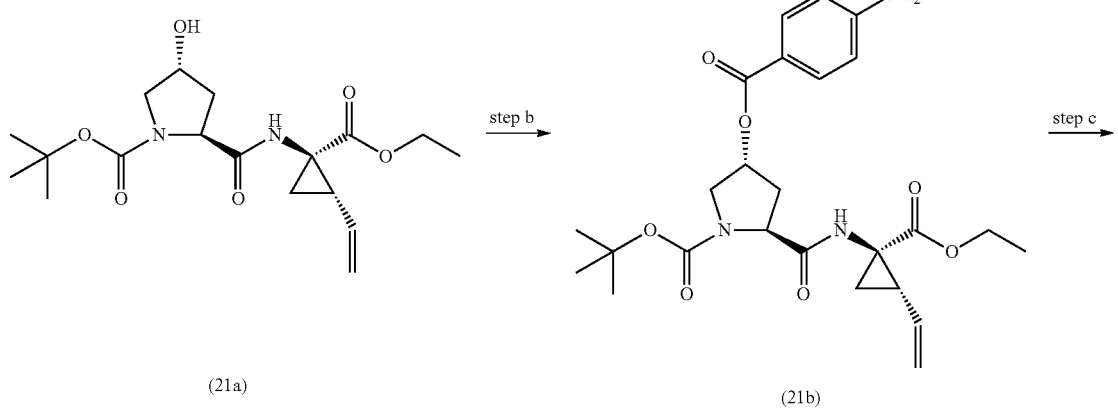

(21a) (21b)

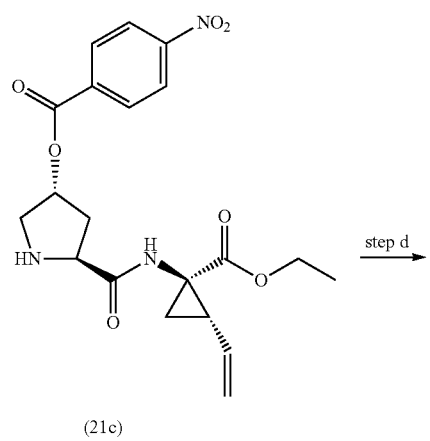

(21c)

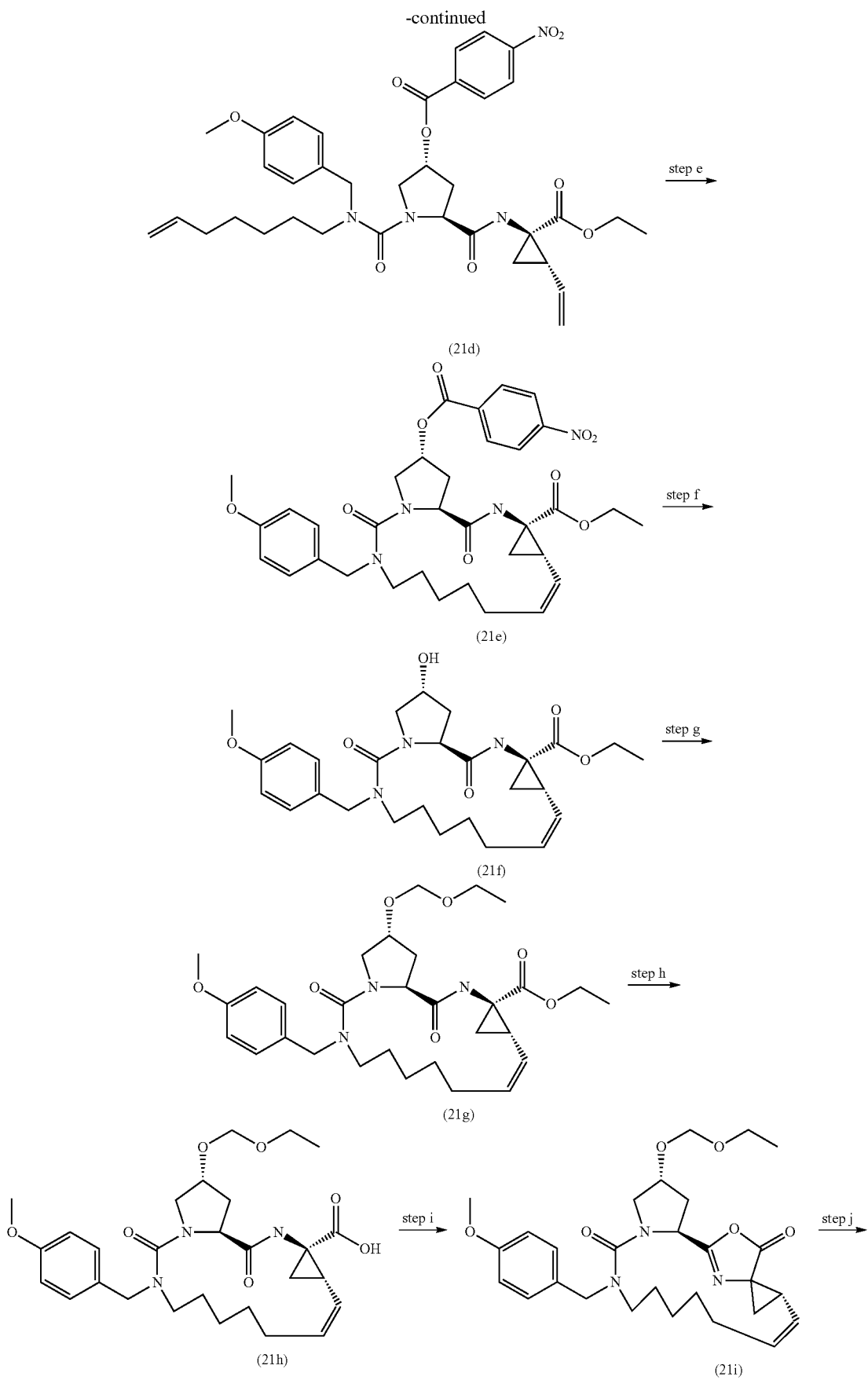

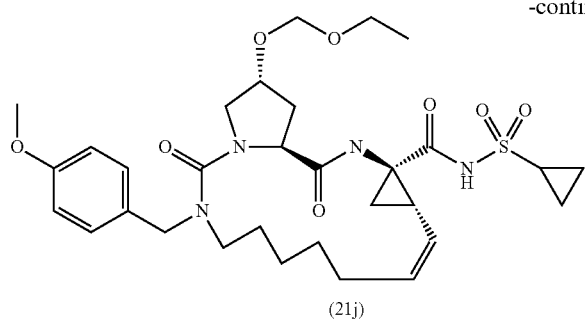

(21j)

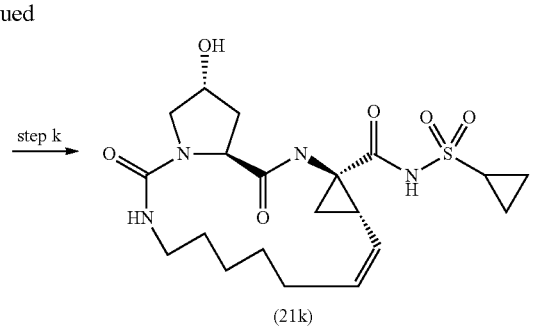

(21k)

Step a: 2-(1-Ethoxycarbonyl-2-vinyl-cyclopropylcarbamoyl)-4-hydroxy-pyrrolidine-1-carboxylic acid tert-butyl ester (21a)

Boc-protected 4-hydroxy proline (4 g, 17.3 mmol), HATU (6.9 g, 18.2 mmol) and 1-amino-2-vinyl-cyclopropanecarboxylic acid ethyl ester prepared as described in WO03/099274, (3.5 g, 18.3 mmol) were dissolved in DMF (60 ml) and cooled to 0° C. on an ice-bath. Diisopropylethyl amine (DIPEA) (6 ml) was added. The ice-bath was removed and the mixture was left at ambient temperature over-night. Dichloromethane (~80 ml) was then added and the organic phase was washed with aqueous sodium hydrogen carbonate, citric acid, water, brine and dried over sodium sulfate. Purification by flash chromatography (ether→7% methanol in ether) gave pure title compound (6.13 g, 96%)

Step b: 2-(1-Ethoxycarbonyl-2-vinyl-cyclopropylcarbamoyl)-4-(4-nitro-benzoyloxy)-pyrrolidine-1-carboxylic acid tert-butyl ester (21b)

Compound 21a (11.8 g, 32.0 mmol) and pyridine (27 ml, 305 mmol) were dissolved in DCM (200 ml) and cooled to 0° C., 4-nitrobenzoyl chloride (6.6 g, 35.6 mmol) was added and the solution was stirred at room temperature overnight. The reaction mixture was washed with $NaHCO_3$ (aq), aqueous citric acid and brine, dried over $MgSO_4$ and evaporated on silica. The crude product was purified by column chromatography on silica (EtOAc/n-Heptane: 50:50) to give 11.84 g, 72% of the title compound.

Step c: 4-Nitro-benzoic acid 5-(1-ethoxycarbonyl-2-vinyl-cyclopropylcarbamoyl)-pyrrolidin-3-yl ester (21c)

Compound 21b (11.84 g, 22.9 mmol) was deprotected in TFA (30 ml) dissolved in DCM (100 ml) and then worked up by methods known in the chemical art to give the title compound (9.37 g, 98%).

Step d: 4-Nitro-benzoic acid 5-(1-ethoxycarbonyl-2-vinyl-cyclopropylcarbamoyl)-1-[hept-6-enyl-(4-methoxy-benzyl)-carbamoyl]-pyrrolidin-3-yl ester (21d)

The amine 21c (4.68 g, 11.2 mmol) was dissolved in THF (100 ml), $NaHCO_3$ (s) (appr. 5 ml) was added followed by phosgene-solution (20% in toluene, 11.6 ml, 22.5 mmol). The reaction mixture was stirred vigorously for 1h and then filtrated, evaporated and redissolved in DCM (100 ml). $NaHCO_3$ (s) (appr. 5 ml) was added followed by hept-6-enyl-(4-methoxy-benzyl)-amine (3.92 g, 16.8 mmol). The reaction mixture was stirred at room temperature overnight, filtrated and evaporated on silica. The crude product was purified by column chromatography on silica (EtOAc/n-Heptane: 25/75) to give the title compound (6.9 g, 91%).

Step e: 14-(4-Methoxy-benzyl)-18-(4-nitro-benzoyloxy)-2,15-dioxo-3,14,16-triaza-tricyclo[14.3.0.0*4,6*]nonadec-7-ene-4-carboxylic acid ethyl ester (21e)

The diene 21d (406 mg, 0.6 mmol) was dissolved in DCE (250 ml) and degassed. Hoveyda-Grubbs Catalyst $2^{nd}$ generation (26 mg, 0.042 mmol) was added and the solution was heated to reflux. After 3 h the solution was evaporated and used direct in the next step.

Step f: 18-Hydroxy-14-(4-methoxy-benzyl)-2,15-dioxo-3,14,16-triaza-tricyclo-[14.3.0.0*4,6*]nonadec-7-ene-4-carboxylic acid ethyl ester (21f)

Crude compound 21e (445 mg) was dissolved in THF (20 ml), MeOH (10 ml) and water (10 ml). After cooling to 0° C. 1M LiOH (2 ml) was added. After 1.5 h the hydrolysis was completed and HOAc (1 ml) was added and the solution was evaporated to appr 10 ml. Water was added and the mixture was extracted with DCM (2×30 ml). The pooled organic phase was washed with $NaHCO_3$ (aq), water, brine and dried over MgSO4. The crude product was purified by column chromatography on silica (DCM/MeOH: 100/0-80/20) to give the title compound (201 mg, 67%).

Step g: 18-Ethoxymethoxy-14-(4-methoxy-benzyl)-2,15-dioxo-3,14,16-triaza-tricyclo[14.3.0.0*4,6*]nonadec-7-ene-4-carboxylic acid ethyl ester (21g)

To a stirred solution of the alcohol 21f (1.35 g, 2.70 mmol, 75% purity) and N-ethyldiisopropylamine (1.42 ml, 8.1 mmol) in dichloromethane (15 ml) at 0° C. was added chloromethyl ethyl ether (0.5 ml, 5.4 mmol). After stirring at rt on the reaction mixture was cooled to 0° C. and more N-ethyldiisopropylamine (1 ml, 5.7 mmol) and chloromethyl ethyl ether (0.3 ml, 3.2 mmol) was added, then stirred additional 16 h at rt. The reaction mixture was then directly applied on a silicagel column and eluted using stepwise gradient elution (ethyl acetate in hexane 50-80%). Concentration of the appropriate fractions gave the title compound as a slight brown syrup which crystallized upon standing (0.8 g, 53%). LR-MS: Calcd for $C_{30}H_{44}N_3O_7$: 558. Found: 558 [M+H].

Step h: 18-Ethoxymethoxy-14-(4-methoxy-benzyl)-2,15-dioxo-3,14,16-triaza-tricyclo[14.3.0.0*4,6*] nonadec-7-ene-4-carboxylic acid (21h)

A solution of the ester 21g (0.775 g, 1.39 mmol) in 1:1:1 THF-Methanol-aq. 1M LiOH (36 ml) was stirred at rt for 3.5 h after which TLC (95:5 and 9:1 dichloromethane-methanol) and LC-MS indicated complete conversion into the carboxylic acid. The reaction mixture was then concentrated into approximately ⅓ of the volume, then diluted with water (10 ml) and acidified to approx. pH 4 using aq. 10% citric acid (60 ml) upon which a precipitate formed. The mixture was washed with ethyl acetate (3×25 ml) and the combined organic layers were washed with brine (2×50 ml), then dried (Na$_2$SO$_4$), filtered and concentrated. The residue was concentrated from toluene (3×10 ml) which gave the crude title compound as an off-white foam (0.75 g, quantitative). LR-MS: Calcd for $C_{28}H_{40}N_3O_7$: 530. Found: 530 [M–H].

Step i: Compound 21i

To a solution of the carboxylic acid 21h (approx. 1.39 mmol) in dichloromethane (10 ml) at rt was added N-Ethyl-N'-(3-dimethylaminopropyl)carbodiimide×HCl (0.32 g, 1.67 mmol), then stirred overnight after which LC-MS indicated complete conversion of the acid into the product. The reaction mixture was then diluted with dichloromethane (10 ml), washed with water (3×10 ml), then dried (Na$_2$SO$_4$) filtered and concentrated into a colorless solid (crude yield: 0.7 g) which was used immediately in the next step. LR-MS: Calcd for $C_{28}H_{38}N_3O_6$: 512. Found: 512 [M+H].

Step j: Cyclopropanesulfonic acid [18-ethoxymethoxy-14-(4-methoxy-benzyl)-2,15-dioxo-3,14,16-triaza-tricyclo[14.3.0.0*4,6*]nonadec-7-ene-4-carbonyl]-amide (21j)

To a stirred solution of the crude oxazolinone 21i (0.328 g, 0.64 mmol) in dichloro-methane (4 ml) was added cyclopropylsulfonamide (0.117 g, 0.96 mmol) and 1,8-diazabicyclo[5.4.0]-undec-7-ene (0.19 ml, 1.3 mmol), then stirred at rt overnight. The reaction mixture was monitored by LC-MS then diluted with dichloromethane (20 ml), washed successively with aq. 10% citric acid (3×15 ml) and brine (1×15 ml), then dried (Na$_2$SO$_4$), filtered and concentrated into an off-white foam. Column chromatography of the residue using stepwise gradient elution (ethyl acetate in toluene 60-100%) followed by concentration and drying of the appropriate fractions gave the title compound as a colorless foam (0.27 g, 66% over 3 steps).

NMR data (500 MHz, DMSO-d$_6$): $^1$H, δ 0.9-1.6 (m, 14H), 1.80 (m, 1H), 1.90 (m, 1H), 2.0-2.2 (m, 3H), 2.25 (m, 1H), 2.95 (m, 1H), 3.05 (m, 1H), 3.3-3.4 (m, 2H), 3.50 (q, 2H), 3.7-3.8 (m, 4H), 3.97 (d, 1H), 4.3-4.4 (m, 2H), 4.55 (d, 1H), 4.63 (m, 2H), 5.12 (m, 1H), 5.70 (m, 1H), 6.88 (d, 2H), 7.19 (d, 2H), 8.12 (s, 1H). LR-MS: Calcd for $C_{31}H_{45}N_4O_8S$: 633. Found: 633 [M+H].

Step k: Cyclopropanesulfonic acid (18-hydroxy-2,15-dioxo-3,14,16-triaza-tricyclo[14.3.0.0*4,6*]nonadec-7-ene-4-carbonyl)-amide (21k)

A solution of the acetal 21j (0.038 g, 0.06 mmol) in 1:1:1 THF-methanol-2 M aq. hydrochloric acid (1.5 ml) was stirred at rt for 30 min, then additional conc. hydrochloric acid (0.1 ml) was added and then stirred at rt overnight. The reaction mixture was then neutralized using aq. saturated sodium hydrogen carbonate, then concentrated onto silica. Flash chromatography of the residue using 9:1 ethyl acetate methanol gave a colorless foam (0.020 g, 73%). LR-MS: Calcd for $C_{20}H_{29}N_4O_6S$: 453. Found: 453 [M–H].

Inhibitors of the invention are obtained from intermediate 21k by performing a carbamoylation reaction using any of the methods described above, for example as described in Example 1 step i, or in Example 10.

Example 22

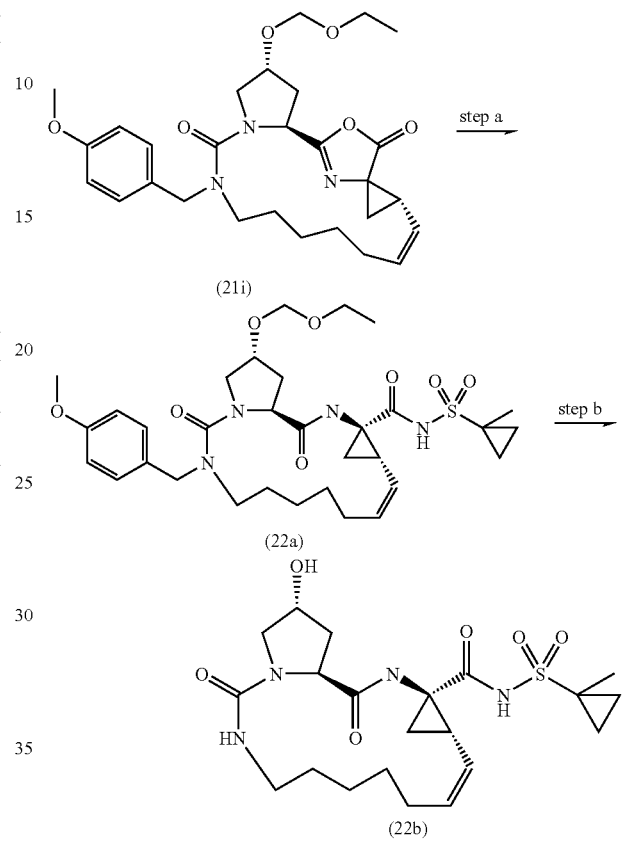

Step a: 1-Methyl-cyclopropanesulfonic acid [18-ethoxymethoxy-14-(4-methoxy-benzyl)-2,15-dioxo-3,14,16-triaza-tricyclo[14.3.0.0*4,6*]nonadec-7-ene-4-carbonyl]-amide (22a)

To a stirred solution of the oxazolinone 21i (0.372 g, 0.73 mmol) in dichloromethane (4 ml) was added cyclopropylmethylsulfonamide (0.147 g, 1.09 mmol) and 1,8-diaza bicyclo[5.4.0]-undec-7-ene (0.22 ml, 1.45 mmol) then stirred at rt overnight. Work up and chromatography as described in Example 19 step j gave the desired product as a colorless syrup which started to crystallize upon standing (0.31 g, 65% over 3 steps). NMR data (500 MHz, DMSO-d$_6$): $^1$H, δ 0.92 (m, 2H), 1.1-1.6 (m, 15H), 1.78 (m, 1H), 1.88 (m, 1H), 2.0-2.1 (m, 3H), 2.26 (m, 1H), 3.02 (m, 1H), 3.2-3.4 (m, 2H), 3.49 (q, 2H), 3.7-3.8 (m, 4H), 3.95 (d, 1H), 4.3-4.4 (m, 2H), 4.54 (d, 1H), 4.6-4.7 (m, 2H), 5.06 (m, 1H), 5.69 (m, 1H), 6.88 (d, 2H), 7.19 (d, 2H), 8.22 (s, 1H), 11.23 (s, 1H). LR-MS: Calcd for $C_{32}H_{47}N_4O_8S$: 647. Found: 647 [M+H].

Step b: 1-Methyl-cyclopropanesulfonic acid (18-hydroxy-2,15-dioxo-3,14,16-triaza-tricyclo[14.3.0.0*4,6*]nonadec-7-ene-4-carbonyl)-amide (22b)

The acetal compound 22a (0.301 g, 0.465 mmol) was deprotected using 2:1:0.1 dichloromethane/trifluoroacetic acid/H$_2$O (6.2 ml) at rt for 4 h, then conc onto silica and flash chromatography using 9:1 ethyl acetate/methanol gave the product as a colorless foam (0.065 g, 30%). LR-MS: Calcd for C$_{21}$H$_{33}$N$_4$O$_6$S: 469. Found: 469 [M+H].

Compounds of formula (I) are obtained from intermediate 22b by performing a carbamoylation reaction using any of the methods described above, for example as described in Example 1 step i, or in Example 10.

Example 23

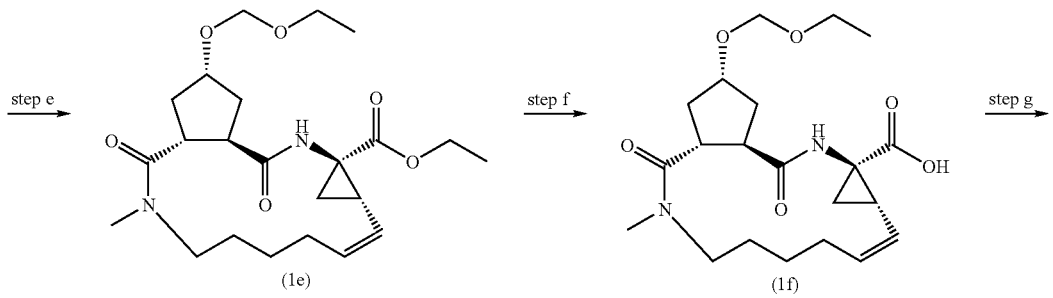

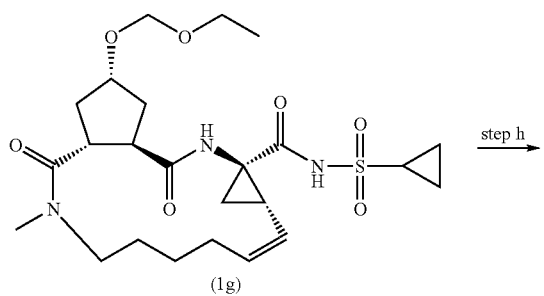

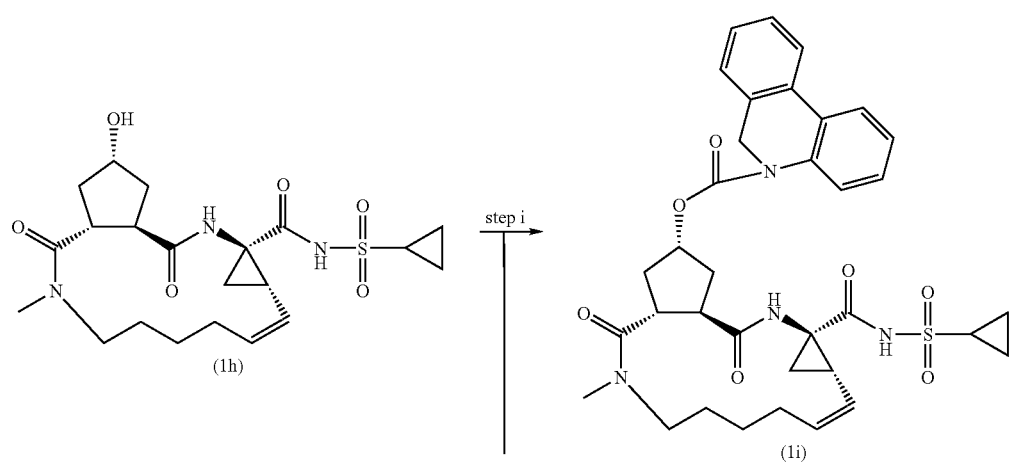

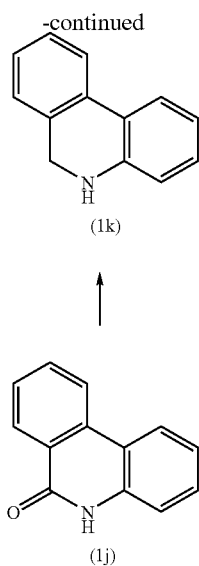

Step i: 6H-Phenanthridine-5-carboxylic acid 4-cyclopropanesulfonylaminocarbonyl-13-methyl-2,14-dioxo-3,13-diaza-tricyclo[13.3.0.0$^{4,6}$]octadec-7-en-17-yl ester (1i)

The 5,6-dihydro-phenanthridine (1k) was prepared using the following procedure: Into a 500 mL round bottom flask equipped with a magnetic stir bar and a reflux condensor was placed 6(5H)-Phenanthridinone (1000 mg, 5123 µmol), THF (250 mL) (fine suspension). The flask is sparged with nitrogen, 2M BH3-dimethylsulfide complex in THF (10 mL) is added. This is allowed to stir at reflux for 24 hours. TLC shows reaction still incomplete (1/1, ethyl acetate/heptane). Solvents removed under reduced pressure. Water (50 mL) and ethyl acetate (100 mL) added. The aqueous layer is separated with ethyl acetate (3×100 mL). The organic layers are combined, dried (sodium sulfate), solids removed by filtration, and the solvents removed under reduced pressure. This is purified by silica column chromatography using heptane to 50% ethylacetate in heptane. The best fractions are pooled and the solvents are removed under reduced pressure to afford an off-white solid (270 mg, Yield: 29%). LC-MS shows mass 182 (M+H)+.

The alcohol 1h (15 mg) was dissolved in dry DCE and 20 mg of sodium bicarbonate was added, followed by 2 ml of a phosgene solution in toluene (20%). The reaction mixture was stirred at room temperature for 3 h and then concentrated by rotary evaporation and dried from excess of phosgene in high vacuum (1.5 h). The dry reaction mixture was transferred into a "microwave" vial (2-5 ml), mixed with dry DCE (3 ml), 5,6-dihydro-phenanthridine (1k) (2 eq), potassium carbonate (9 mg, 1.5 eq), pulverized molecular sieves (4 Å, 5 mg) and heated in a microwave at 100° C. for 45 min. The reaction mixture was passed through short pad of silica (eluent DCM, then 10% methanol in DCM). The resulting fractions containing the desired carbamate compound were combined, concentrated by rotary evaporation and purified by column chromatography on YMC silica (15 g, ethyl acetate/petroleum ether 1:3 to remove excess of 5,6-dihydro-phenanthridine (1k), followed by dichloromethane and then 2% methanol in dichloromethane) to give the title compound as a powder.

Example 24

1-Methylcyclopropanesulfonic acid (17-hydroxy-13-methyl-2,14-dioxo-3,13-diaza-tricyclo[13.3.0.0*4,6*]octadec-7-ene-4-carbonyl)-amide (24)

Compound (6b), prepared as described above, is reacted with cyclic amine (23k) as described in example 23, yielding the methylcyclopropyl analogue of (23i).

Activity of Compounds of Formula (I)

Replicon Assay

The compounds of formula (I) were examined for activity in the inhibition of HCV RNA replication in a cellular assay. The assay demonstrated that the compounds of formula (I) exhibited activity against HCV replicons functional in a cell culture. The cellular assay was based on a bicistronic expression construct, as described by Lohmann et al. (1999) Science vol. 285 pp. 110-113 with modifications described by Krieger et al. (2001) Journal of Virology 75: 4614-4624, in a multi-target screening strategy. In essence, the method was as follows.

The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (FfL-luciferase), and a selectable marker portion (neo$^R$, neomycine phosphotransferase). The construct is bordered by 5' and 3' NTRs (non-translated regions) from HCV type 1b. Continued culture of the replicon cells in the presence of G418 (neo$^R$) is dependent on the replication of the HCV RNA. The stably transfected replicon cells that express HCV RNA, which replicates autonomously and to high levels, encoding inter alia luciferase, are used for screening the antiviral compounds.

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound on luciferase activity was monitored on the Huh-Luc cells, enabling a dose-response curve for each test compound. EC50 values were then calculated, which value represents the amount of the compound required to decrease by 50% the level of detected luciferase activity, or more specifically, the ability of the genetically linked HCV replicon RNA to replicate.

Inhibition Assay

The aim of this in vitro assay was to measure the inhibition of HCV NS3/4A protease complexes by the compounds of the present invention. This assay provides an indication of how effective compounds of the present invention would be in inhibiting HCV NS3/4A proteolytic activity.

The inhibition of full-length hepatitis C NS3 protease enzyme was measured essentially as described in Poliakov, 2002 Prot Expression & Purification 25 363 371. Briefly, the hydrolysis of a depsipeptide substrate, Ac-DED(Edans)EEA-buψ[COO]ASK(Dabcyl)-$NH_2$ (AnaSpec, San José, USA), was measured spectrofluorometrically in the presence of a peptide cofactor, KKGSVVIVGRIVLSGK (Åke Engström, Department of Medical Biochemistry and Microbiology, Uppsala University, Sweden). [Landro, 1997 #Biochem 36 9340-9348]. The enzyme (1 nM) was incubated in 50 mM HEPES, pH 7.5, 10 mM DTT, 40% glycerol, 0.1% n-octyl-D-glucoside, with 25 µM NS4A cofactor and inhibitor at 30° C. for 10 min, whereupon the reaction was initiated by addition of 0.5 µM substrate. Inhibitors were dissolved in DMSO, sonicated for 30 sec. and vortexed. The solutions were stored at −20° C. between measurements.

The final concentration of DMSO in the assay sample was adjusted to 3.3%. The rate of hydrolysis was corrected for inner filter effects according to published procedures [Liu, Analytical Biochemistry, 1999, vol. 267, pp. 331-335]. Ki values were estimated by non-linear regression analysis (GraFit, Erithacus Software, Staines, MX, UK), using a model for competitive inhibition and a fixed value for Km (0.15 µM). A minimum of two replicates was performed for all measurements.

Compounds of the invention are preferably potent against wild type virus and mutant HCV virus, especially virus comprising drug escape mutations. Drug escape mutations are those which arise in patients due to the selective pressure of a prior art anti viral and which confer enhanced resistance to that antiviral.

The inhibition of certain mutant HCV virus exhibited by the compounds of the invention were determined as described in WO2004/039970.

A156T and D168V are particularly relevant drug escape mutants in the context of HCV therapy using NS3 protease inhibitors and compounds of the invention preferably have low Ki values against these mutants.

The following Table 1 lists compounds that were prepared according to any one of the above examples. The activities of the compounds tested are also depicted in Table 1. The legend for values A, B, C, D, E, and F is as follows:

value A corresponds to an $EC_{50}$ >10 µM;
value B corresponds to an $EC_{50}$ between 10 µM and 1 µM;
value C corresponds to an $EC_{50}$ between 0.99 µM and 200 nM;
value D corresponds to an $EC_{50}$ between 199 nM and 0.5 nM.
value E corresponds to a Ki>100 nM;
value F corresponds to a Ki between 100 nM and 30 nM;
value G corresponds to a Ki between 29.9 nM and 0.1 nM;

| Example No | $EC_{50}$ Replicon assay | Ki Enzyme assay |
|---|---|---|
| 1 | A | F |
| 2 | B | G |
| 3 | B | G |
| 5 | B | |
| 6c | A | |
| 9 | B | |
| 10 | B | |
| 11 | B | |
| 12 | C | |
| 13 | D | |
| 14 | C | |
| 15 | A | |
| 16 | B | |
| 17 | B | |
| 18 | C | |

The invention claimed is:
1. A compound of the formula (I):

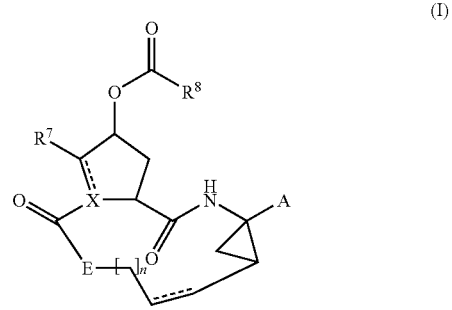

wherein
A is —C(=O)$OR^1$, —C(=O)—NH—$SO_2$—$R^2$, —C(=O)C(=O)$NR^{3a}R^{3b}$, —C(=O)—NH—$SO_2$—$NR^{3a}R^{3b}$, —C(=O)NH—P(=O)($OR^{4a}$)($R^{4b}$), or —P(=O)($OR^{4a}$)($R^{4b}$)
wherein;
$R^1$ is hydrogen; aryl; Het; $C_{3-7}$cycloalkyl optionally substituted with $C_{1-6}$alkyl; or $C_{1-6}$alkyl optionally substituted with $C_{3-7}$cycloalkyl, aryl or with Het;
$R^2$ is aryl; Het; $C_{3-7}$cycloalkyl optionally substituted with $C_{1-6}$alkyl; or $C_{1-6}$alkyl optionally substituted with $C_{3-7}$cycloalkyl, aryl, or with Het;
$R^{3a}$ and $R^{3b}$ each independently are hydrogen; $C_{1-6}$alkyl optionally substituted with $C_{1-6}$alkoxy, hydroxy, halo, $C_{3-7}$cycloalkyl, aryl, or with Het; aryl; $C_{2-6}$alkenyl; Het; $C_{3-7}$cycloalkyl optionally substituted with $C_{1-6}$alkyl; or $R^{3a}$ and $R^{3b}$ together with the nitrogen atom to which they are attached form a group $Het^1$; and $R^{3a}$ may also be $C_{1-6}$alkoxy;
$R^{4a}$ is hydrogen, $C_{1-6}$alkyl, $C_{2-6}$alkenyl, $C_{3-7}$cycloalkyl, aryl, or $C_{1-6}$alkyl optionally substituted with $C_{3-7}$cycloalkyl or aryl;
$R^{4b}$ is $R^{4b'}$, $OR^{4b'}$ or $NHR^{4b'}$;
$R^{4b'}$ is $C_{1-6}$alkyl, $C_{2-6}$alkenyl, $C_{3-7}$cycloalkyl, aryl, or $C_{1-6}$alkyl optionally substituted with $C_{3-7}$cycloalkyl or with aryl;
X is N, CH and when X bears a double bond it is C;
E is $NR^5$, or when X is N then E is $NR^5$ or $CR^{6a}R^{6b}$;
$R^5$ is hydrogen, $C_{1-6}$alkyl, $C_{1-6}$alkoxy$C_{1-6}$alkyl, or $C_{3-7}$cycloalkyl;

$R^{6a}$ and $R^{6b}$ are independently hydrogen or $C_{1-6}$alkyl, or $R^{6a}$ and $R^{6b}$ together with the carbon atom to which they are attached form $C_{3-7}$cycloalkyl;

n is 3, 4, 5 or 6;

each dotted line - - - independently represents an optional double bond;

$R^7$ is hydrogen, or where X is C or CH, $R^7$ may also be $C_{1-6}$alkyl;

$R^8$ is a radical of formula

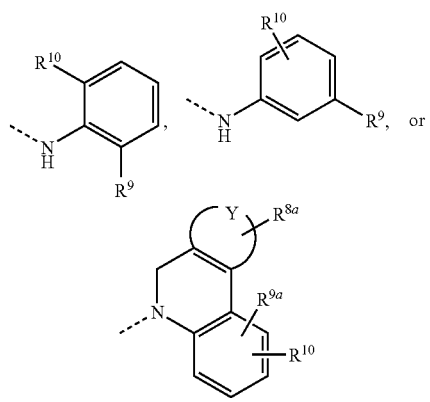

$R^{8a}$ and $R^{9a}$ each independently are hydrogen, $C_{1-6}$alkyl, $C_{2-6}$alkenyl, $C_{1-6}$alkoxy, hydroxy, halo, polyhalo$C_{1-6}$alkyl, cyano, amino, mono- or $C_{1-6}$dialkylamino;

each $R^9$ independently is $C_{1-6}$alkyl optionally substituted with $C_{1-6}$alkoxy, hydroxy, or halo; $C_{3-7}$cycloalkyl; $C_{2-6}$alkenyl; $C_{1-6}$alkoxy; $C_{3-7}$cycloalkyloxy; aryloxy; Het-O—; hydroxy; cyano; polyhalo$C_{1-6}$alkyl; mono- or $C_{1-6}$dialkylamino;

each $R^{10}$ independently is hydrogen, $C_{1-6}$alkyl, $C_{2-6}$alkenyl, $C_{1-6}$alkoxy, hydroxy, halo, polyhalo$C_{1-6}$alkyl, cyano, amino, mono- or $C_{1-6}$dialkylamino;

each aryl independently is phenyl optionally substituted with one, two or three substituents selected from halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di$C_{1-6}$alkyl-amino, azido, mercapto, $C_{1-6}$alkylthio, polyhalo$C_{1-6}$alkyl, polyhalo$C_{1-6}$alkoxy, $C_{3-7}$cycloalkyl, and Het$^1$;

each Het independently is a 5 or 6 membered saturated, partially unsaturated or completely unsaturated heterocyclic ring containing 1, 2, 3 or 4 heteroatoms each independently selected from nitrogen, oxygen and sulfur, said heterocyclic ring being optionally substituted with one, two or three substituents each independently selected from halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di$C_{1-6}$alkylamino, azido, mercapto, polyhalo$C_{1-6}$alkyl, polyhalo$C_{1-6}$alkoxy, $C_{3-7}$cycloalkyl, Het$^1$;

each Het$^1$ independently is pyrrolidinyl, piperidinyl, piperazinyl, 4-$C_{1-6}$alkyl-piperazinyl, 4-$C_{1-6}$alkylcarbonylpiperazinyl, and morpholinyl and wherein the morpholinyl and piperidinyl groups may optionally substituted with one or two $C_{1-6}$alkyl radicals;

or an N-oxide, a stereoisomer, a pharmaceutically acceptable addition salt, or pharmaceutically acceptable solvate thereof.

2. A compound according to claim 1, wherein n is 4 or 5.

3. A compound according to claim 1, wherein ----- adjacent the —(CH$_2$)$_n$— moiety is a double bond.

4. A compound according to claim 1, wherein ----- in the five membered ring having X is a single bond and $R^7$ is hydrogen.

5. A compound according to claim 1, wherein E is NR$^5$.

6. A compound according to claim 1, wherein X is N.

7. A compound according to claim 1, wherein $R^8$ is a radical of formula:

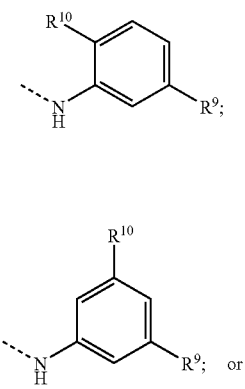

8. A compound according to claim 1, wherein $R^8$ is a radical of formula:

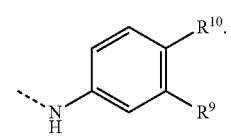

9. A compound according to claim 7, wherein $R^9$ is $C_{1-6}$alkyl; $C_{1-6}$alkoxy; aryloxy; Het-O—; cyano; or $R^9$ is $C_{1-6}$alkoxy or aryloxy.

10. A compound according to claim 7, wherein $R^{10}$ is hydrogen; $C_{1-6}$alkyl; $C_{1-6}$alkoxy; or cyano.

11. A compound according to claim 1, wherein the group

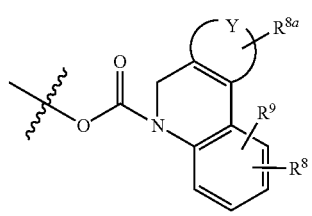

has the structure:

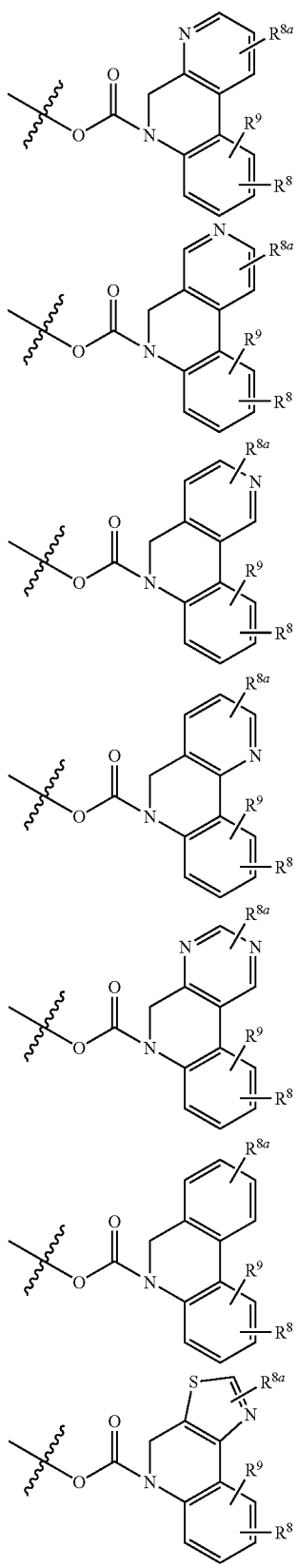

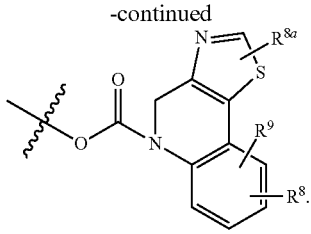

12. A compound according to claim 11, wherein the group

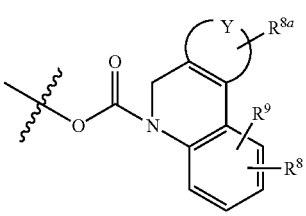

has the structure:

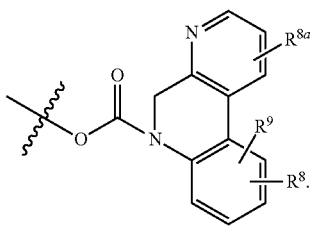

13. A compound according to claim 11, wherein $R^8$, $R^{8a}$, $R^9$ are hydrogen.

14. A compound according to claim 1, wherein aryl is phenyl optionally substituted with $C_{1-6}$alkoxy and Het is pyridyl or pyrimidinyl.

15. A compound according to claim 1, wherein A is —C(=O)—NH—SO$_2$R$^2$, in particular wherein R$^2$ is $C_{3-7}$cycloalkyl, phenyl or a group Het, e.g. thiazolyl or pyridyl, either of which is optionally substituted with one or more, such as one or two substituents selected from $C_{1-6}$alkyl, $C_{1-6}$alkoxy, trifluoromethyl, and halo, or in particular with one or two substituents selected from methyl, fluoro and chloro; or A is C(=O)OR$^1$ wherein R$^1$ is hydrogen or $C_1$-$C_6$alkyl, such as methyl.

16. A pharmaceutical composition comprising said compound of formula (I) of claim 1 and a carrier.

17. A method for treating an HCV viral infection comprising administering the effective amount of the pharmaceutical composition of claim 16 to a subject in need thereof.

18. A pharmaceutical composition comprising a compound of formula (I) of claim 1 and an antiviral compound.

19. The composition of claim 18, wherein said antiviral compound is an anti-HCV compound.

* * * * *